(12) United States Patent
Papsdorf et al.

(10) Patent No.: US 8,820,513 B2
(45) Date of Patent: Sep. 2, 2014

(54) METHODS FOR TRANSFERRING DISCRETE ARTICLES

(75) Inventors: Clifford Theodore Papsdorf, Loveland, OH (US); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 129 days.

(21) Appl. No.: 13/447,531

(22) Filed: Apr. 16, 2012

(65) Prior Publication Data

US 2013/0270065 A1    Oct. 17, 2013

(51) Int. Cl.
*B65G 37/00* (2006.01)

(52) U.S. Cl.
USPC .................. 198/478.1; 198/470.1; 198/471.1

(58) Field of Classification Search
USPC ........... 198/470.1, 471.1, 478.1, 476.1, 477.1
See application file for complete search history.

(56) References Cited

U.S. PATENT DOCUMENTS

| | | |
|---|---|---|
| 3,963,557 A | 6/1976 | Patterson |
| 4,181,555 A | 1/1980 | Hoffmann |
| 4,297,157 A | 10/1981 | Van Vliet |
| 4,333,790 A | 6/1982 | Schaffron |
| 4,429,781 A | 2/1984 | Holzhauser |
| 4,574,022 A | 3/1986 | Johnson et al. |
| 4,578,133 A | 3/1986 | Oshefsky et al. |
| 4,610,751 A | 9/1986 | Eschler |
| 4,617,082 A | 10/1986 | Oshefsky et al. |
| 4,632,721 A | 12/1986 | Hoffmann et al. |
| 4,642,150 A | 2/1987 | Stemmler |
| 4,648,928 A | 3/1987 | Ales |
| 4,722,432 A | 2/1988 | Staton |
| 4,726,874 A | 2/1988 | Van Vliet |
| 4,726,876 A | 2/1988 | Tomsovic, Jr. |
| 4,738,348 A | 4/1988 | Sillner |
| 4,758,293 A | 7/1988 | Samida |
| 4,767,487 A | 8/1988 | Tomsovic, Jr. |
| 4,786,046 A | 11/1988 | Freeman et al. |
| 4,813,946 A | 3/1989 | Sabee |
| 4,834,741 A | 5/1989 | Sabee |
| 4,838,969 A | 6/1989 | Nomura et al. |
| 4,838,982 A | 6/1989 | Klaeser et al. |
| 4,863,542 A | 9/1989 | Oshefsky et al. |
| 4,880,102 A | 11/1989 | Indrebo |
| 4,908,247 A | 3/1990 | Baird et al. |

(Continued)

FOREIGN PATENT DOCUMENTS

JP    2005212149    8/2005
WO    WO-2010/078572    7/2010

OTHER PUBLICATIONS

International Search Report and Written Opinion, PCT/US2013/036716, date of mailing Jul. 26, 2013.
All Office Actions, U.S. Patent Appl. No. 8,607,959.

(Continued)

*Primary Examiner* — James R Bidwell
(74) *Attorney, Agent, or Firm* — Christian M. Best

(57) ABSTRACT

The present disclosure is directed to a method of transferring discrete articles from or to a moving carrier member using a transfer assembly. The transfer assembly comprises a frame defining a rotation axis and a transfer member comprising a transfer surface configured to receive one of the discrete articles. The method comprises rotating the transfer member about the rotation axis and maintaining the transfer surface at a substantially constant minimum distance away from the moving carrier member at the point of discrete article transfer.

27 Claims, 43 Drawing Sheets

(56) References Cited

U.S. PATENT DOCUMENTS

| | | | |
|---|---|---|---|
| 4,921,387 A | 5/1990 | Bennington | |
| 4,925,520 A | 5/1990 | Beaudoin et al. | |
| 4,940,464 A | 7/1990 | Van Gompel et al. | |
| 4,941,939 A | 7/1990 | Nomura et al. | |
| 4,960,186 A | 10/1990 | Honda | |
| 4,968,313 A | 11/1990 | Sabee | |
| 4,995,928 A | 2/1991 | Sabee | |
| 5,025,910 A | 6/1991 | Lasure et al. | |
| 5,046,272 A | 9/1991 | Vogt et al. | |
| 5,091,039 A | 2/1992 | Ujimoto et al. | |
| 5,092,861 A | 3/1992 | Nomura et al. | |
| 5,092,862 A | 3/1992 | Muckenfuhs et al. | |
| 5,116,452 A | 5/1992 | Eder | |
| 5,143,679 A | 9/1992 | Weber et al. | |
| 5,149,392 A | 9/1992 | Plaessmann | |
| 5,156,793 A | 10/1992 | Buell et al. | |
| 5,167,897 A | 12/1992 | Weber et al. | |
| 5,177,841 A | 1/1993 | Hamuro et al. | |
| 5,188,212 A * | 2/1993 | Munsch | 198/457.07 |
| 5,224,405 A | 7/1993 | Pohjola | |
| 5,235,515 A | 8/1993 | Ungpiyakul et al. | |
| 5,246,433 A | 9/1993 | Hasse et al. | |
| 5,305,653 A | 4/1994 | Ohtani et al. | |
| 5,360,420 A | 11/1994 | Cook et al. | |
| 5,380,381 A | 1/1995 | Otruba | |
| 5,413,651 A | 5/1995 | Otruba | |
| 5,429,694 A | 7/1995 | Herrmann | |
| 5,500,075 A | 3/1996 | Herrmann | |
| 5,556,504 A | 9/1996 | Rajala et al. | |
| 5,569,234 A | 10/1996 | Buell et al. | |
| 5,582,668 A | 12/1996 | Kling | |
| 5,584,954 A | 12/1996 | van der Klugt | |
| 5,591,297 A | 1/1997 | Ahr | |
| 5,591,298 A | 1/1997 | Goodman et al. | |
| 5,599,335 A | 2/1997 | Goldman et al. | |
| 5,643,396 A | 7/1997 | Rajala et al. | |
| 5,643,588 A | 7/1997 | Roe et al. | |
| 5,660,657 A | 8/1997 | Rajala et al. | |
| 5,660,664 A | 8/1997 | Herrmann | |
| 5,674,216 A | 10/1997 | Buell et al. | |
| 5,684,344 A | 11/1997 | Takei | |
| 5,693,195 A | 12/1997 | Saito et al. | |
| 5,695,963 A | 12/1997 | McKnight et al. | |
| 5,702,551 A | 12/1997 | Huber et al. | |
| 5,709,770 A | 1/1998 | Asghar et al. | |
| 5,716,478 A | 2/1998 | Boothe et al. | |
| 5,735,996 A | 4/1998 | Asghar et al. | |
| 5,759,340 A | 6/1998 | Boothe et al. | |
| 5,766,406 A | 6/1998 | Bohn et al. | |
| 5,776,289 A | 7/1998 | Steidinger | |
| 5,783,032 A | 7/1998 | O'Callaghan et al. | |
| 5,837,087 A | 11/1998 | Ahr | |
| 5,849,143 A | 12/1998 | Ingalls | |
| 5,850,711 A | 12/1998 | Takahashi et al. | |
| 5,888,343 A | 3/1999 | Olson | |
| 5,895,555 A | 4/1999 | Van Den Bergh | |
| 5,897,545 A | 4/1999 | Kline et al. | |
| 5,901,530 A * | 5/1999 | Draghetti et al. | 198/471.1 |
| 5,932,039 A | 8/1999 | Popp et al. | |
| 5,957,908 A | 9/1999 | Kline et al. | |
| 5,965,963 A | 10/1999 | Chitayat | |
| 5,968,025 A | 10/1999 | Roe et al. | |
| 5,994,798 A | 11/1999 | Chitayat | |
| 6,022,443 A | 2/2000 | Rajala et al. | |
| 6,059,710 A | 5/2000 | Rajala et al. | |
| 6,074,333 A | 6/2000 | Rajala et al. | |
| 6,086,694 A | 7/2000 | Winter et al. | |
| 6,107,537 A | 8/2000 | Elder et al. | |
| 6,118,041 A | 9/2000 | Roe et al. | |
| 6,120,487 A | 9/2000 | Ashton | |
| 6,120,489 A | 9/2000 | Johnson et al. | |
| 6,139,004 A | 10/2000 | Couillard et al. | |
| 6,149,755 A | 11/2000 | McNichols et al. | |
| 6,153,209 A | 11/2000 | Vega et al. | |
| 6,165,306 A | 12/2000 | Rajala | |
| 6,170,636 B1 | 1/2001 | Een et al. | |
| 6,250,357 B1 | 6/2001 | Niedermeyer | |
| 6,254,714 B1 | 7/2001 | Niedermeyer | |
| 6,284,081 B1 | 9/2001 | Vogt et al. | |
| 6,287,409 B1 | 9/2001 | Stephany | |
| 6,319,347 B1 | 11/2001 | Rajala et al. | |
| 6,322,547 B1 | 11/2001 | Hansson | |
| 6,325,201 B1 | 12/2001 | Bailey et al. | |
| 6,350,070 B1 | 2/2002 | Tasma | |
| 6,375,769 B1 | 4/2002 | Quereshi et al. | |
| 6,410,129 B2 | 6/2002 | Zhang et al. | |
| 6,422,375 B1 | 7/2002 | Hellman et al. | |
| 6,426,444 B2 | 7/2002 | Roe et al. | |
| 6,431,241 B1 | 8/2002 | Gonzalo | |
| 6,440,246 B1 | 8/2002 | Vogt et al. | |
| 6,450,321 B1 | 9/2002 | Blumenthal et al. | |
| 6,471,036 B1 | 10/2002 | Schlisio | |
| 6,520,236 B1 | 2/2003 | Rajala | |
| 6,527,902 B1 | 3/2003 | Rajala | |
| 6,533,879 B2 | 3/2003 | Quereshi et al. | |
| 6,540,857 B1 | 4/2003 | Coenen et al. | |
| 6,544,375 B1 | 4/2003 | Schmitz | |
| 6,550,517 B1 | 4/2003 | Hilt et al. | |
| 6,569,275 B1 | 5/2003 | Popp et al. | |
| 6,585,841 B1 | 7/2003 | Popp et al. | |
| 6,586,652 B1 | 7/2003 | Roe et al. | |
| 6,590,136 B1 | 7/2003 | Young et al. | |
| 6,604,623 B2 * | 8/2003 | Sumi et al. | 198/377.08 |
| 6,613,033 B1 | 9/2003 | Popp et al. | |
| 6,617,016 B2 | 9/2003 | Zhang et al. | |
| 6,617,490 B1 | 9/2003 | Chen et al. | |
| 6,620,276 B1 | 9/2003 | Kuntze et al. | |
| 6,627,787 B1 | 9/2003 | Roe et al. | |
| 6,635,041 B1 | 10/2003 | Popp et al. | |
| 6,648,122 B1 | 11/2003 | Hirsch et al. | |
| 6,652,504 B1 | 11/2003 | Olson et al. | |
| 6,656,312 B1 | 12/2003 | Schmitz et al. | |
| 6,689,115 B1 | 2/2004 | Popp et al. | |
| 6,692,196 B1 | 2/2004 | Simm et al. | |
| 6,692,603 B1 | 2/2004 | Lindsay et al. | |
| 6,705,453 B2 | 3/2004 | Blumenthal et al. | |
| 6,722,494 B2 | 4/2004 | Nakakado | |
| 6,748,996 B2 | 6/2004 | Nakakado et al. | |
| 6,766,217 B2 | 7/2004 | Hamada | |
| 6,766,843 B2 | 7/2004 | Hilt et al. | |
| 6,808,582 B2 | 10/2004 | Popp et al. | |
| 6,811,019 B2 | 11/2004 | Christian et al. | |
| 6,814,217 B2 | 11/2004 | Blumenthal et al. | |
| 6,820,671 B2 | 11/2004 | Clavert | |
| 6,825,393 B2 | 11/2004 | Roe et al. | |
| 6,832,679 B2 * | 12/2004 | Berndtsson | 198/471.1 |
| 6,848,566 B2 | 2/2005 | Harnish et al. | |
| 6,860,531 B2 | 3/2005 | Sherwin | |
| 6,861,571 B1 | 3/2005 | Roe et al. | |
| 6,866,137 B2 | 3/2005 | Ohiro et al. | |
| 6,895,649 B2 | 5/2005 | Kojo et al. | |
| 6,899,780 B2 | 5/2005 | Rajala et al. | |
| 6,918,485 B2 | 7/2005 | Holston et al. | |
| 6,942,086 B2 | 9/2005 | Bridges et al. | |
| 7,013,941 B2 | 3/2006 | Schneider et al. | |
| 7,045,031 B2 | 5/2006 | Popp et al. | |
| 7,093,705 B2 | 8/2006 | Ohiro et al. | |
| 7,134,258 B2 | 11/2006 | Kalany et al. | |
| 7,179,343 B2 | 2/2007 | VanEperen et al. | |
| 7,195,684 B2 | 3/2007 | Satoh | |
| 7,216,685 B2 | 5/2007 | Nakakado et al. | |
| 7,252,131 B2 | 8/2007 | Draghetti et al. | |
| 7,278,203 B2 | 10/2007 | Aoyama et al. | |
| 7,341,087 B2 | 3/2008 | Tabor et al. | |
| 7,398,870 B2 | 7/2008 | McCabe | |
| 7,533,709 B2 | 5/2009 | Meyer | |
| 7,543,697 B2 * | 6/2009 | Legallais | 198/478.1 |
| 7,587,966 B2 | 9/2009 | Nakakado et al. | |
| 7,643,904 B2 | 1/2010 | Aoyama et al. | |
| 7,721,872 B2 | 5/2010 | Aoyama et al. | |
| 7,770,712 B2 | 8/2010 | McCabe | |
| 7,841,633 B2 | 11/2010 | Nankervis et al. | |
| 8,430,226 B2 * | 4/2013 | Tokunaga et al. | 198/346.2 |
| 2002/0112939 A1 | 8/2002 | Sumi et al. | |

(56) References Cited

U.S. PATENT DOCUMENTS

| | | |
|---|---|---|
| 2002/0125105 A1 | 9/2002 | Nakakado |
| 2003/0079330 A1 | 5/2003 | Stopher et al. |
| 2003/0233082 A1 | 12/2003 | Kline et al. |
| 2004/0089516 A1 | 5/2004 | Christian et al. |
| 2004/0144619 A1 | 7/2004 | Ohiro et al. |
| 2004/0144620 A1 | 7/2004 | Ohiro et al. |
| 2004/0154161 A1 | 8/2004 | Aoyama et al. |
| 2004/0245069 A1 | 12/2004 | Hook et al. |
| 2004/0262127 A1 | 12/2004 | Harnish et al. |
| 2005/0082141 A1 | 4/2005 | Dombek |
| 2006/0185135 A1 | 8/2006 | Yamamoto et al. |
| 2007/0074953 A1 | 4/2007 | McCabe |
| 2007/0227858 A1 | 10/2007 | Aoyama et al. |
| 2008/0005895 A1 | 1/2008 | Aoyama et al. |
| 2008/0023296 A1* | 1/2008 | Aoyama et al. ............ 198/468.2 |
| 2008/0196564 A1 | 8/2008 | McCabe |
| 2008/0276439 A1 | 11/2008 | Andrews et al. |
| 2009/0312739 A1 | 12/2009 | Umebayahi et al. |
| 2010/0012458 A1 | 1/2010 | Giuliani et al. |
| 2010/0258240 A1 | 10/2010 | McCabe et al. |
| 2010/0270126 A1 | 10/2010 | Piantoni et al. |
| 2010/0300838 A1 | 12/2010 | McCabe |
| 2010/0326796 A1 | 12/2010 | Walsh |
| 2011/0287918 A1 | 11/2011 | Ogasawara et al. |
| 2012/0012439 A1 | 1/2012 | Yamamoto |
| 2013/0091998 A1 | 4/2013 | Yamamoto et al. |
| 2013/0152360 A1 | 6/2013 | Schoultz et al. |
| 2013/0153365 A1 | 6/2013 | Schoultz |

OTHER PUBLICATIONS

All Office Actions, U.S. Appl. No. 14/105,228.
All Office Actions, U.S. Appl. No. 13/447,568.
All Office Actions, U.S. Appl. No. 14/191,483.
All Office Actions, U.S. Patent Appl. No. 8,720,666.
All Office Actions, U.S. Appl. No. 14/225,582.

* cited by examiner

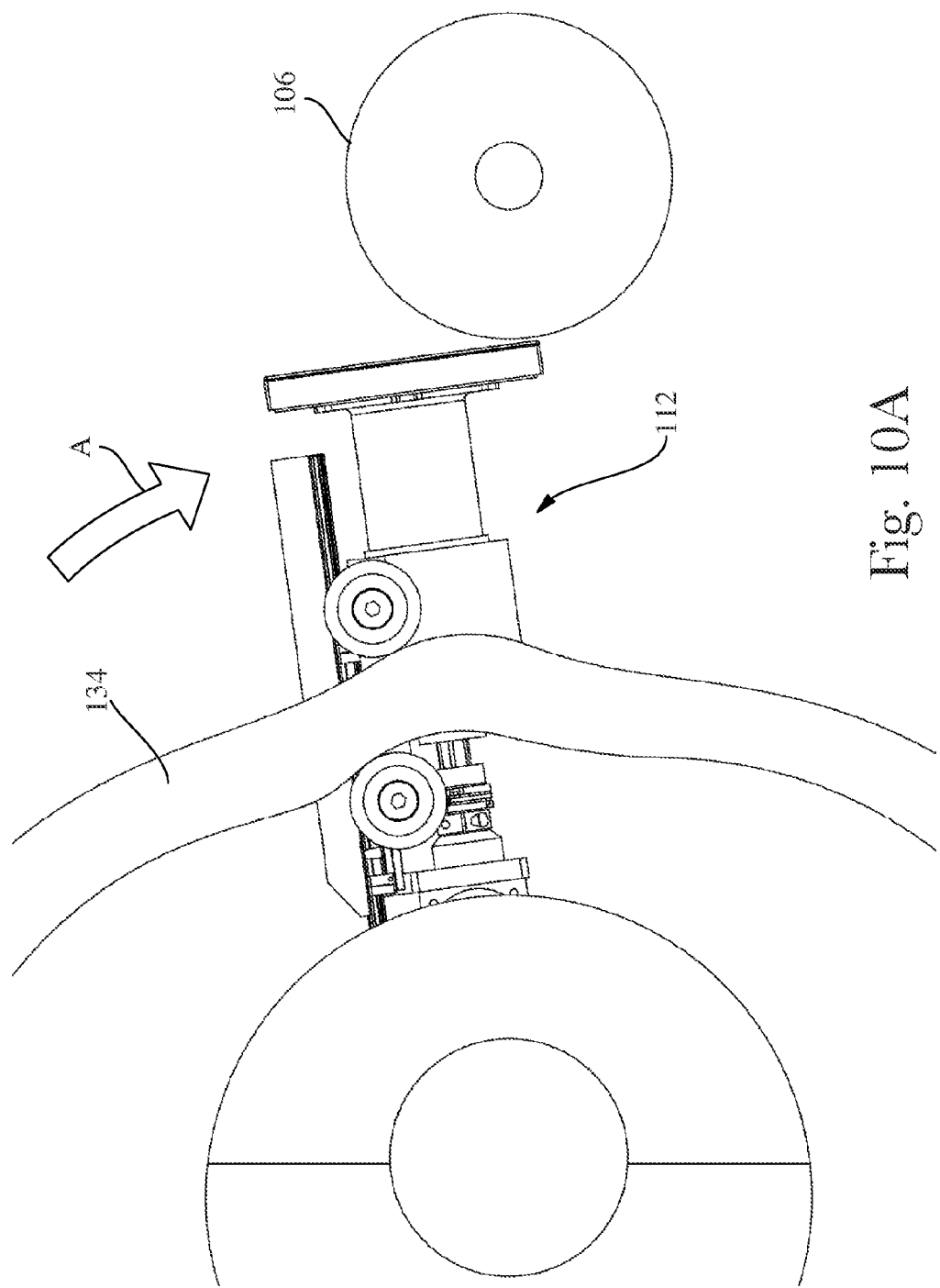

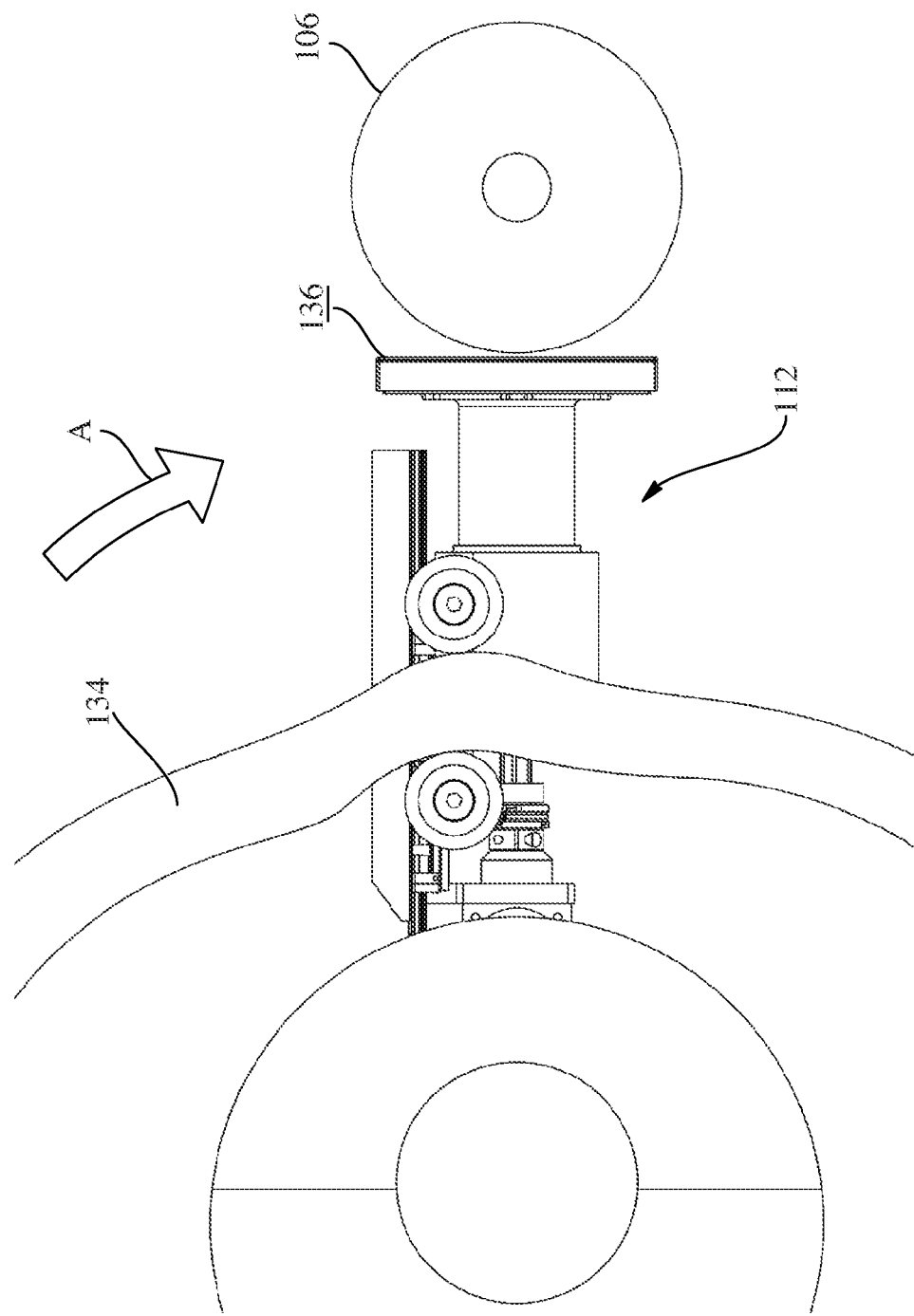

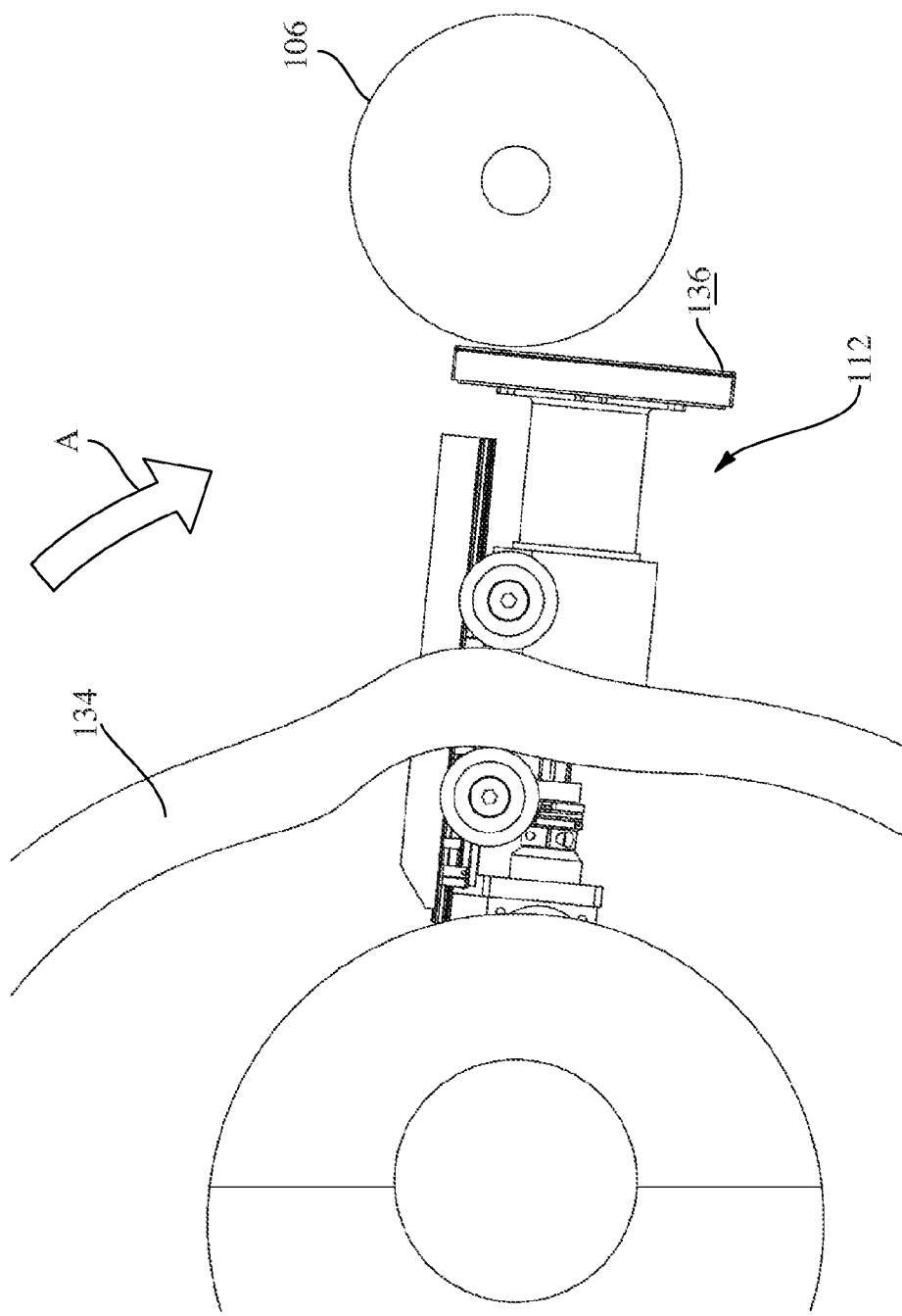

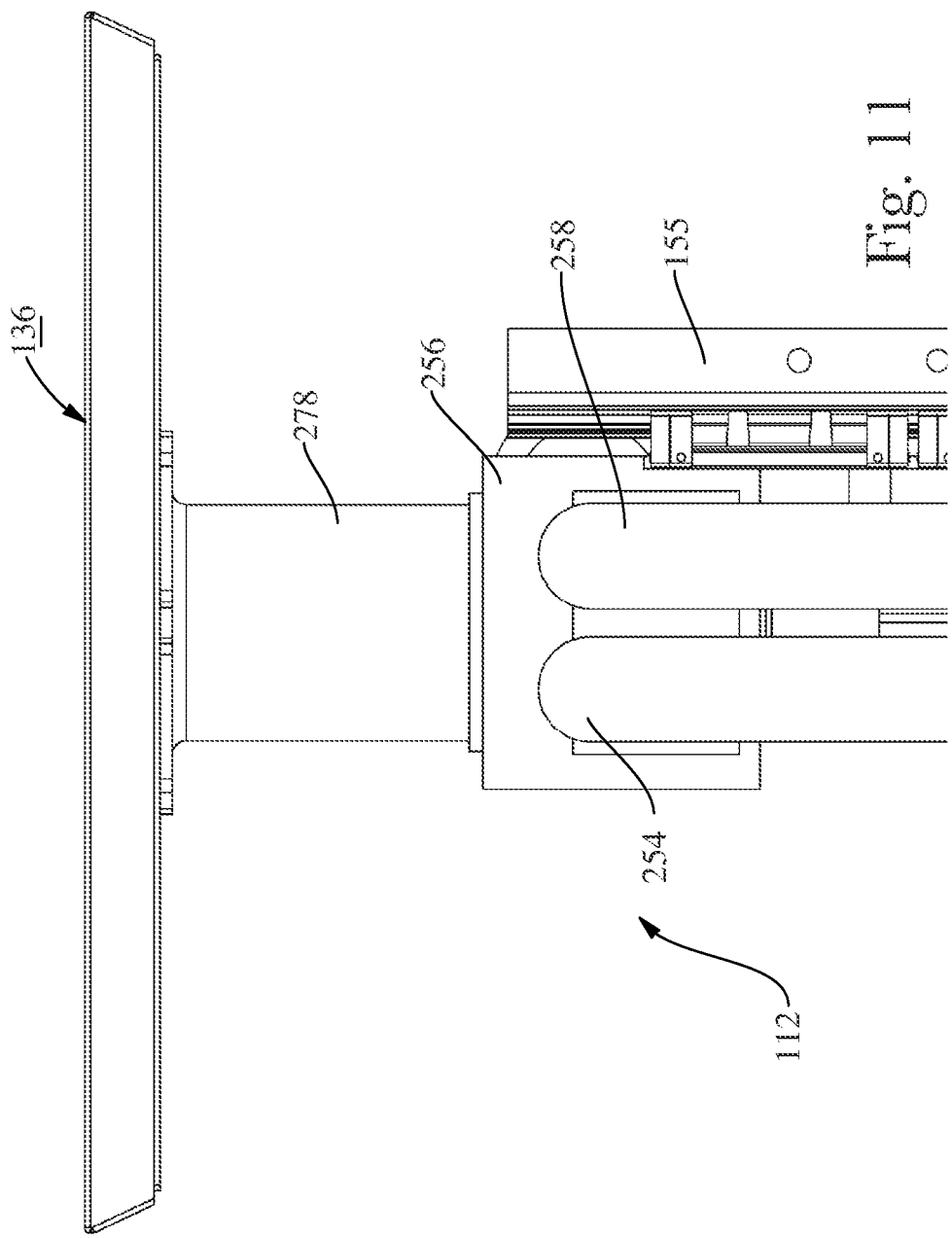

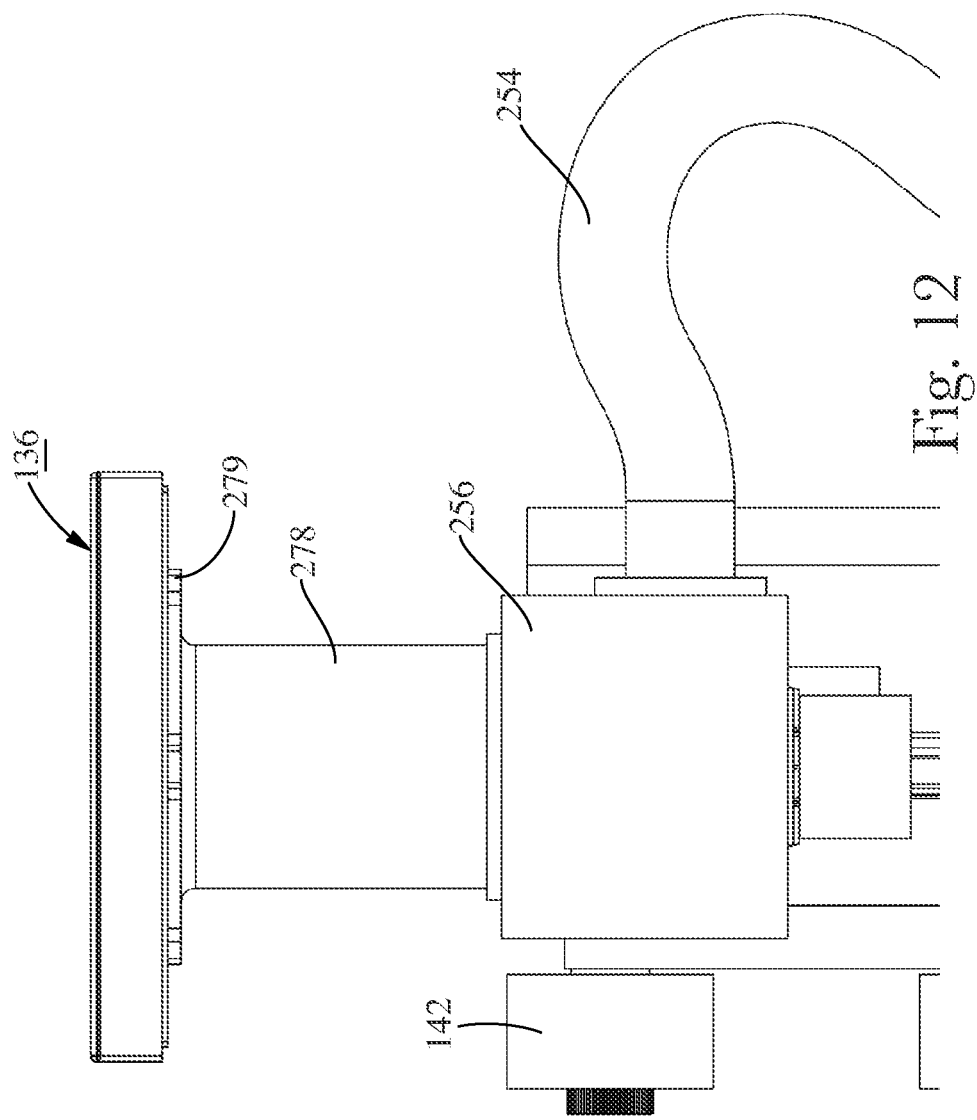

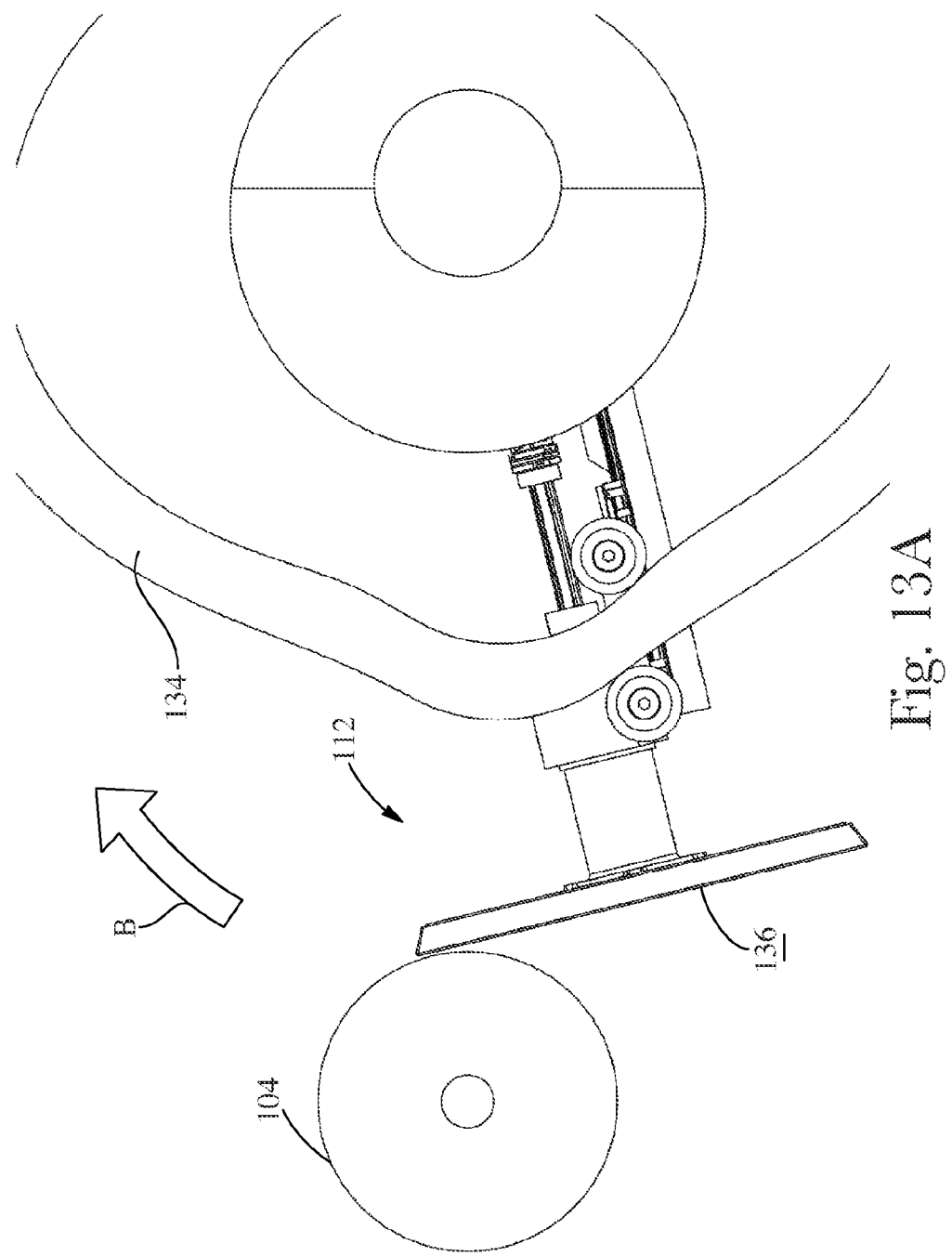

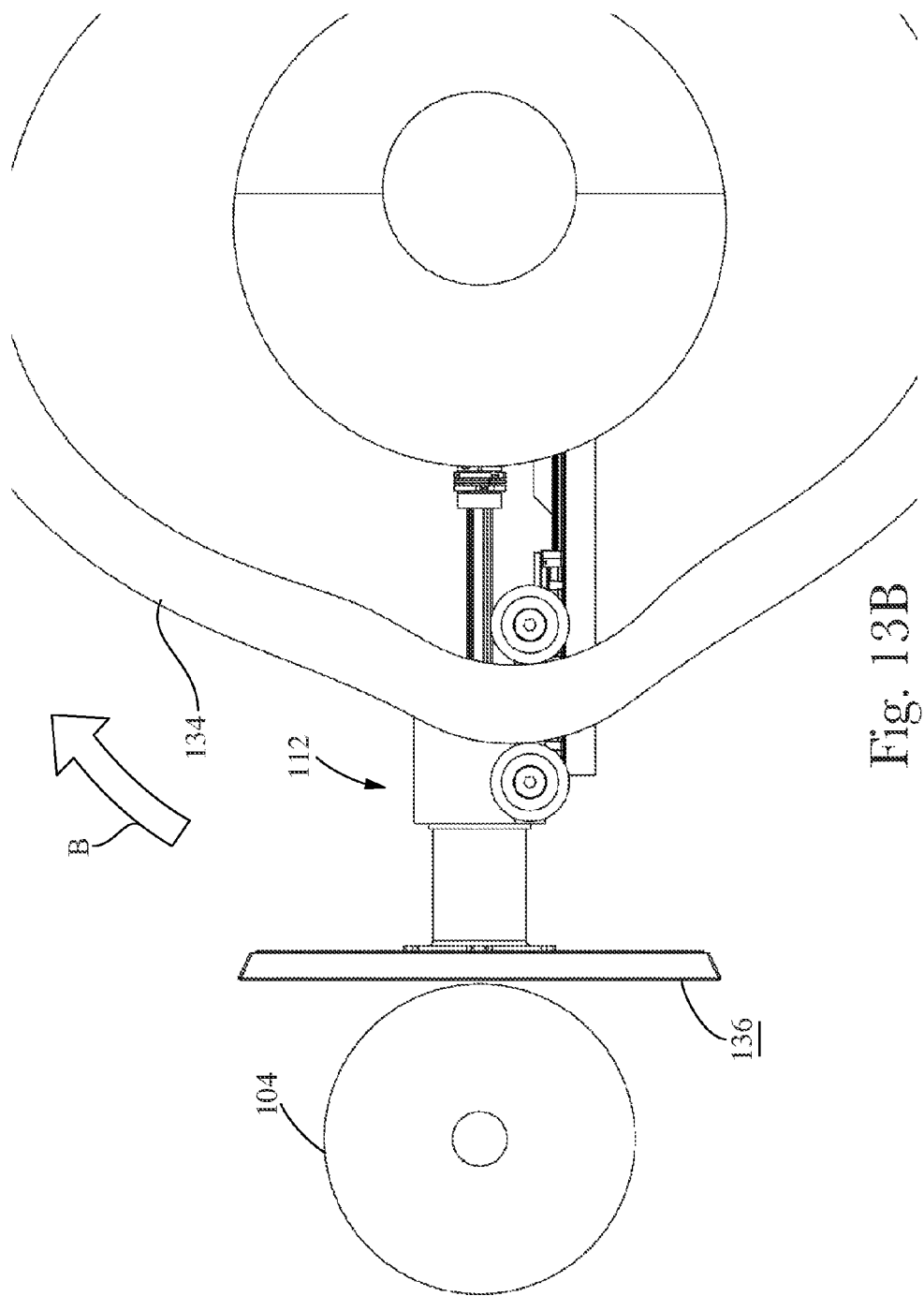

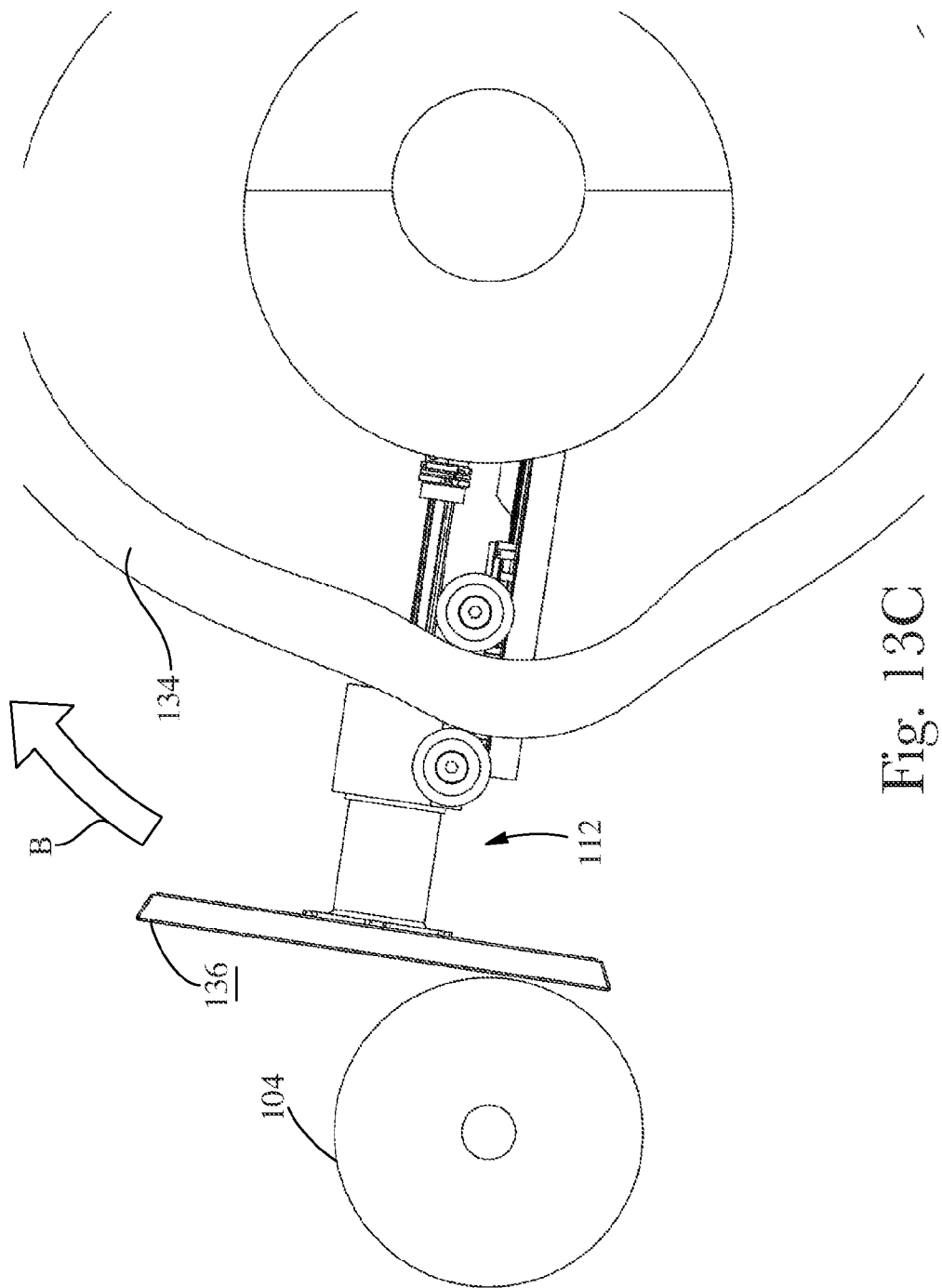

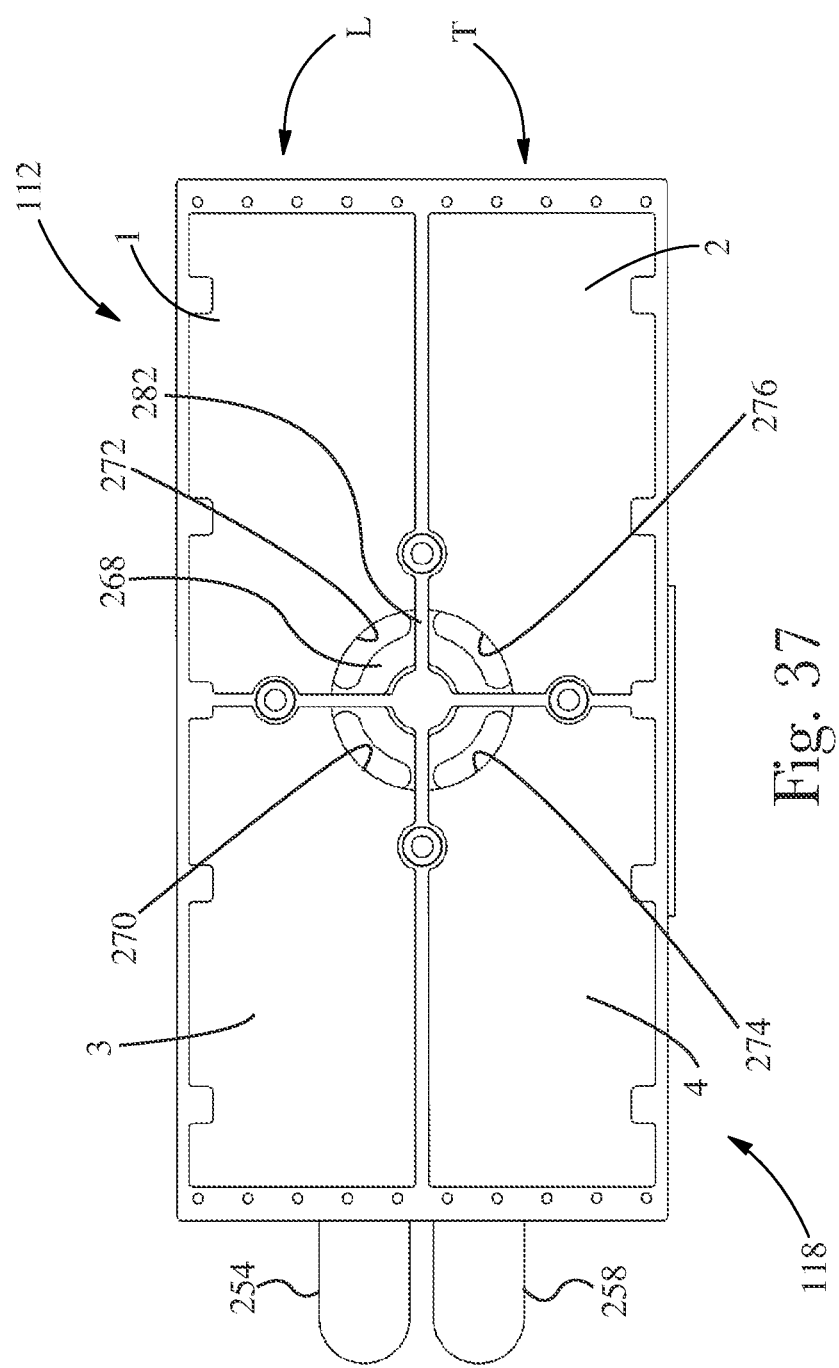

METHODS FOR TRANSFERRING DISCRETE ARTICLES

FIELD

The present disclosure generally relates to methods for transferring discrete articles and, more particularly, relates to methods for transferring discrete articles to or from a moving carrier member.

BACKGROUND

Absorbent articles, such as taped diapers or pant diapers, for example, may be manufactured by a process where discrete articles, such as a chassis of a taped diaper or a pant diaper including a topsheet, a backsheet, and an absorbent core, for example, are applied to one or more moving webs of components, such as webs of front and rear belt portions, for example, using transfer members of transfer assemblies. Often, a speed at which the discrete articles are fed into the process on a first moving carrier member is not the same as a speed of a second moving carrier member on which the moving webs of components are situated. Thus, the speed of the discrete articles should generally be changed by the transfer assemblies to match, or closely match, the speed of the webs of components on the second moving carrier member to properly apply the discrete articles to the moving webs of components without adversely affecting the process or a finished product produced by the process. In some instances, the discrete articles may also need to be turned (e.g., about 90 degrees) and repitched by the transfer assemblies after pickup from the first moving carrier member and before placement onto the second moving carrier member. A transfer assembly may have a frame defining an axis and a plurality of transfer members rotating about the axis. During such rotation, the transfer members of the transfer assembly may move past the first moving carrier member to pick up the discrete articles and move past the second moving carrier member to drop off the discrete articles.

One of the many issues with related art transfer assemblies is that they have to be run fairly slowly (e.g., 500 discrete articles per minute) to achieve suitable discrete article transfers. If the related art transfer assemblies are run at faster speeds (e.g., over 1,000 discrete articles per minute), suitable discrete article transfers may not usually be able to be achieved. If run at the higher speeds, the related art transfer assemblies may cause the discrete articles to fold over portions of themselves inappropriately, or otherwise not properly transfer, thereby resulting in disconfigured products or portions of products.

Furthermore, related art transfer assemblies typically use transfer members having arcuately shaped transfer surfaces. These arcuately shaped transfer surfaces may be suitable for pick-up or drop-off of the discrete articles, but not both. For example, if an arc of the transfer surface extends in the machine direction for pick-up and then the transfer surface is rotated 90 degrees, the arc of the transfer surface is not generally suitable for drop-off in the cross direction because the distal cross machine direction edges of the transfer surface will not be in close proximity to the second moving carrier member, thereby resulting in poor control during the transfer.

In addition to the above, if flat, or substantially flat, transfer surfaces are used in related art transfer assemblies, the leading edge of the transfer surface may be positioned quite close to the moving carrier member, the mid portion of the transfer surface may have a large gap between itself and the moving carrier member, and the trailing edge of the transfer surface may again be positioned quite close to the moving carrier member. The large gap of the mid portion of the transfer surface at the point of discrete article transfer and/or the gap variation may create many issues, such as faulty transfers and/or ruined or disconfigured products, or portions thereof, having edges or corners folded over themselves, for example. This gap variation may also cause the discrete articles to be mispositioned on webs of components on the second moving carrier member again potentially leading to ruined or disconfigured products, or portions thereof.

Another issue with the related art transfer assemblies is with the fluid control systems used to retain the discrete articles to the transfer surfaces during transfers of the discrete articles between the first moving carrier member and the second moving carrier member. Typically, a fluid pressure, such as vacuum, is either turned on or off simultaneously across the entire transfer surface. The fluid pressure can interact with the discrete components through ports in the transfer surfaces. During initial transfer of a discrete article from a first moving carrier member to a transfer surface, much of the vacuum on the trailing portion of the transfer surface is bled off to the atmosphere which consumes energy not necessarily required to achieve the transfer. During transferring the discrete article onto the second moving carrier member, the leading portion of the transfer surface may maintain vacuum even after the leading portion of the discrete article has been transferred or should have been transferred to the second moving carrier member so that the trailing portion of the discrete article remains attached to the trailing portion of the transfer surface. This can cause faulty discrete article transfers as the leading portion of the discrete articles can have a tendency to be retained to the leading portion of the transfer surfaces when it should be positioned on the second moving carrier member. This can be especially problematic at high speeds (e.g., over 1,000 discrete article transfers per minute). In other instances, the discrete articles may be blown off of the transfer surfaces by applying a positive fluid pressure to the discrete articles through ports in the transfer surfaces. This blow off may usually occur when the leading portion of the discrete components first encounters and is transferred to the second moving carrier member. As such, control of the trailing portion of the discrete articles is usually lost prior to being transferred to the second moving carrier member. This can cause faulty transfers of the discrete articles as the trailing portion of the discrete articles is not under control after blow off. This may especially be an issue when the discrete article contains stretched elastic elements that can contract when not controlled by the transfer surface or moving carrier member.

Another issue with related art transfer assemblies is the mechanism for rotation of the transfer members, which is typically a barrel cam. A barrel cam is expensive to manufacture and typically requires a great deal of maintenance, including frequent greasing and cleaning. This often requires disassembly of the machine and creates significant downtime.

What is needed are transfer assemblies, and components thereof, that can overcome the disadvantages of the related art transfer assemblies and that can transfer discrete articles at higher speeds while retaining better discrete article control at all points during the transfers.

SUMMARY

In one form, the present disclosure is directed, in part, to a method of transferring discrete articles from or to a moving carrier member using a transfer assembly. The transfer assembly comprises a frame defining a rotation axis and a transfer member comprising a substantially flat transfer surface configured to receive one or more of the discrete articles. The method comprises rotating the transfer member about the rotation axis, and maintaining the substantially flat transfer surface at a substantially constant minimum distance away from the moving carrier member at the point of discrete article transfer.

In another form, the present disclosure is directed, in part, to a method of transferring discrete articles from or to a moving carrier member using a transfer assembly. The transfer assembly comprises a frame defining a rotation axis and a transfer member comprising a transfer surface configured to receive one of the discrete articles. The method comprises rotating the transfer member about the rotation axis such that the transfer surface has a tangential velocity substantially the same as the velocity of the moving carrier member at the point of discrete article transfer, and maintaining the transfer surface at a substantially constant minimum distance away from the moving carrier member at the point of discrete article transfer.

In still another form, the present disclosure is directed, in part, to a method of transferring discrete articles from a first moving carrier member to a second moving carrier member using a transfer assembly. The transfer assembly comprises a frame defining a rotation axis and a transfer member comprising a substantially flat transfer surface configured to receive one of the discrete articles. The method comprises rotating the transfer member about the rotation axis, and maintaining the substantially flat transfer surface at a substantially constant minimum distance away from the first moving carrier member and the second moving carrier member at the points of discrete article transfer.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIGS. 10A-10C are rear views of a portion of the transfer assembly having a transfer member and transfer surface, wherein the progression of movement of the transfer surface relative to a second moving carrier member is illustrated, in accordance with various non-limiting embodiments;

FIG. 11 is a side view of a portion of transfer member comprising a flat, or substantially flat, transfer surface in accordance with one non-limiting embodiment;

FIG. 12 is a front view of the portion of the transfer member of FIG. 11 having the flat, or substantially flat, transfer surface in accordance with one non-limiting embodiment;

FIGS. 13A-13C are rear views of a portion of the transfer assembly having a transfer member and transfer surface, wherein the progression of movement of the transfer surface relative to a first moving carrier member is illustrated, in accordance with various non-limiting embodiments;

FIG. 37 is a top view of zones of the portion of the transfer member of FIG. 36 with the portion of the transfer member in the second position in accordance with one non-limiting embodiment.

DETAILED DESCRIPTION

Figure 1:
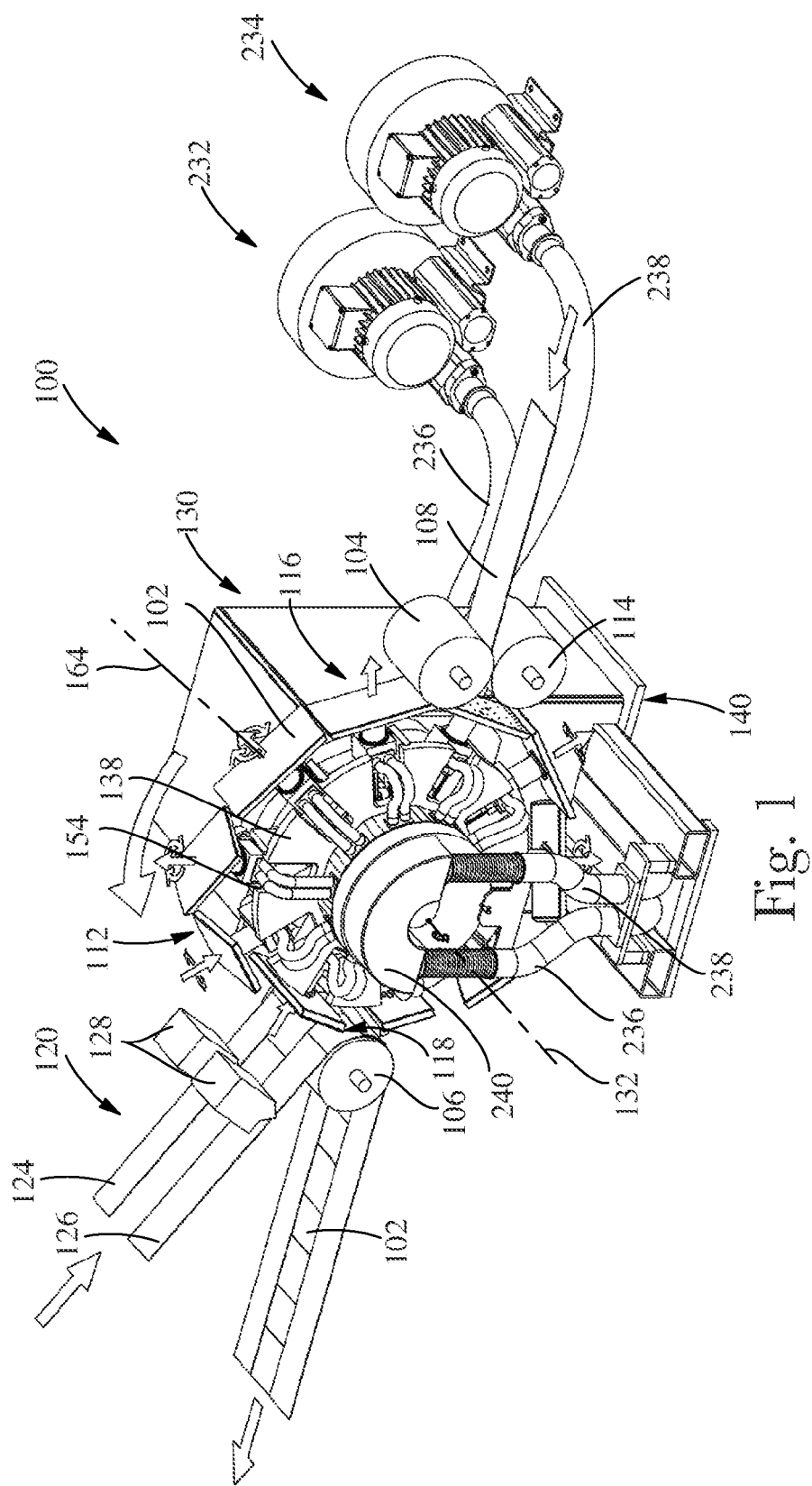
FIG. 1 is a front perspective view of a transfer assembly configured to transfer a discrete article from a first moving carrier member to a second moving carrier member in accordance with one non-limiting embodiment.

Various non-limiting embodiments of the present disclosure will now be described to provide an overall understanding of the principles of the structure, function, manufacture, and use of the methods for transferring discrete articles disclosed herein. One or more examples of these non-limiting embodiments are illustrated in the accompanying drawings. Those of ordinary skill in the art will understand that the methods for transferring discrete articles described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

The term "absorbent article(s)" is used herein to refer to consumer products whose primary function is to absorb and retain bodily exudates and wastes. Absorbent articles as used herein may refer to pants, taped diapers, and/or sanitary napkins (e.g., feminine hygiene products). In some instances, absorbent articles may comprise or be formed into pants, taped diapers, or sanitary napkins. The terms "diaper" and "pants" are used herein to refer to absorbent articles generally worn by infants, children, and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted, or otherwise disposed of in an environmentally compatible manner).

The term "nonwoven" or "nonwoven material" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the primary direction of material, web, or article flow through a process. In various manufacturing and converting processes, such as a bi-fold process, it may be possible to have more than one machine direction when an article is undergoing simultaneous processes. In other words, a manufacturing line may have an overall machine direction, but a material or an article may travel in directions other than the overall machine direction as it passes through various processes along the manufacturing line. For example, a discrete article having a trailing end portion and a leading end portion, each portion being attached to the surface of a different roll and/or conveyor may travel in two different directions simultaneously. In this example, both directions of travel may be considered the machine direction.

The term "cross direction" (CD) is used herein to refer to a direction that is generally perpendicular to the machine direction.

The term "taped diaper" refers to disposable absorbent articles having an initial front waist region and an initial rear waist region that are not fastened, pre-fastened, or connected to each other as packaged, prior to being applied to the wearer. A taped diaper may be folded about its lateral central axis with the interior of one waist region in surface to surface contact with the interior of the opposing waist region without fastening or joining the waist regions together. Example taped diapers disclosed in various suitable configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

The term "pant" refers herein to disposable absorbent articles having a continuous perimeter waist opening and continuous perimeter leg openings designed for infant, child, or adult wearers. A pant may be configured with a continuous or closed waist opening and at least one continuous, closed, leg opening prior to the article being applied to the wearer. A pant may be preformed by various techniques including, but not limited to, joining together portions of the absorbent article using any refastenable and/or permanent closure member (e.g., seams, heat bonds, pressure welds, adhesives, cohesive bonds, mechanical fasteners, etc.). A pant may be preformed anywhere along the circumference of the absorbent article in the waist region (e.g., side fastened or seamed, front waist fastened or seamed, rear waist fastened or seamed). A pant may be opened about one or both of the side seams and then refastened. Example pants in various configurations are disclosed in U.S. Pat. Nos. 5,246,433, 5,569,234, 6,120,487, 6,120,489, 4,940,464, 5,092,861, 5,897,545, 5,957,908, and U.S. Patent Publication No. 2003/0233082.

The term "discrete articles" refers herein to absorbent articles, pants, taped diapers, sanitary napkins, bandages, medical pads and dressings, and any other suitable articles, in any industry, capable of being transferred using the transfer apparatuses of the present disclosure. Discrete articles may also refer herein to portions of the absorbent articles, pants, taped diapers, sanitary napkins, bandages, medical pads and dressings, and other suitable articles. The discrete articles may be flexible. In one example, discrete articles may refer herein to a chassis of a taped diaper or a pant. The chassis may comprise a topsheet, a backsheet, and an absorbent core disposed between at least a portion of the topsheet and the backsheet. The chassis may also comprise stretched elastic elements such as leg elastics and inner barrier leg cuff elastics, for example.

In various embodiments, referring to FIG. 1, the present disclosure provides, in part, transfer assemblies (e.g., 100) and transfer members associated with the transfer assemblies for transferring discrete articles and/or flexible discrete articles, such as a chassis of a pant or a taped diaper, for example. The present disclosure also provides, in part, methods for transferring the discrete articles. A chassis of a pant or a taped diaper, for example, may be traveling at a first speed on a first moving carrier member and may be transferred by the transfer members, or portions thereof, of the transfer assemblies to a second moving carrier member traveling at a second speed or at the same speed. The discrete articles may be transferred onto the second moving carrier member to change the speed and/or pitch of the discrete articles and/or to turn the discrete articles, for example. In other embodiments, components, such as webs of front and rear belts or discrete front and rear belts, either of which are configured to together form a portion of a belt in a pant, for example, may be moving over the second moving carrier member. The second moving carrier member may have a first portion carrying the web of front belts and a second portion carrying a web of rear belts. In other embodiments, the second carrier member may comprise two separate moving carrier members; one carrying the web of front belts and the other carrying the web of rear belts. If webs of front and rear belts are provided on the second moving carrier member, the chassis may be transferred from the first moving carrier member to the second moving carrier member and turned so as to apply the waist regions of the chassis to the first and second webs of front and rear belts. A first waist region of the chassis may be applied to the web of first belts and a second waist region of the chassis may be applied to the web of second belts to form an absorbent article that can be formed into a pant or a taped diaper, for example. The waist regions of the chassis may be glued to the webs of belts or otherwise attached to the webs of belts. Further details regarding this example transfer are provided herein.

The transfer assemblies and portions of transfer members of the present disclosure may be able to turn the discrete articles intermediate the first moving carrier member and the second moving carrier member for placement onto one or more webs of components or discrete components traveling over the second moving carrier member or onto the second moving carrier member without being placed on discrete components. In one example, a portion of a transfer member of a transfer assembly may receive a discrete article, such as a taped diaper or pant chassis, for example, from a first moving carrier member and turn it between a first position and a second position (e.g., a 90 degree turn to the discrete article) and apply the discrete article onto webs of front and rear belts traveling on the second moving carrier member to form an absorbent article that can be formed into a taped diaper or a pant. The transfer assemblies and transfer members, or portions thereof, may also be configured to repitch the discrete articles between the first moving carrier member and the second moving carrier member. This "repitching" is changing the spacing between midpoints of the discrete articles relative to each other. In one embodiment, the pitch may be smaller or larger once deposited onto the second moving carrier member compared to when the discrete articles were situated on the first moving carrier member. In other embodiments, the pitch of the discrete articles may not be changed between the first moving carrier member and the second moving carrier member. In various embodiments, the transfer assemblies and portions of the transfer members of the present disclosure may not turn the discrete articles between the first and second moving carrier members, although they may have the ability to do so. In other embodiments, the transfer assemblies and/or transfer members, or portions thereof, may not have the ability to turn the discrete articles during a transfer between the first and second moving carrier members.

It is to be appreciated that the methods and apparatuses of the present disclosure may also be suitable for any other uses that require transfer of a discrete article or a discrete component from a first moving carrier member to a second moving carrier member regardless of the speed of the first and second moving carrier members and regardless of whether the discrete articles or discrete components need to be turned and/or repitched. These other uses may comprise various manufacturing processes for any product, or intermediate product, in any industry.

Figure 2:
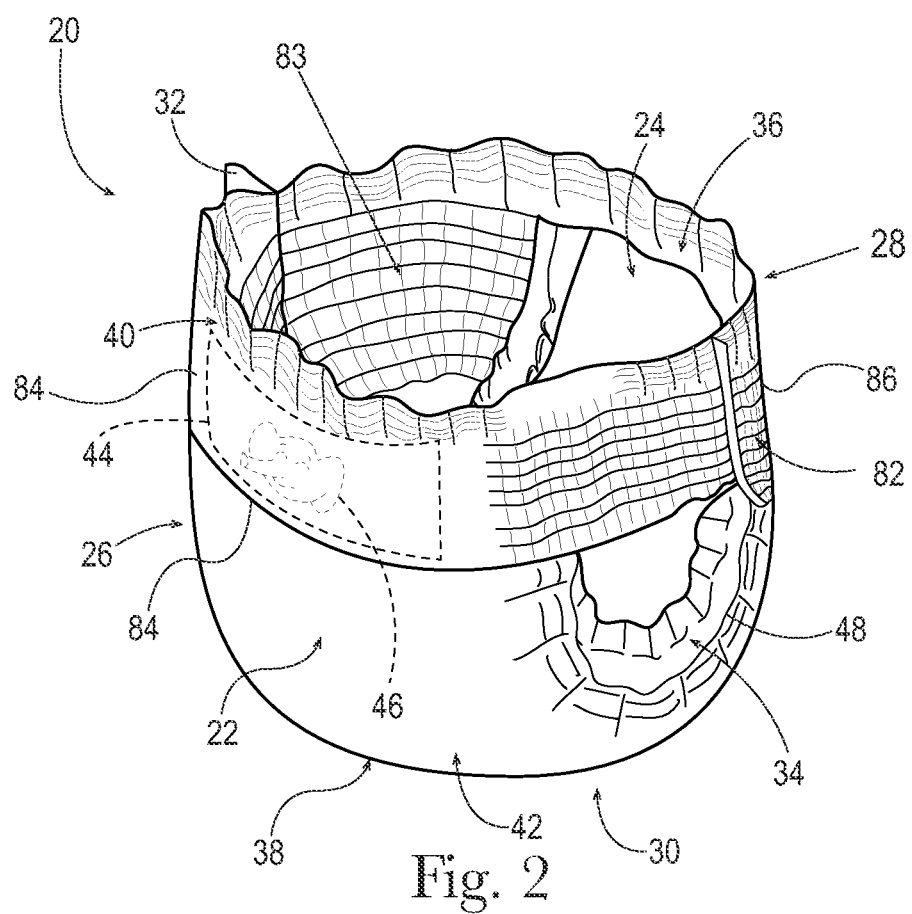
FIG. 2 is a perspective view of a pant in accordance with one non-limiting embodiment.
Figure 3:
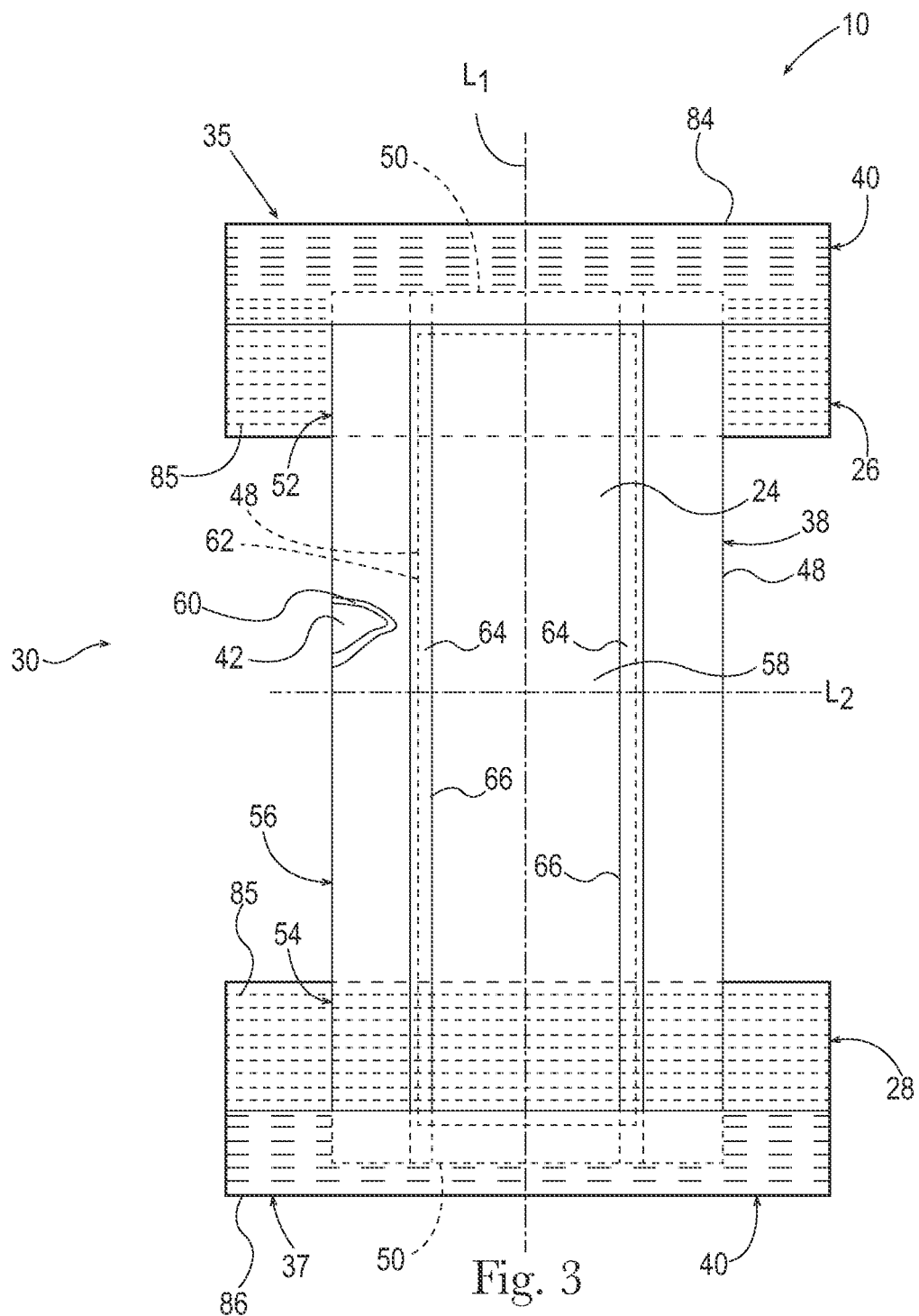
FIG. 3 is a schematic illustration of an absorbent article capable of being formed into the pant of FIG. 2 in accordance with one non-limiting embodiment.

In one embodiment, FIG. 2 illustrates an example of a pant 20 that may be at least partially formed or manufactured using the transfer assemblies and transfer members of the present disclosure. FIG. 3 illustrates an absorbent article 10 that can be formed into the pant 20 of FIG. 2. Those of skill in the art will recognize that FIGS. 2 and 3 are merely examples of one product that may be formed, or at least partially manufactured, using the transfer assemblies and transfer members of the present disclosure. Many other products, including other absorbent articles, pants, or portions thereof, may be formed, or at least partially manufactured, using the transfer assemblies and transfer members of the present disclosure. The absorbent article 10 has a longitudinal central axis L1 and a lateral central axis L2 (see FIG. 3). The pant 20 has an outer surface 22, an inner surface 24 opposed to the outer surface 22, a front waist region 26, a rear waist region 28, a crotch region 30, and seams 32 which join the front waist region 26 and the rear waist region 28 to form two leg openings 34 and a waist opening 36. The seams 32 may be permanent or refastenable. When referring to "pant 20" herein, it will be understood that the absorbent article 10, although not yet formed into the pant 20, may be considered a "pant". It will be understood that the pant 20 is disclosed as an example, but that a taped diaper may also be formed from the absorbent article 10 merely by adding fastening elements and/or landing zones to one or both of the front and rear belts 84 and 86.

In one embodiment, referring to FIGS. 2 and 3, the pant 20 may comprise an absorbent chassis 38 to cover a crotch region of a wearer and a belt 40 extending transversely about the waist opening 36. The pant 20 may also optionally comprise an outer cover layer 42 to cover the chassis 38. The belt 40 may define the waist opening 36 in the pant 20. The belt 40, the chassis 38, and/or the outer cover layer 42 may jointly define the leg openings 34. In one embodiment, the pant 20 may have a patch sheet 44 printed with a graphic 46 thereon, which may be disposed in the front waist region 26, the rear waist region 28, or any other suitable portion of the pant 20. The belt 40 may be formed from a front belt 84 in the front waist region 26 and a rear belt 86 in the rear waist region 28. The front belt 84 may form a front waist edge 35 in the front waist region 26 and the rear belt 86 may form a rear waist edge 37 in the rear waist region 28. The front and rear waist edges 35 and 37 may be laterally opposed about the lateral central axis L2. The belt 40 may form a portion of an outer surface 22 or an inner surface 24 of the pant 20. In other embodiments, the belt 40, or portions thereof, may be disposed intermediate other layers of the chassis 38, such as a topsheet and a backsheet, for example.

The absorbent chassis 38 may absorb and contain body exudates or wastes disposed on the chassis 38. Referring to FIG. 3, the chassis 38 may have a generally rectangular shape having left and right longitudinally extending side edges 48 (hereinafter may be referred to as "longitudinal side edge") and front and rear laterally extending end edges 50 (hereinafter may be referred to as "lateral end edge"). The chassis 38 may also comprise waist panels (i.e., a front waist panel 52 positioned in the front waist region 26 and a rear waist panel 54 positioned in the rear waist region 28) and a crotch panel 56 in the crotch region 30 between the front and rear waist panels 52, 54.

In one embodiment, referring to FIG. 3, the pant 20 may comprise front and rear belts 84 and 86 intended to encircle at least a portion of the waist of the wearer. The front and rear belts 84 and 86 together form at least a portion of, or all of, the belt 40 when joined. The front and rear belts 84 and 86 may be connected by the chassis 38 forming the crotch region 30 of the pant 20. The front and rear belts 84 and 86 may each be formed from a first belt layer 82 possibly forming a portion of the outer surface 22 of the pant 20 and a second belt layer 83 possibly forming a portion of the inner surface 24 of the pant 20. The first and second belt layers 82 and 83 may be comprised of any known materials. Various suitable materials may comprise films, plastic films, apertured plastic films, woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers, stretchable nonwovens, or coated woven or nonwoven webs. The belt 40 may comprise an inner hydrophobic, nonwoven material and an outer hydrophobic, nonwoven material. The front and rear belts 84 and 86 may also comprise a plurality of elastic elements 85 disposed at least partially between the first and second belt layers 82 and 83 thereof and attached to at least one of the first and second belt layers 82 and 83 using adhesives or bonding, for example. The elastic elements 85 may comprise one or more elastic strands, elastic materials, elastomeric films, elastomeric ribbons, elastomeric nonwovens, elastomeric filaments, elastomeric adhesives, elastomeric foams, scrims, or combinations thereof.

The chassis 38 of the pant 20 may comprise a portion of the outer surface 22, a backsheet 60, a portion of the inner surface 24, a topsheet 58, and an absorbent core 62 disposed between at least a portion of the topsheet 58 and the backsheet 60. In addition, the chassis 38 may comprise elasticized barrier leg cuffs 64 disposed at or adjacent the side edges 48 of the chassis 38. The barrier leg cuffs 64 may provide improved containment of liquids and other body exudates or wastes in the crotch region 30 and may comprise a single layer of material which may be folded to form a barrier leg cuff having two layers. The barrier leg cuffs 64 may extend from the side of the chassis 38 at or adjacent the longitudinal side edge 48 toward the longitudinal central axis L1. The barrier leg cuffs 64 may be folded along the folding lines 66 back toward the longitudinal side edges 48. The front and rear belts 84 and 86 may overlap at least a portion of the chassis 38 and one or both of the front and rear belts 84 and 86 may be disposed on the outer surface 22 of the chassis 38, on the inner surface 24 of the chassis 38, or disposed intermediate various portions of the chassis 38.

In one embodiment, a portion of, or the whole of, the chassis 38 may be made extensible to a degree greater than the inherent extensibility of the material or materials from which the chassis 38 is made, e.g., the backsheet 60. The additional extensibility may be desirable in order to allow the chassis 38 to conform to the body of a wearer during movement by the wearer and or to provide adequate body coverage. The additional extensibility may also be desirable, for example, in order to allow the user of a pant including the chassis 38 having a particular size before extension to extend the front waist region 26, the rear waist region 28, or both of the waist regions of the chassis 38 to provide additional body coverage for wearers of differing size, i.e., to tailor the pant to the individual wearer. Such extension of the waist region or regions may give the chassis 38 a generally hourglass shape, so long as the crotch region 30 is extended to a relatively lesser degree than the waist region or regions, and may impart a tailored appearance to the pant 20 when it is donned or worn. In addition, the additional extensibility may be desirable in order to minimize the cost of the pant 20. For example, an amount of material that would otherwise be sufficient only to make a relatively smaller pant lacking this extensibility may be used to make an article capable of being extended to adequately cover a wearer that is larger than the unextended smaller pant would fit.

A portion of the chassis 38, for example, a portion of the chassis 38 in one or both of the waist regions 26 and 28 may be made laterally extensible to a maximum extensibility greater than a maximum extensibility of another portion of the chassis 38 in the crotch region 30 such that a lateral extension of each of the portions to its maximum extensibility imparts an hourglass shape to the chassis 38. In one embodiment, the portion of the chassis 38 underlying, overlying, and/or immediately adjacent one or both of the front and rear extensible belts 84 and 86 may be made laterally extensible to a maximum extensibility greater than a maximum extensibility of another portion of the chassis 38, for example the crotch region 30, such that a lateral extension of each of the portions to its maximum extensibility facilitates application of the pant 20 onto the body of a wearer by enabling the waist regions 26 and 28 to be extended to fit over the wearer's hips and in addition, opening and orienting the leg openings enabling the wearer to place the legs through the openings more effectively.

In one embodiment, the liquid pervious topsheet 58 may be positioned adjacent the body-facing surface of the absorbent core 62 and may be joined thereto and/or to the backsheet 60 by any attachment means known to those of skill in the art. The liquid impervious backsheet 60 may generally be that portion of the pant 20 positioned adjacent the garment-facing surface of the absorbent core 62 and may prevent, or at least inhibit, the bodily exudates and wastes absorbed and contained in the absorbent core 62 from soiling garments that may contact the outer surface 22 of the pant 20.

The topsheet 58, the backsheet 60, and the absorbent core 62 may be manufactured of any known materials. Suitable topsheet materials may comprise porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the pant 20 while still preventing, or at least inhibiting, bodily exudates or wastes from passing through the backsheet 60. Such materials may include nonwoven materials, woven materials, films, and/or laminates comprising a combination of one or more of these materials. In one embodiment, the backsheet 60 may be a film and nonwoven laminate, wherein the nonwoven of the laminate forms the outer cover layer 42.

A suitable absorbent core 62 for use in the pant 20 may comprise any absorbent material which is generally compressible, conformable, non-irritating to the wearer's skin, and capable of absorbing and retaining liquids such as urine and other certain body exudates. In addition, the configuration and construction of the absorbent core 62 may also be varied (e.g., the absorbent core(s) or other absorbent structure (s) may have varying caliper zones, hydrophilic gradient(s), a superabsorbent gradient(s), or lower average density and lower average basis weight acquisition zones; or may comprise one or more layers or structures). In some embodiments, the absorbent core 62 may comprise a fluid acquisition component, a fluid distribution component, and/or a fluid storage component. An example of a suitable absorbent core having a fluid acquisition component, a fluid distribution component, and a fluid storage component is described in U.S. Pat. No. 6,590,136.

In one embodiment, the outer cover layer 42 may be disposed on the outer surface 22 of the pant 20 and may cover the crotch panel 56 of the absorbent chassis 38. The outer cover layer 42 may extend into and cover the front waist panel 52 and the rear waist panel 54 of the chassis 38. The outer cover layer 42 may form a portion of the backsheet 60 and/or the chassis 38. In one embodiment, the outer cover layer 42 may be directly joined to and cover a portion of, or all of, the liquid impervious backsheet 60 of the chassis 38. In various embodiments, the outer cover layer 42 may be disposed between the front and rear belts 84 and 86.

The outer cover layer 42 may comprise a material separate from the first and second belt layers 82 and 83 forming the belts 84 and 86. The outer cover layer 42 may comprise two or more layers of materials of any known materials including the materials used for the first and second belt layers 82 and 83. In one embodiment, the outer cover layer 42 may comprise a single layer of a nonwoven web of synthetic fibers. In various embodiments, the outer cover layer 42 may comprise a single layer of hydrophobic, non-stretchable nonwoven material. In one embodiment, the outer cover layer 42 may comprise a film, a foam, a nonwoven, a woven material, or the like and/or combinations thereof such as a laminate of a film and a nonwoven.

In one embodiment, the belt 40 may be at least partially formed, or fully formed, when the front and rear belts 84 and 86 are permanently or refastenably connecting together to form the seams 32. Any suitable seams may be formed, as known to those of skill in the art. The belt 40 may be ring-like and elastic. The ring-like elastic belt 40 may extend about the waist opening 36 of the pant 20 and act to dynamically create fitment forces and to distribute the forces dynamically generated during wear.

Figure 4:
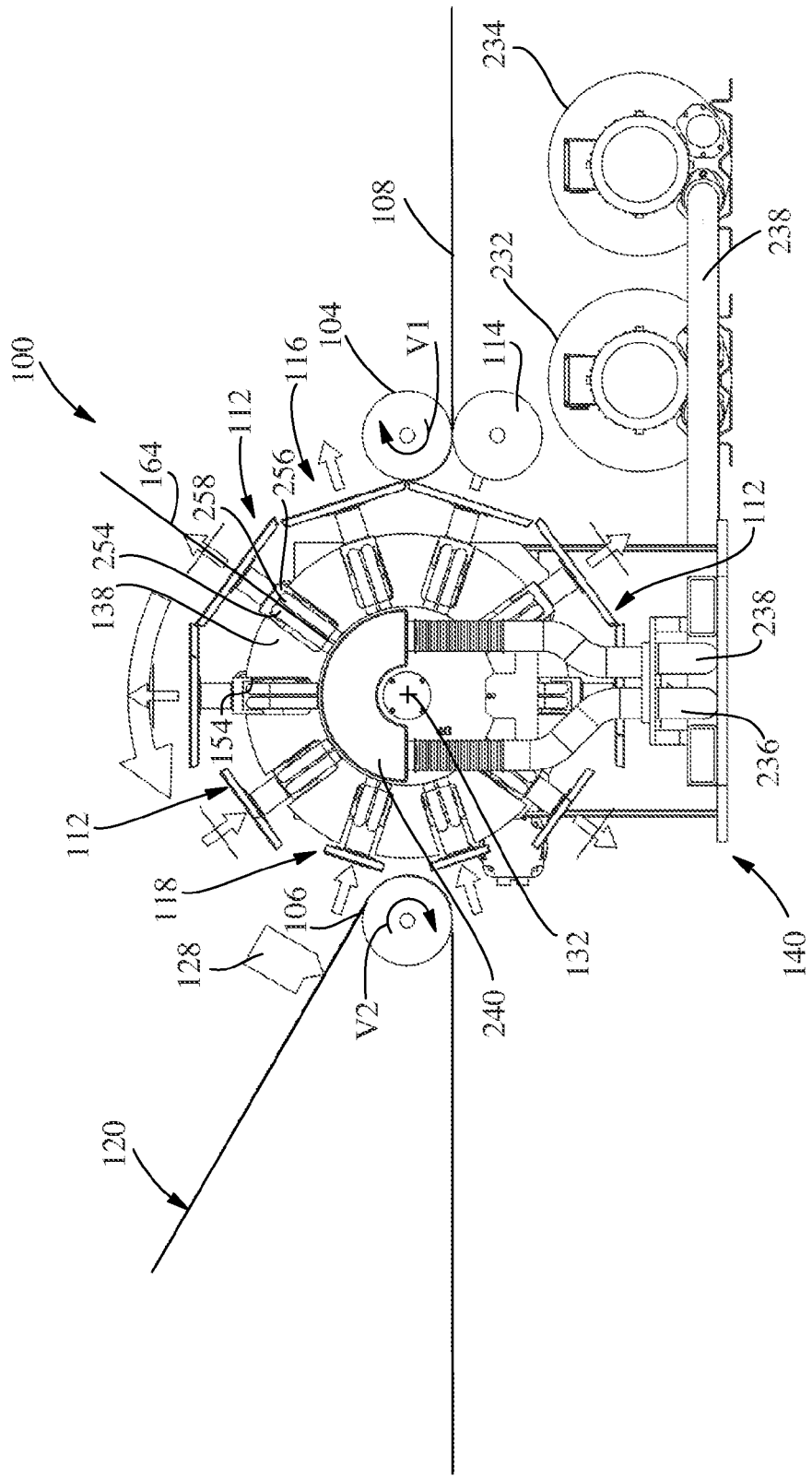
FIG. 4 is a front view of the transfer assembly of FIG. 1 in accordance with one non-limiting embodiment.
Figure 5:
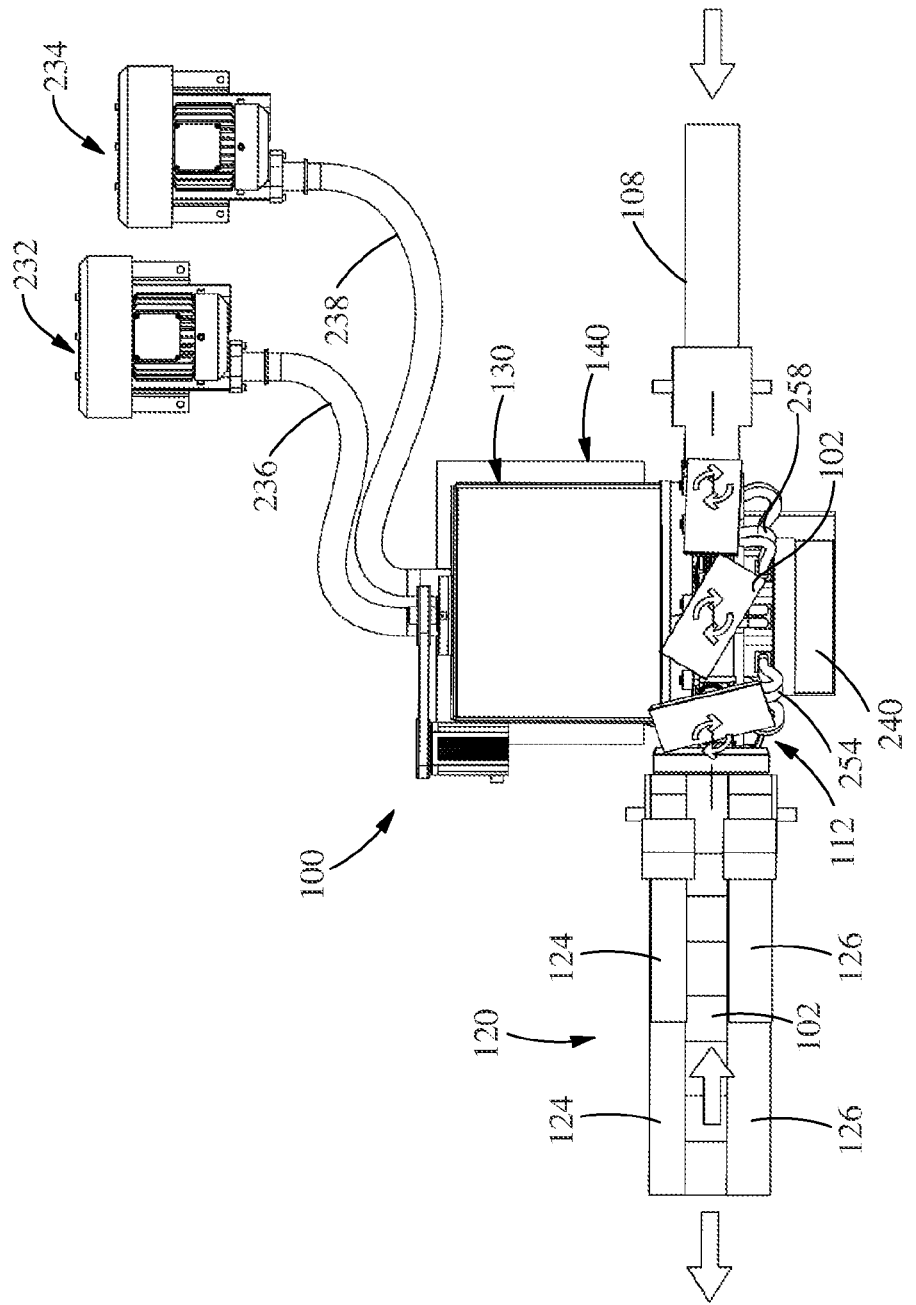
FIG. 5 is a top view of the transfer assembly of FIG. 1 in accordance with one non-limiting embodiment.
Figure 6:
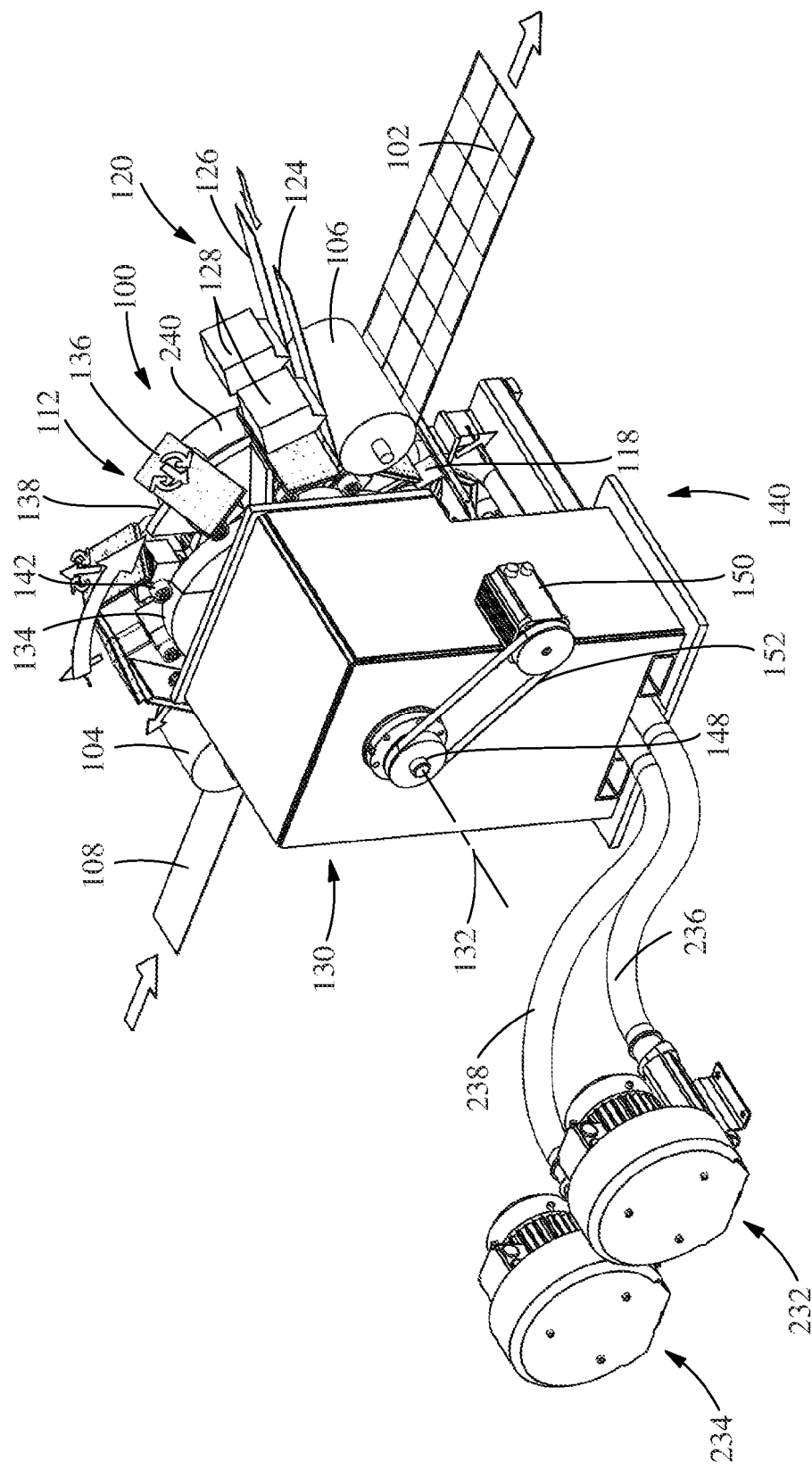
FIG. 6 is a rear perspective view of the transfer assembly of FIG. 1 in accordance with one non-limiting embodiment.

In one embodiment, referring to FIGS. 1 and 4-6, a transfer assembly 100 for transferring discrete articles from or to a moving carrier member is illustrated. FIG. 1 is a front perspective view of the transfer assembly 100. FIG. 4 is a front view of the transfer assembly 100. FIG. 5 is a top view of the transfer assembly 100. FIG. 6 is a rear perspective view of the transfer assembly 100. The transfer assembly 100 may transfer the discrete articles 102 from a first moving carrier member 104 to a second moving carrier member 106. The moving carrier members 104 and 106 from and to which the discrete articles 102 are transferred may be rolls, drums, curved conveyors, linear conveyors, and/or discrete heads following a curvilinear path, for example. The first and second moving carrier members 104 and 106 may be moving at a different surface velocity or at the same surface velocity. The transfer assembly 100 may pick up the discrete article 102 at a first velocity, V1, from the first moving carrier member 104 and may apply the discrete article 102 at a second velocity, V2, to the second moving carrier member 106. The first velocity, V1, and the second velocity, V2, at the point or zone of discrete article transfer to and from the first and second moving carrier members 104 and 106 may be tangential or linear velocities.

In one embodiment, a continuous web of articles 108 may be fed on a roll or other conveying mechanism toward the first moving carrier member 104. Once a portion of the web of discrete articles 108 long enough to form a discrete article 102 is engaged with the first moving carrier member 104 and/or is engaged with a portion of a transfer member 112 of the transfer assembly 100, a knife integral to the first moving carrier member 104 may cut the web 108 into discrete articles 102 against an anvil roll 114. The knife may be a flex knife, a die cutter, a shear knife, or any other suitable knife or cutting device or mechanism. Knife and anvil roll technology is generally known in the art. In other embodiments, previously cut discrete articles 102 may be fed on the conveyor toward the first moving carrier member 104.

Portions of the transfer members 112 of the present disclosure may also turn between a first position 116 and at least a second position 118 when transferring the discrete articles 102 between the first and second moving carrier members 104 and 106. As a result, the discrete articles 102 may be turned between a first position 116 and a second position 118. The portions of the transfer members 112 may be turned using rotation assemblies engaged with a portion of each transfer member 112, as described in further detail below. The discrete articles 102 may be turned between 30 and 180 degrees, between 40 and 150 degrees, between 60 and 120 degrees, between 75 and 105 degrees, 45 degrees, about 90 degrees (e.g., +/−5 degrees), 90 degrees, and 180 degrees, specifically reciting each degree within the above-recited ranges. Optionally, the discrete articles 102 may also not be turned at all and the transfer assembly may be used for conveying and/or repitching the discrete articles 102 without turning them.

Again referring to FIGS. 1 and 4-6, continuous webs of components 120 may be moving towards, over, and away from the second moving carrier member 106 on a roller, conveyor, or other mechanism. In one example, these webs of components 120 may be front belts 124 and rear belts 126, although in other embodiments, the webs of components 120 may be various other components or even discrete components that have been previously cut from a continuous web. An adhesive may be applied to the webs of components 120 or discrete components using adhesive dispensers 128. The adhesive dispensers 128 are optional and are used to illustrate one example use of the transfer assemblies 100 of the present disclosure. The adhesive may be applied to portions of the webs of components 120 prior to those portions being moved over the second moving carrier member 106. As a result, a discrete article 102 being transferred to the second moving carrier member 106 may be adhesively attached to the webs of components 120 when transferred onto the second moving carrier member 106. In one example, the discrete article 102 may be a chassis 38 and the front waist panel 52 of the chassis 38 may be adhesively attached to the continuous web of front belts 124 and the rear waist panel 54 of the chassis 38 may be adhesively attached to the continuous web of rear belts 126. This may form a web of absorbent articles 10. The web of absorbent articles 10 may then be cut or separated into discrete absorbent articles 10, such as the absorbent article of FIG. 2.

Figure 7:
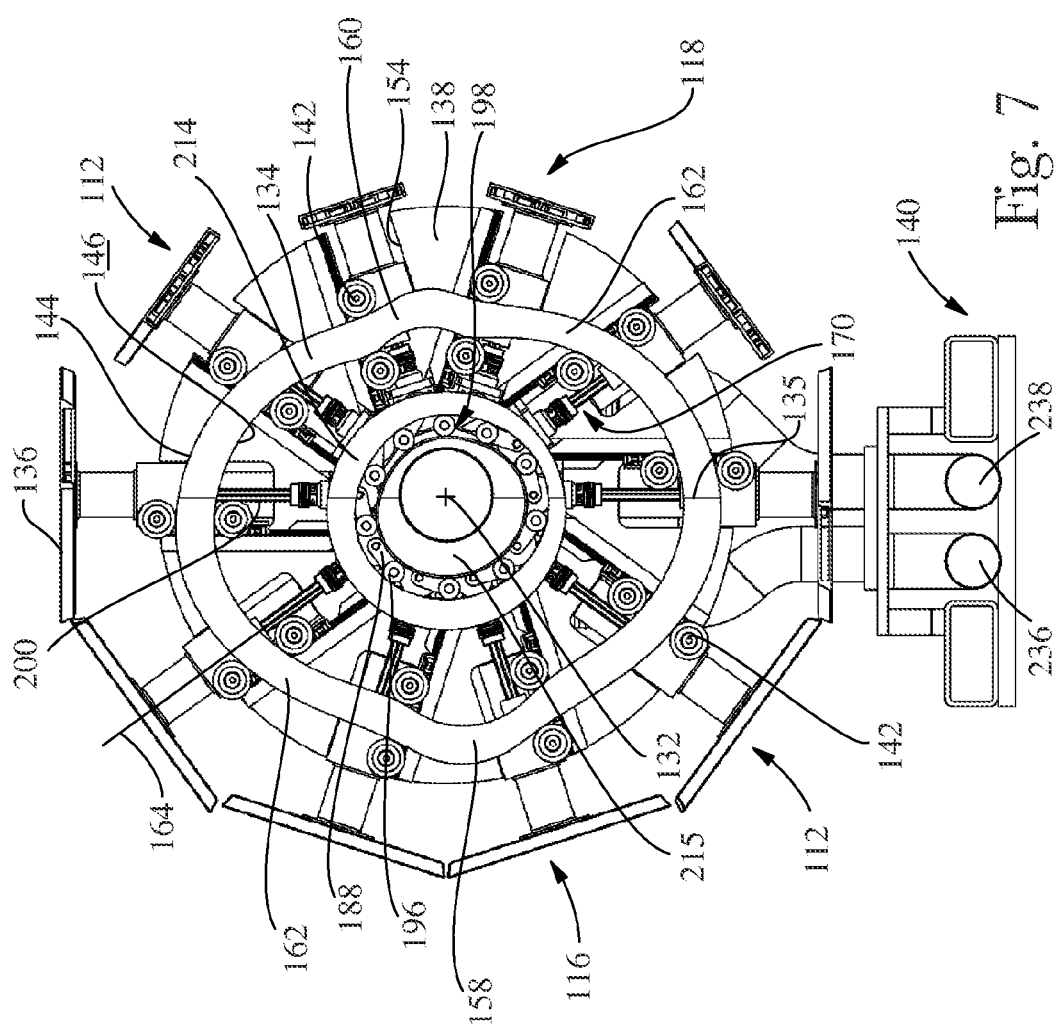
FIG. 7 is a rear view of a portion of the transfer assembly of FIG. 1 in accordance with one non-limiting embodiment.
Figure 8:
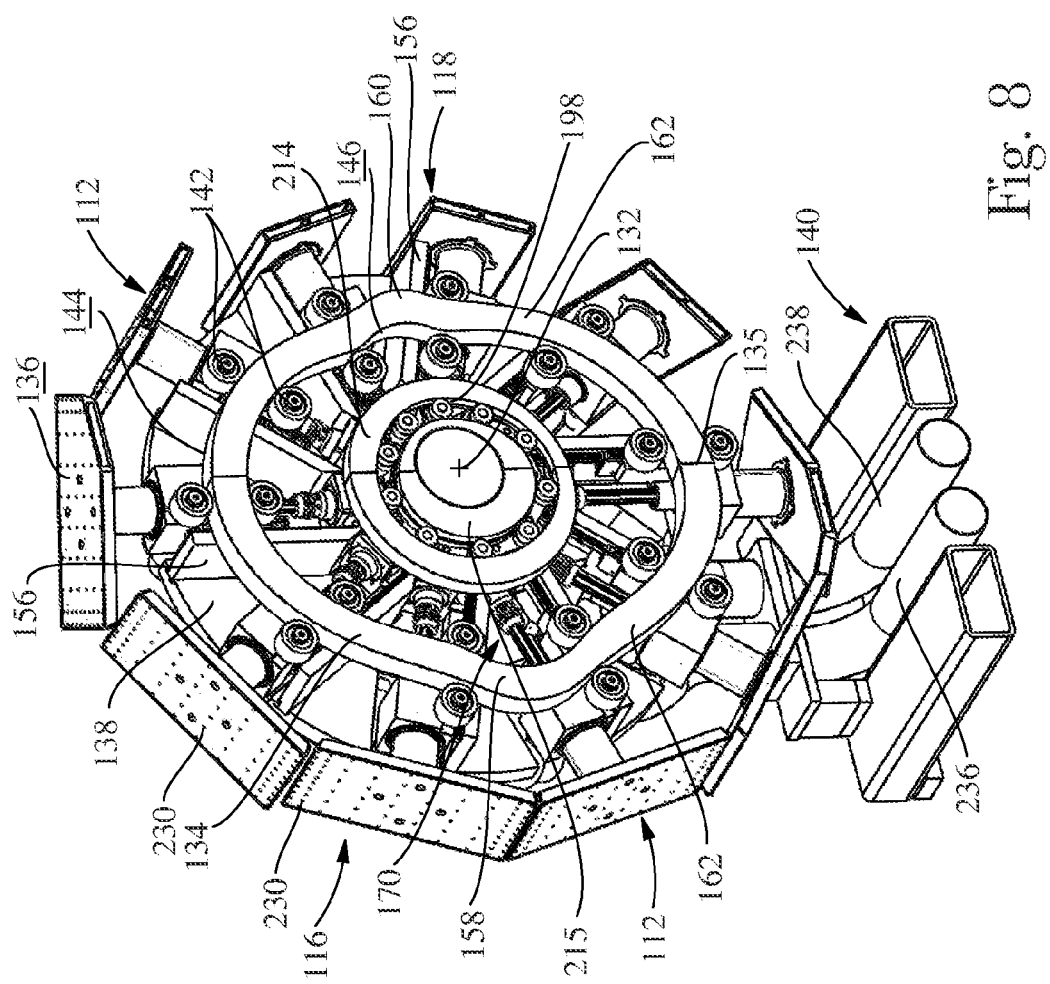
FIG. 8 is a rear perspective view of a portion of the transfer assembly of FIG. 1 in accordance with one non-limiting embodiment.
Figure 9:
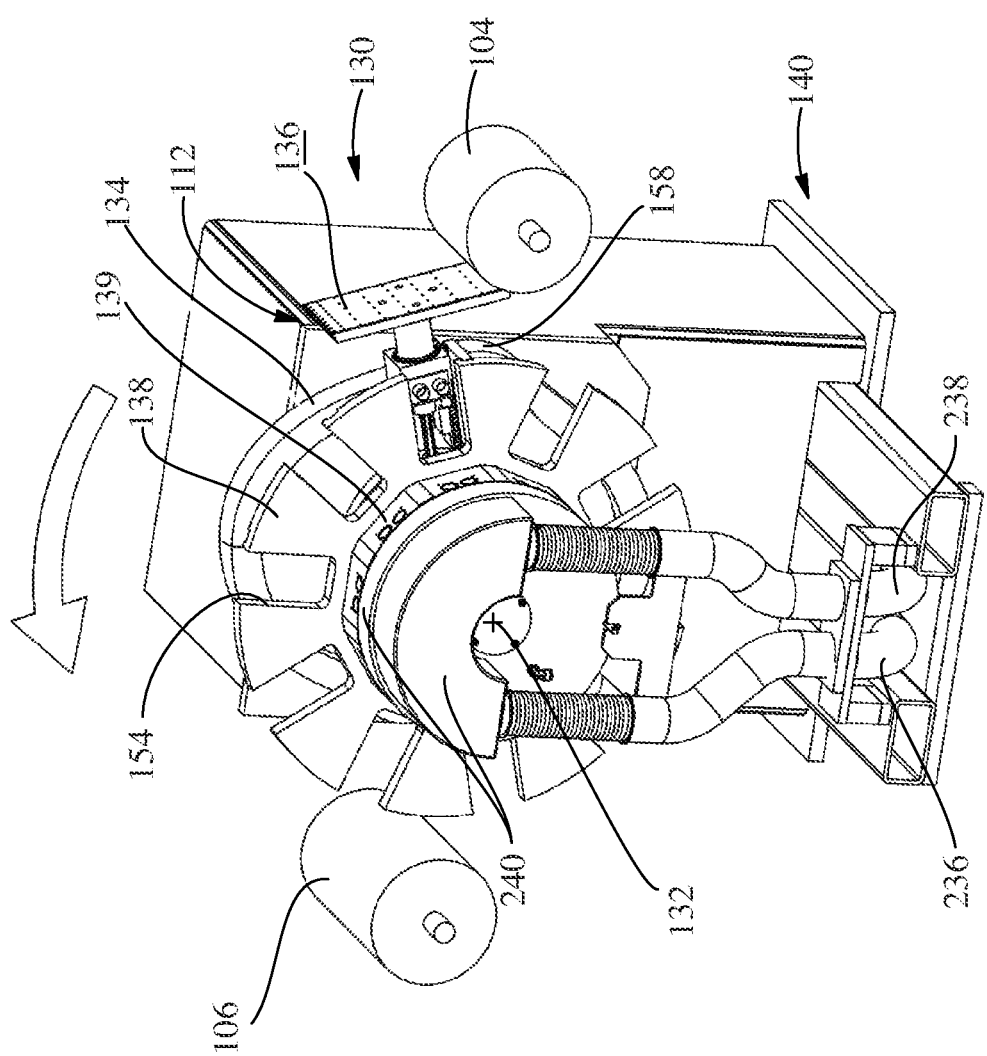
FIG. 9 is a simplified front perspective view a transfer assembly for transferring discrete articles in accordance with one non-limiting embodiment.
Figure 10:
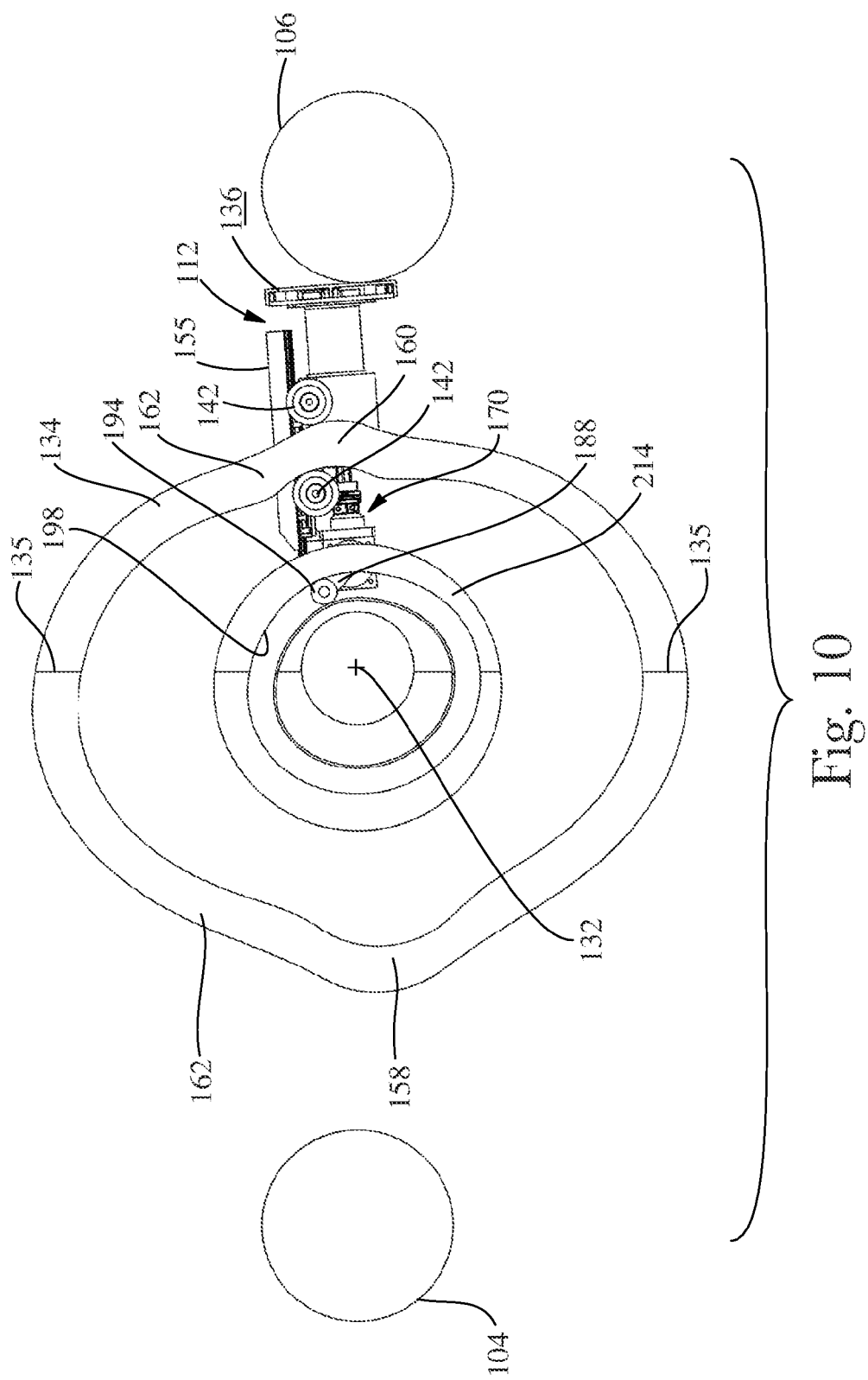
FIG. 10 is a rear view of two tracks and a transfer member and rotation assembly movably engaged with the two tracks in accordance with one non-limiting embodiment.

In one embodiment, referring to FIGS. 1 and 4-10, the transfer assembly 100 may comprise a frame 130 defining a rotation axis 132 and a track 134 (also referred to herein as a first track or the outer track) having a circumferential shape surrounding the rotation axis 132. FIG. 7 is a partial rear perspective cross-sectional view of the transfer assembly 100 and FIG. 8 is a partial rear perspective cross-sectional view of the transfer assembly 100. In both of FIGS. 7 and 8, the frame 130 and various other components have been removed to more clearly illustrate various features. FIG. 9 is a front perspective view of the transfer assembly 100 with multiple transfer members 112 removed for clarity in illustration. FIG. 10 is a rear view of portions of the transfer assembly 100 illustrating the track 134, the transfer member 112, and other components for clarity. The distance between the rotation axis 132 and various points on the track 134 may vary. The track 134 may be a cam track. The track 134 may comprise one or more separation points 135 in the event the track 134 needs to be disassembled for maintenance or other reasons. The transfer assembly 100 may comprise one or more transfer members 112 movably, rollably, and/or slidably engaged with the track 134. Each transfer member 112 may comprise a transfer surface 136 on an end of the transfer member 112 most distal from the rotation axis 132. The transfer surface 136 may be configured to receive one or more of the discrete articles 102. In various embodiments, the transfer surfaces 136 of the transfer members 112 may be configured to retain the discrete articles 102 thereto using a fluid pressure, magnets, or an adhesive, for example. The transfer assembly 100 may also comprise a wheel 138 supported by the frame 130 and configured to rotate about the rotation axis 132. The wheel 138 may or may not be round about its perimeter. The wheel 138 may be engaged with portions of the transfer members 112 such that as the wheel 138 rotates about the rotation axis 132, the transfer members 112 circumnavigate about a path about the rotation axis 132 in correspondence with the track 134. The shape of the track 134 may cause the transfer members 112 to move radially inwardly and radially outwardly relative to the rotation axis 132 while the transfer surfaces 136 are maintained a constant or a substantially constant distance or minimum distance away from the first and second moving carrier members 104 and 106 at the point or zone of discrete article transfer onto and off of the transfer surfaces 136. In other embodiments, the minimum distance may vary typically from 0-6 mm or may have a tolerance of typically +/−0.1 to 1 mm, although a wide range of targets are achievable. In one embodiment, the minimum distance may be constant, then not constant, then constant again at the point or zone of discrete article transfer as the transfer surface 136 is moved past the point or zone of discrete article transfer. Such a profile may be employed if, for instance, it is desired to only maintain the substantially constant gap at the leading and/or trailing edge of the transfer. The profile may also be adjusted to account for thickness variations in the discrete article being transferred. In one embodiment, the gap may be profiled to be larger in the region with the absorbent core, for example.

In one embodiment, referring again to FIGS. 1 and 4-10, the frame 130 may be mounted to a base or stand 140 for the transfer assembly 100. The track 134 may be formed with or in the frame 130 or be mounted to the frame 130. The track 134 may be a projection that extends from a plane of the frame 130 or may be a groove (not illustrated) defined in the frame 130. The track 134 may have a constant, or substantially constant, width, or a varying width, regardless of whether it is a projection or a groove. In the event the track 134 is a groove, a follower member 142 extending from each of the one or more transfer members 112 may be movably, slidably, and/or rollably engaged with the groove. The follower member 142 may be biased toward the track 134. In the event the track 134 is a projection as illustrated, a follower member 142 extending from each of the one or more transfer members 112, or portions thereof may be movably, slidably, and/or rollably engaged with a surface of the projection that extends generally perpendicular to a front planer surface of the frame 130 from which the projection extends. In one embodiment, when the track 134 is a projection, two or more follower members 142 may extend from each transfer member 112, or portions thereof, such that one follower member 142 engages a first surface 144 of the projection and another follower member 142 engages the opposite surface 146 of the projection. The follower members 142 may be rollers or cam followers that slide or roll about the track 134 as the transfer member 112 circumnavigates about a path around the rotation axis 132. In one embodiment, the follower members 142 may comprise materials such as metals, plastics, and/or polymers, for example, or coatings thereof, to permit rolling or sliding movement between the follower members 142 and the track 134.

In the event that the track 134 is a groove, the follower members 142 may comprise two stacked concentric cylindrical cam followers, each following one side of the groove. This may constrain the cam followers to rotate in one direction and eliminate, or at least inhibit, the issue of cam follower reversal as with a single cam follower following a groove. The stacked cam followers may also be configured with eccentricity between the axes of their rotation. Adjusting the eccentric may adjust the clearance between the cam groove and the cam followers. An elastic element, such as a spring or pneumatic cylinder, for example, may also be used to keep the cam follower loaded against one surface of the groove. This has the potential to only use one surface of the groove.

In the event that the track 134 is a projection, the follower members 142 may comprise two conjugate cylindrical follower members on each side of the track projection 134. This arrangement may naturally cause each follower member to rotate in one direction. The axis of rotation of one of the follower members may be adjusted to control the clearance between the follower members and the track projection 134. A single follower member may be employed in conjunction with an elastic or inertial force to keep the follower member in contact with the track projection 134. The follower member may be spring loaded or loaded by pneumatic cylinder, for example.

Figure 16:
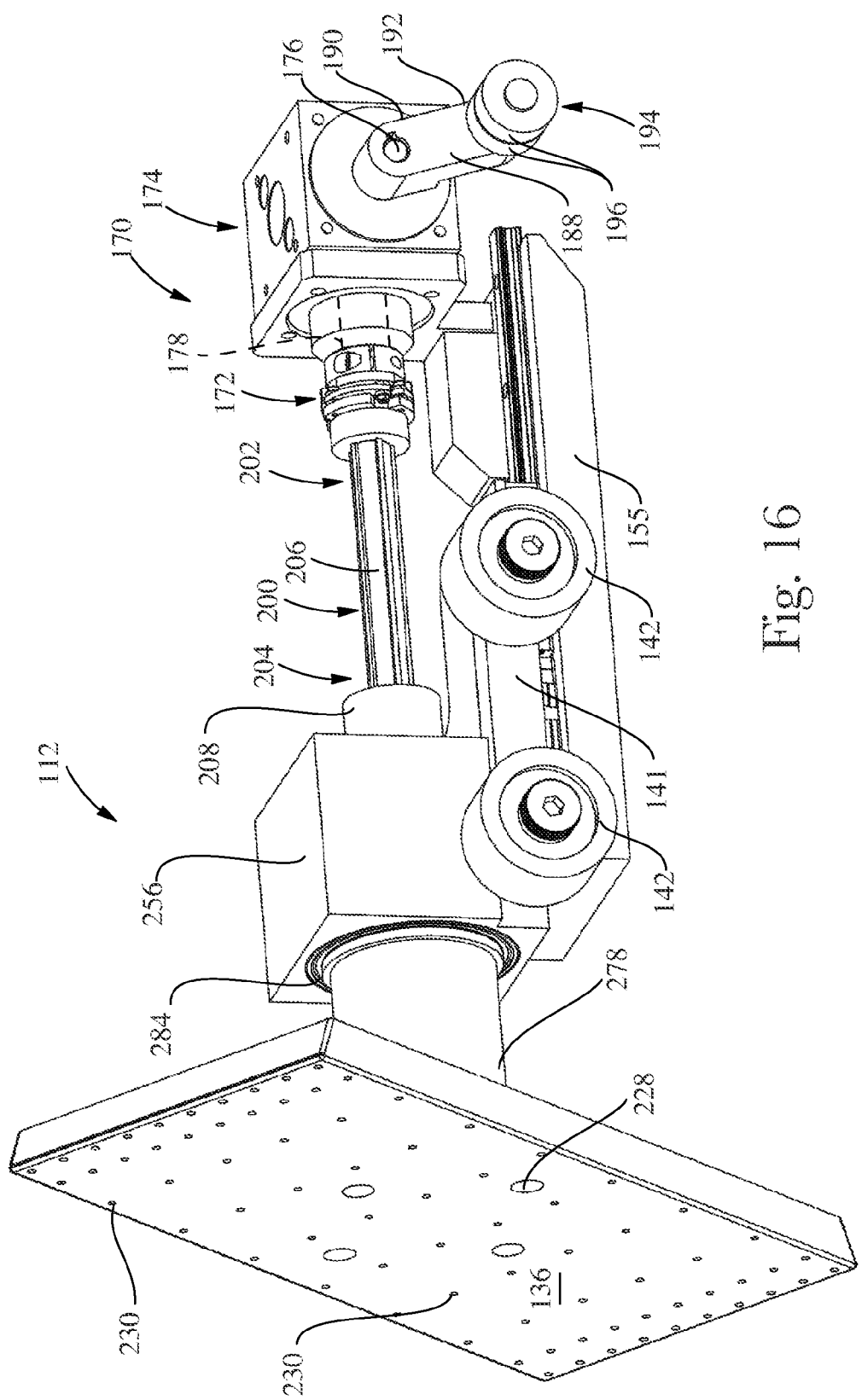
FIGS. 16-18 are perspective views of a transfer member engaged with a rotation assembly in accordance with various non-limiting embodiments.
Figure 17:
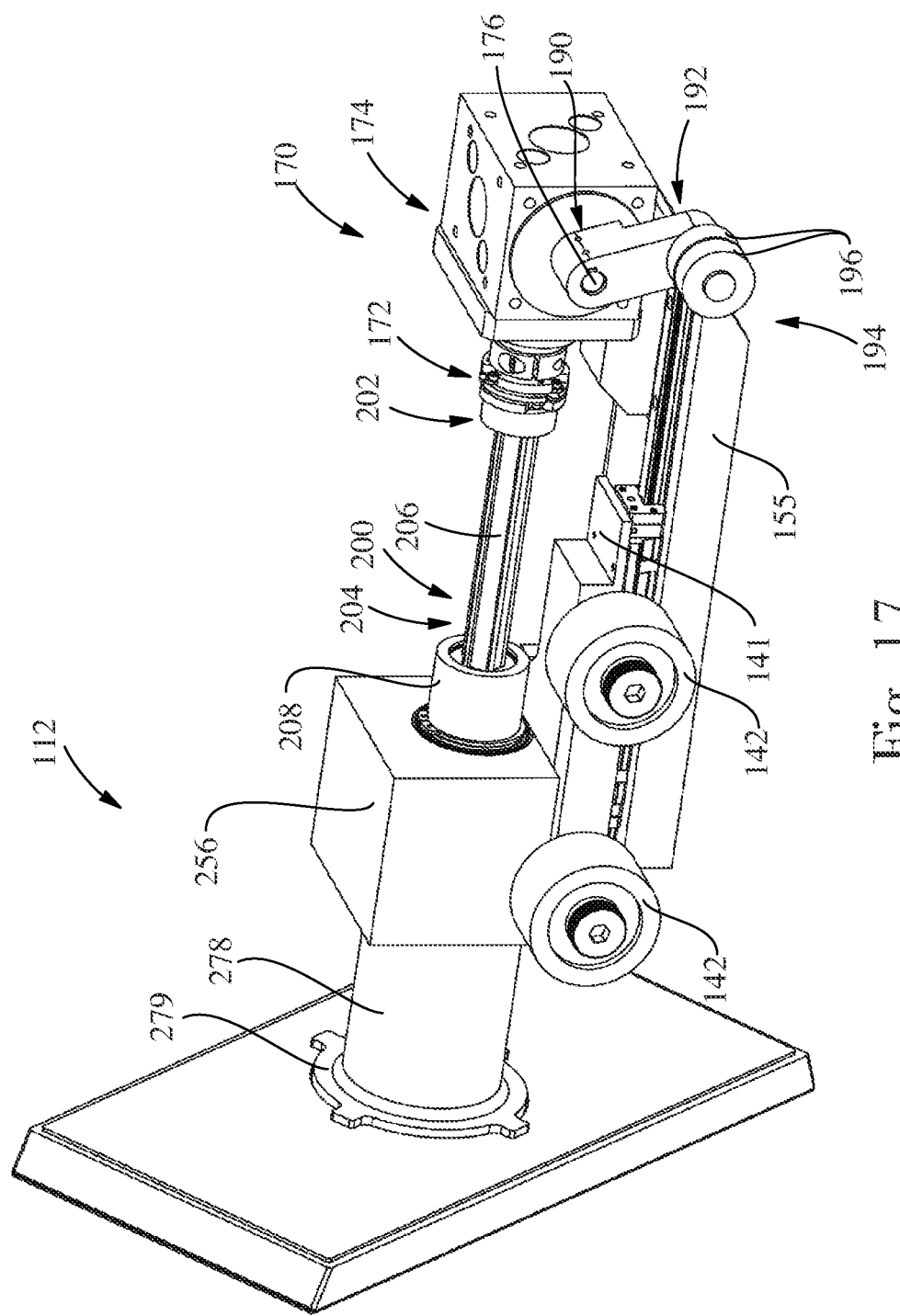
Figure 18:
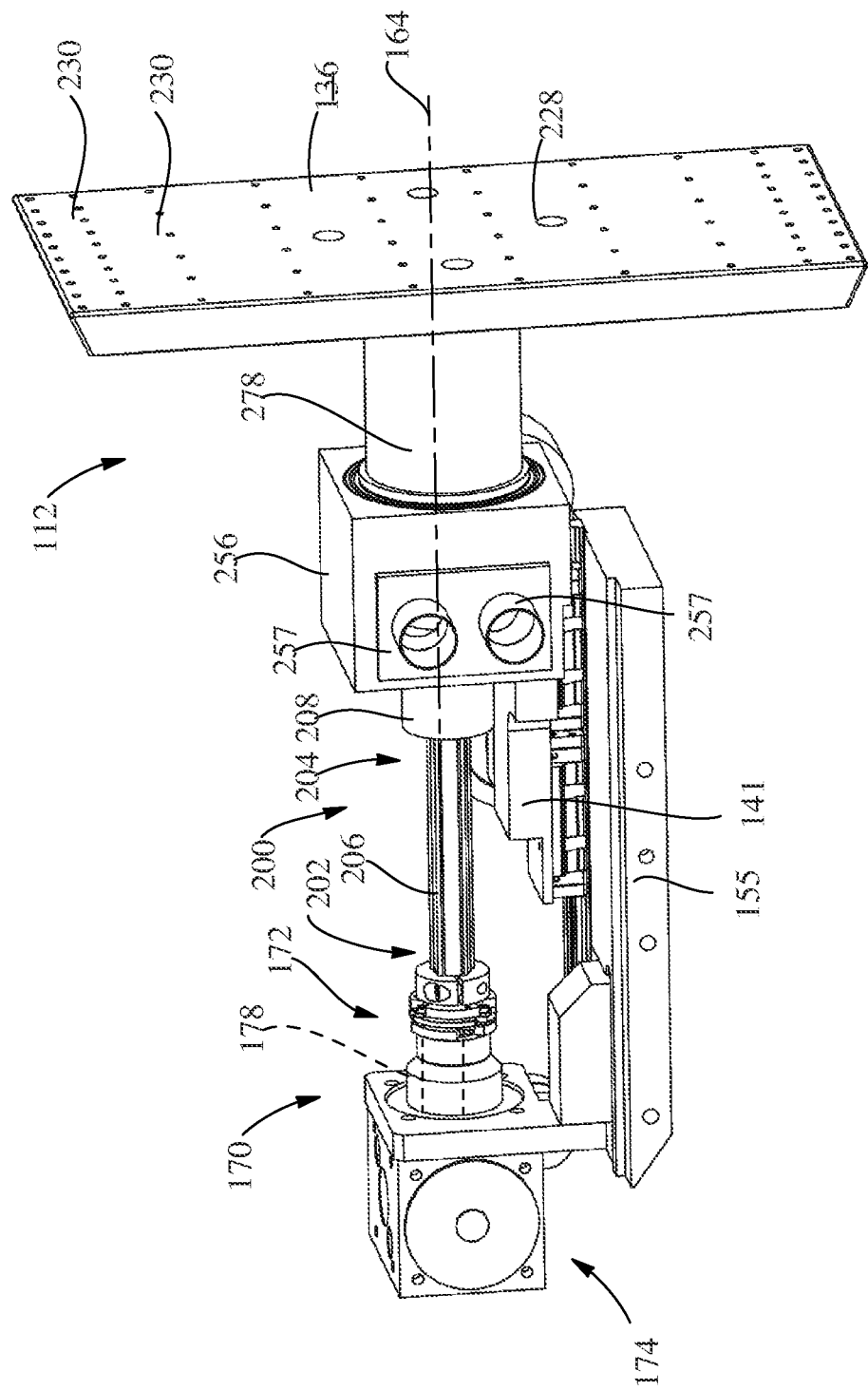

In one embodiment, referring to FIGS. 16-18 for clarity, the transfer members 112 may comprise a fluid manifold (as described below) attached to or formed with a base 141 and the follower members 142 may be mounted, or rotatably mounted, to the base 141. The base 141 may be slidably or movably engaged with a plate 155 such that the transfer members 112 may be moved radially relative to the wheel 138 and the plate 155 by the track 134. The plate 155 may be used to mount portions of the transfer members 112 and portions of the rotation assembly (as described below) to projections 156 on the wheel 138, as described in further detail herein.

In one embodiment, referring to FIGS. 1 and 4-10, the wheel 138 may be engaged with the frame 130 such that the wheel 138 is permitted to rotate relative to the frame 130 about the rotation axis 132. The frame 130 may locate bearings that support the drive shaft 148 and/or the wheel 138. This permits rotation of wheel 138 and the drive shaft 148 about the first rotation axis 132. This also locates the axial position of the wheel 138 and the drive shaft 148. The first rotation axis 132 may be located generally centrally, although not necessarily at the midpoint of the track 134, within the circumference of the track 134. A drive shaft 148 that has a rotation axis common to the rotation axis 132 may be driven by one or more actuators 150 through the use of a drive belt or chain 152, for example. The drive shaft 148 may be engaged with the wheel 138 to cause the wheel 138 to rotate. Other means of rotating the drive shaft 148 can be envisioned by those of skill in the art and will not be discussed in detail for brevity. The one or more actuators 150 may cause the drive shaft 148 to rotate in either the clockwise or counter-clockwise direction. The drive shaft 148 may rotate in either direction and at any speed about the rotation axis 132 to drive or rotate the wheel 138. In one embodiment, the wheel 138 may rotate in a direction generally parallel with the plane of the frame 130 from which the track 134 extends or is defined in. The wheel 138 may be fixedly attached to the drive shaft 148 such that upon activation of the one or more actuators 150, the drive shaft 148 and, thereby, the wheel 138 may rotate.

In one embodiment, the wheel 138 may have one or more recesses 154 defined in a perimeter thereof. Fluid conduits and/or other components may extend through the recesses 154 to portions of the transfer members 112. Also, by providing the recesses 154 in the wheel 138, the wheel 138 will be lighter and have less rotational inertia.

In various embodiments, referring again to FIGS. 1 and 4-10, the wheel 138 may be engaged with one or more of the transfer members 112 through the use of the plate 155. The wheel 138 may have projections 156 extending therefrom in a direction toward the frame 130. Portions of the plate 155 extending intermediate a portion of the transfer member 112 and a torque transmitting assembly (as discussed below), for example, may be mounted to the projections 156 on the wheel 138 to provide support to the rotating assembly which includes the transfer member 112. The plate 155 may be movably engaged with the base 141 as described in greater detail herein. Portions of the transfer members 112 may also be engaged with shafts or shaft assemblies comprising a spline, for example, to allow the transfer members 112 to be movable in radial directions relative to the first rotation axis 132. The shaft or shaft assemblies may also allow portions of the transfer members 112 to be turned relative to the wheel 138 about a second rotation axis 164 that may be positioned generally perpendicular, or transverse, to first rotation axis 132. The shaft or shaft assemblies and the transfer members 112 may rotate with the wheel 138. Transfer members 112 may have a constant relative angular position about the first rotation axis 132 and may share the same angular velocity about the first rotation axis 132.

In one embodiment, the wheel 138 may be engaged with one to sixteen transfer members 112, for example. All or some of the transfer members 112 may be used to transfer discrete articles 102 in various manufacturing operations. In one embodiment, every other, or every third, transfer member 112 may be used to transfer discrete articles 102 in a particular manufacturing operation, for example.

In various embodiments, referring to FIGS. 7, 8, 10, and 16, the one or more follower members 142 may extend from the base 141 or other portion of the transfer members 112 such that they may engage the track 134 and move the transfer members 112 radially. The follower members 142 may be attached to portions of the transfer members 112 or may be formed with the transfer members 112. The "transfer members 112" may refer to not only the portion comprising the transfer surface 136 but all of the radially movable assembly at the second end 204 of the shaft or shaft assembly 200. Radially moving assemblies include the fluid manifold, the spline receiving member, the base 141, the follower members 142, the housing, and the transfer surface 136, for example. Some of these components are discussed in more detail below. The shaft, the spline, and the second end of the shaft (as are all discussed below) may not be radially moving. In certain embodiments, more than two follower members 142 may be desired on a particular track 134 or if more than one track 134 is provided on the frame 130. In an example, two tracks (not illustrated) for the follower members 142 may be provided on a frame and one or more follower members may be movably engaged with each of the tracks. The follower members 142 being movably engaged with the track 134 causes the transfer members 112 to circumnavigate about a path about the rotation axis 132 in correspondence with the track 134.

In various embodiments, the shape of the track 134 may be such that it causes the follower members 142 and, thereby, the transfer members 112, and the transfer surfaces 136 of the transfer members 112, to be moved radially inwardly and outwardly when the transfer members 112 are rotating about the path of the rotation axis 132 in correspondence with the track 134. This path can be seen in FIGS. 7, 8, and 10, for example. The path may be said to be about the rotation axis 132. The track 134 may comprise a first projection 158 extending radially outwardly from the rotation axis 132 proximate to the first moving carrier member 104 and a second projection 160 extending radially outwardly from the rotation axis 132 proximate to the second carrier member 106. This radial extension of the projections 158 and 160 is discussed with reference to a non-projection portion 162 of the track 134. The projections 158 and 160 may have any suitable shape which generally extends radially outwardly from the rotation axis 132. The shape of the projections 158 and 160, among other things, may dictate the tangential velocity of a portion of the transfer surface 136 at the point or zone of discrete article transfer from or to one of the moving carrier members 104 and 106. The shape of the projections 158 and 160 may also contribute to or cause the gap between the transfer surfaces 136 and surfaces of the first and second moving carrier members 104 and 106 to remain constant or substantially constant at the point or zone of discrete article transfer. These projections 158 and 160 may be positioned at any locations on the track 134 that are proximate to an incoming first moving carrier member 104 or an outgoing moving second carrier member 106. In one embodiment, the track 134 may only have one projection 158 or 160 positioned proximate to one of the moving carrier members 104 and 106. The first projection 158 may be generally across the track 134 from the second projection 160 or otherwise situated relative to the second projection 160 depending on the positioning of the incoming first moving carrier member 104 and the outgoing second moving carrier member 106. The radius of the track 134 relative to the rotation axis 132 may increase and decrease about the track 134, even in the non-projection portions 162 of the track 134. In one embodiment, the radius of the track 134 may increase at least when portions of the transfer members 112 are partially rotated between the first position 116 and the second position 118 to allow two adjacently positioned transfer surfaces of the transfer members 112 to clear each other (i.e., not contact each other) during rotation of the transfer members 112 about the second rotation axis 164. The increased radius of the track 134 at these locations forces the transfer members 112 radially outwardly relative to the rotation axis 132, thereby providing adequate clearance of a first transfer surface 136 and an adjacent second transfer surface 136 to rotate between the first position 116 and the second position 118. The second rotation axis 164 may be perpendicular, generally perpendicular, or transverse to the rotation axis 132. In other embodiments, the rotation axis 132 may extend in a first direction and the second rotation axis 164 may extend in a second, different direction. The second, different direction may be generally parallel (e.g., +/−one to fifteen degrees) to a plane of the frame 130 from which the rotation axis 132 extends, wherein the plane extends generally perpendicular to the rotation axis 132. The rotation of the portions of the transfer members 112 and an example rotation assembly configured to accomplish this rotation will be discussed in further detail below.

In one embodiment, the track 134 may not increase the radial distance of the transfer members 112 from the rotation axis 132 during movement of the transfer surfaces 136 between a first position and a second position. In such an embodiment, the transfer surfaces 136 may be shaped (e.g., ovate, round) or spaced such that they can be turned between the first position and the second position without contacting each other.

In one embodiment, referring to FIGS. 1 and 4-12, the transfer members 112 may each comprise the transfer surface 136 on the distal most portion thereof relative to the rotation axis 132, as referenced above. The transfer surface 136 may be flat, or substantially flat, in one or more directions. FIG. 11 illustrates the flat, or substantially flat, transfer surface in a first direction, while FIG. 12 illustrates the flat, or substantially flat, surface in a second direction. Substantially flat, as used herein, means the transfer surface 136 used to support and transport a discrete article 102 conforms to a plane within about 0-10 mm, and alternatively about 0-5 mm, not including fluid ports and bolt holes, as discussed below. Example transfer surfaces 136 are illustrated as rectangular, but it is to be understood that other transfer surfaces for use with the transfer members 112 of the present disclosure may be formed of other suitable shapes, such as squares, circles, or ovals, for example. In one embodiment, a portion of each transfer surface 136 may be flat, or substantially flat, while other portions may be arcuate. In various embodiments, although not illustrated, some of the transfer surfaces of the transfer members of a transfer assembly may be flat, or substantially flat, while other transfer surfaces may be arcuate. The portions of the transfer members 112 supporting the transfer surfaces 136 (e.g., the portions attached to the distal end of the housing 278 as described below) may be flat, substantially flat, or arcuate.

By providing flat, or substantially flat, transfer surfaces 136, a significant advantage may be achieved in that the flatness of the transfer surfaces 136 is the same, or substantially the same, whether the transfer surface 136 is in the first position 116 or rotated into the second position 118 about the second rotation axis 164. In one embodiment, a transfer surface 136 may have a flat, or substantially flat leading portion, an arcuate middle portion, and a flat, or substantially flat, trailing portion. This geometry of a transfer surface 136 may be employed for substantially constant gap transfer at the leading and trailing portions (and not the middle portion), for example. As referenced above, on related art transfer assemblies, having arcuate transfer surfaces with the arc extending generally in the longitudinal direction of the transfer surface, once the transfer member is rotated into the second position (a position which is generally 90 degrees from the first position), transfer of the discrete articles may become an issue because of the arc being in the wrong direction for transfer to a second moving carrier member. Stated another way, if the arc is suitable for picking up a discrete article from a first moving carrier member, it generally may not be suitable for dropping off a discrete article onto a second moving carrier member because the outer edges of the transfer surface may be more distal from the second moving carrier member, potentially leading to inefficient transfers. The flat, or substantially flat, transfer surface 136 of the present disclosure solves that problem by providing the same, or substantially the same, distance or gap between all or most portions of the transfer surface 136 and the moving carrier member after the transfer surface 136 is rotated from the first position 116 into the second position 118 about the second rotation axis 164. This can lead to improved discrete article transfers and increased speed of the transfers.

Again as referenced above, one problem that may arise, however, in related art transfer assemblies using flat, or substantially flat, transfer surfaces that do not have the ability to move their transfer members radially inwardly and radially outwardly with respect to the rotation axis of the transfer assemblies, may be that there will be a significant gap at the point of discrete article transfer while portions of the flat, or substantially flat, transfer surface pass through the discrete article transfer point or transfer zone. In such an instance, the leading edges and trailing edges of the flat transfer surface may be positioned quite close to the moving carrier member, while the middle portion of the transfer surface, owing to its flat, or substantially flat, configuration, may be positioned more distal from the moving carrier member. This gap between the middle portion of the flat, or substantially flat, transfer member and a moving carrier member and/or gap variation may result in poor or unacceptable transfers, especially during high speed transfers, which are desired in absorbent article manufacturing. The poor transfer may result in folding of portions of the discrete article over itself, for example.

Referring to FIGS. 7, 8, and 10C, the present disclosure solves this gap problem, among others, in the middle portion of a related art transfer surface by providing the track 134 with the projections 158 and 160 therein at or proximate to the moving carrier members 104 and 106. By providing the projections 158 and 160, the transfer surfaces 136 of the transfer members 112 of the present disclosure may maintain a constant, or substantially constant (e.g., 0.1-2 mm or 0.1-3 mm), distance or minimum distance between themselves and the moving carrier members 104 and 106 at the point or zone of discrete article transfer. FIGS. 10A-10C illustrate the progression of the transfer surface 136 when moving past the second moving carrier member 106 in the direction of arrow A. FIGS. 13A-13C illustrate the progression of the transfer surface 136 when moving past the first moving carrier member 104 in the direction of arrow B. In one embodiment, the distance may be constant, or substantially constant, then not constant, and then constant, or substantially constant again at the point or zone of discrete article transfers as the transfer surface 136 moves past one of the moving carrier members. The point or zone of discrete article transfer may be the point or zone at which a portion of the discrete article 102 leaves the first moving carrier member 104 and transfers to the transfer surface 136. The point or zone of discrete article transfer may also be the point or zone at which a portion of the discrete article 102 leaves the transfer surface 136 and transfers to the second moving carrier member 106. Since the transfer surfaces 136 of the present disclosure are flat, or substantially flat, the transfer surfaces 136 generally may need to be moved radially outwardly and radially inwardly as portions of the transfer surfaces 136 pass through the discrete article transfer point or zone with the moving carrier members 104 and 106. The projections 158 and 160 constrain such radial movement of the transfer members 112 since the transfer members 112 are movably engaged with the track 134 and rotate about a path about the rotation axis 132 in correspondence with the track 134. As such, each of the transfer members 112 and, thereby, the transfer surfaces 136 may be moved or cammed consistently or variably radially outwardly relative to the rotation axis 132 from when, or about when, the leading edge of the transfer surface 136 is at or proximate to the point or zone of discrete article transfer until when, or about when, a midpoint or mid portion (in the machine direction of travel) of the transfer surface 136 is at or proximate to the point or zone of discrete article transfer. At such a time, the transfer surface 136 may then be moved or cammed consistently or variably radially inwardly until the trailing edge of the transfer surface 136 is at or past the point of discrete article transfer or until the transfer member 112 has travelled over the projection 158 or 160 and back onto a non-projection portion 162 of the track 134.

In various embodiments, the angular velocity of the rotation about first rotation axis 132 of the transfer members 112 may be or is constant, or substantially constant, in that the rotation of the drive shaft 148 and the wheel 138 may be constant. That being said, the tangential velocity of the transfer surfaces 136 may be variable when the transfer members 112 are moved radially outwardly and inwardly. Generally, if the transfer members 112 are moved radially outwardly, the tangential velocity of transfer surfaces 136 will increase, while if the transfer members 112 are moved radially inwardly, the tangential velocity of the transfer surfaces 136 will decrease owing to the transfer members 112 being rotated about the rotation axis 132. The tangential velocity of the transfer surfaces 136 at the point or zone of discrete article transfer may be constant, or substantially constant (e.g., within 0.1%-2%) and matched to the tangential velocity of the first or second moving carrier members 104 or 106 during transfer. This is accomplished by maintaining a substantially constant radial displacement between the zone of discrete article transfer and the first rotation axis 132. The radial displacement of the transfer surface 136 is adjusted as the follower members 112 travel over the projections 158 and 160. By providing constant, or substantially constant, tangential velocities of the transfer surfaces 136 at the point or zone of discrete article transfer, smoother and matched speed discrete article transfers may be accomplished. The projections 158 and 160 may be designed so that a first projection provides a transfer surface 136 with a first tangential velocity at a first point or zone of discrete article transfer (i.e., pick up) and a second projection provides the same transfer surface 136 with a second tangential velocity at a second point of discrete article transfer (i.e., drop off). As such, the transfer assembly 100 may pick up a discrete article 102 from the first moving carrier member 104 having a first velocity or tangential velocity at a first point or zone of discrete article transfer and may drop off the discrete article 102 onto the second moving carrier member 106 having a second velocity or tangential velocity at a second point of discrete article transfer. In one embodiment, the transfer assembly may be configured to pick up the discrete articles from the second moving carrier member 106 and transfer them to the first moving carrier member. In such an embodiment, the direction of rotation of the transfer members 112 about the rotation axis 132 may be clockwise or counterclockwise.

The transfer assembly 100 may be used to transfer discrete articles 102 from the first moving carrier member 104 at a first pitch (i.e., spacing of discrete articles) to a second moving carrier member 106 at a second pitch (i.e., repitching). The transfer assembly 100 is capable of achieving suitable transfer of the discrete articles 102 as the pitch increases, decreases, or remains the same between the first and second moving carrier members 104 and 106.

Transferring the discrete articles 102 from the transfer surface 136 to the second moving carrier member 106 using the transfer apparatus of the present disclosure may provide suitable and efficient bonding of the discrete articles 102 to the webs of front and rear belts 124 and 126 or to front and rear belts because the constant gap clearance, or substantially constant gap clearance, may be adjusted to provide uniform bonding pressure between the transfer surface 136 and the second moving carrier member 106. The constant gap, or substantially constant gap, may be adjusted to interfere with the discrete article 102 and create bonding pressure that will be constant, or substantially constant, across the area of the discrete article 102 or the area of a portion of the discrete article 102. This may be useful for creating suitable bonds between the discrete article 102 and the webs of front and rear belts 124 and 126 when a hot melt adhesive or other pressure sensitive adhesive is employed.

The transfer assembly 100, with a variable radius transfer member mechanism, may also be employed to improve transfer from transfer surfaces that are not flat. For example, a transfer surface that is arcuate may benefit from adjusting the radial position of the transfer surface during transfer from the first moving carrier member 104 or to the second moving carrier member 106. Likewise, a transfer surface that has any non-flat surface can be adjusted radially to improve the transfer from the first moving carrier member 104 to the second moving carrier member 106. A person of ordinary skill in the art will recognize that the variable radius techniques described herein may be used with related art transfer assemblies as well as the transfer assemblies disclosed herein. As such, those concepts are encompassed by the present disclosure.

In one embodiment, referring to FIGS. 13-18, a rotation assembly 170 for one or more of, or all of, the transfer members 112 of the transfer assemblies 100 discussed herein may be provided. Portions of the transfer assembly 100, some transfer members, and other components are eliminated in FIGS. 13-18 for clarity in illustrating the rotation assembly 170. The rotation assembly 170 can be viewed on the transfer assembly 100 in FIGS. 7 and 8. The rotation assembly 170 may be simpler and less costly to manufacture than a barrel cam-type rotation assembly, may have extended follower member life, and may reduce the pressure angle of the track 134. As discussed above, the transfer assembly 100 may comprise a frame 130 defining a first rotation axis 132, wherein the one or more transfer members 112 may rotate about the first rotation axis 132 (see e.g., FIGS. 3, 4, and 6-8). The rotation assembly 170 may rotate portions of the transfer member 112 about the second rotation axis 164 between the first position 116 and at least a second position 118. The first rotation axis 132 may be perpendicular, generally perpendicular (e.g., one to fifteen degrees), or transverse to the second rotation axis 164. In other embodiments, the first rotation axis 132 may extend in a first direction and the second rotation 164 axis may extend in a second, different direction. In various embodiments, the first rotation axis 132 may or may not intersect the second rotation axis 164.

In one embodiment, referring to FIGS. 13-20, the rotation assembly 170 may comprise a torque transmitting assembly 174 comprising an input member (or input portion) 176 and an output member (or output portion) 178. The torque transmitting assembly 174 may comprise a 90 degree gearbox or another type of gearbox. In other embodiments, the torque transmitting assembly may not comprise a gearbox and instead may be another mechanism for achieving torque transmission between perpendicular, or substantially perpendicular, shafts, such as worm gearing, bevel gearing, hypoid gearing, helical gearing, belt drives, chain drives, hydraulic drives, and/or three-dimensional space mechanisms, for example. The input member 176 and the output member 178 may be an input shaft and an output shaft, respectively. The shafts may have any suitable length and/or dimensions. The input member 176 may extend in a direction parallel to or generally parallel to the first rotation axis 132 and the output member 178 may extend in a direction parallel to, generally parallel to, or coaxial to the second rotation axis 164.

Figure 19:
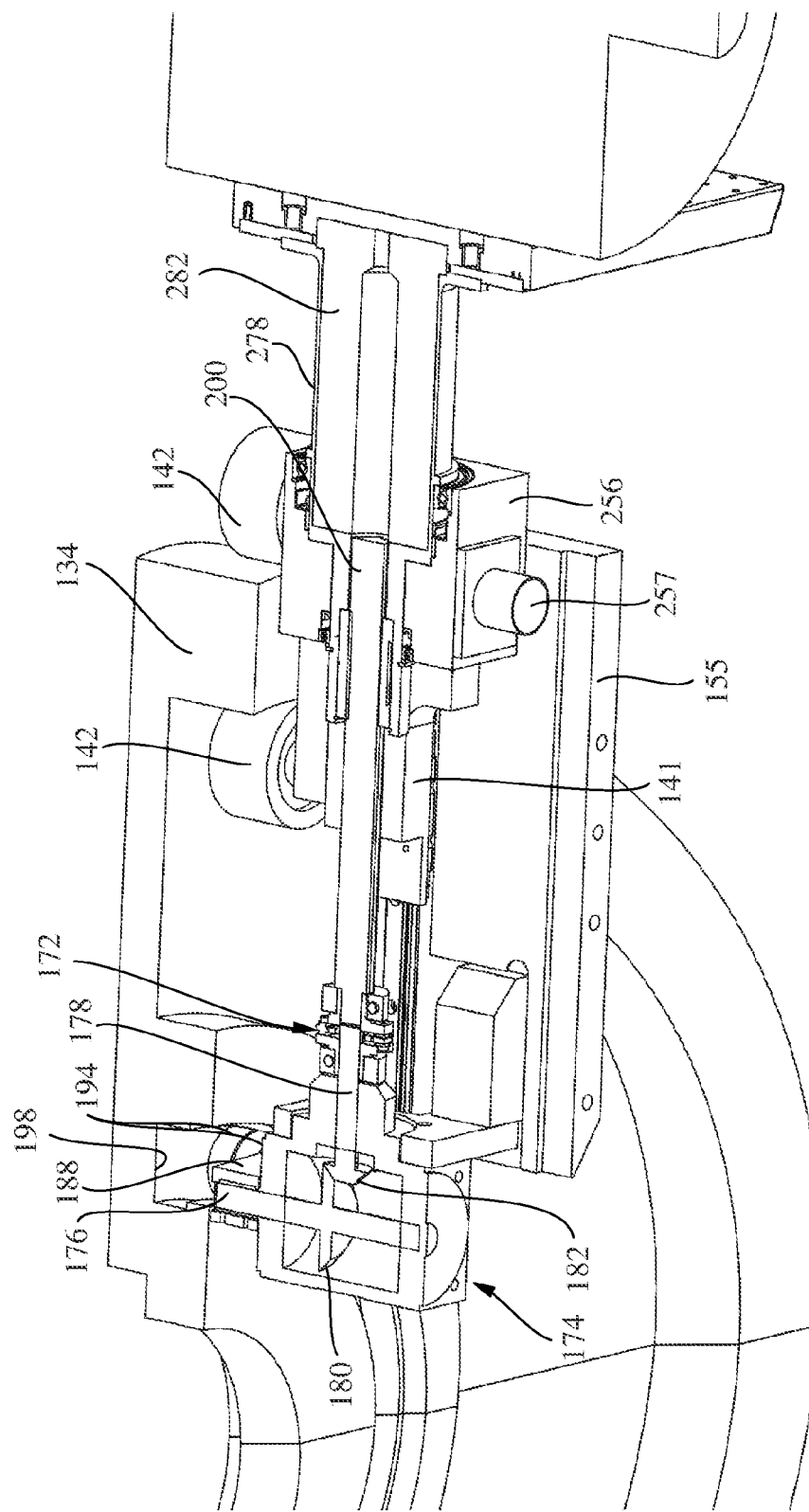
FIG. 19 is a cut away perspective view of the rotation assembly and the transfer member illustrating first and second gears in accordance with one non-limiting embodiment.
Figure 20:
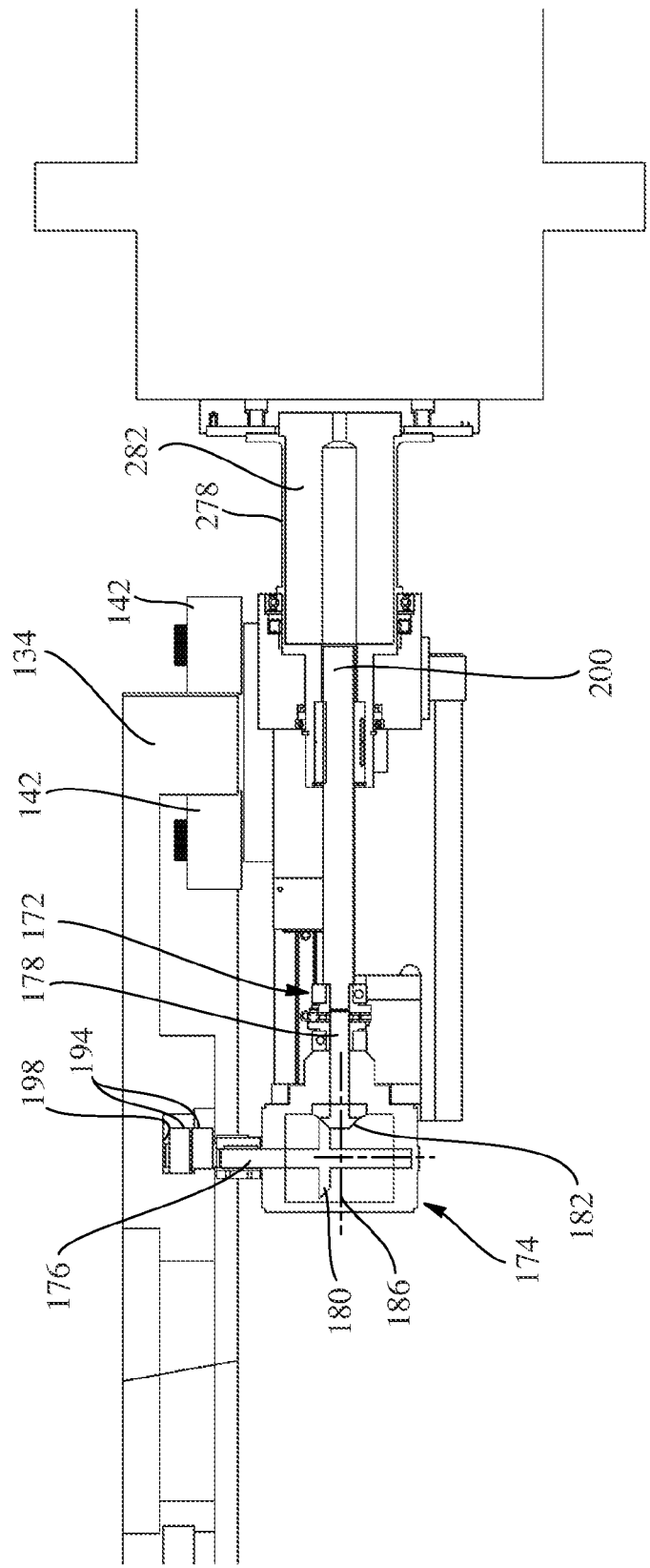
FIG. 20 is a cut away side view of the rotation assembly and the transfer member illustrating the first and second gears in accordance with one non-limiting embodiment.

In one embodiment, referring to FIGS. 19 and 20, the torque transmitting assembly 174 may comprise two or more gears. FIG. 19 is a partially cut away perspective view of the torque transmitting assembly 174, among other components, and FIG. 20 is a partially cut away top view of the torque transmitting assembly 174, among other components. The gears may each comprise teeth (not illustrated) meshingly engaged with each other. If two gears are provided, a first gear 180 may be operably engaged with the second gear 182 and may have a rotation axis 184 that is transverse, perpendicular, or generally perpendicular to rotation axis 186 of the second gear 182. The torque transmitting assembly 174 may be a speed increasing assembly, such as a 1 to 1.5, 1 to 2, 1 to 2.5, or 1 to 3 gearbox, for example. Those of skill in the art will recognize that other speed increasing assemblies may also be used and that the speed may be increased any suitable amount. One example of a speed increasing assembly 174 is discussed in further detail below. In one embodiment, the torque transmitting assembly 174 may be a speed decreasing or equal speed assembly, such as a 2 to 1, or a 1 to 1, gearbox, for example. Those of skill in the art will recognize that other speed decreasing assemblies may also be used and that the speed may be decreased any suitable amount.

In various embodiments, the rotation assembly 170 may also comprise a link or bar 188 comprising a first end 190 operably coupled or fixedly attached to the input member 176 and a second end 192 comprising a follower member 194. The input member 176 may be operably coupled to the link 188 using a key 172 or other mechanical component or assembly configured to cause the input member 176 to rotate when the link 188 is rotated about its first end 190. Stated another way, the input member 176 may be non-rotatably attached to the link 188, such that when the link 188 is rotated about its first end 190, the input member 176 rotates in unison with the first end 190 of the link 188. The link 188 may be rotated about its first end 190 when the follower member 194 is moved radially relative to the first rotation axis 132 by a track 198, as discussed in greater detail herein. The follower member 194 may be a cam follower, which, in one embodiment, may comprise a roller rotatably attached to or engaged with the second end 192 of the link 188. In various embodiments, the follower member may not be a roller and may be attached to or formed with the second end 192 of the link 188. In one embodiment, the one or more of the follower members 194 may comprise materials such as metals, plastics, and/or polymers, for example, or coatings thereof, to permit relative movement between the one or more follower members 194 and the track 198 194 (also referred to as a second track 198) for the follower members. The follower members 142 and the track 134 may comprise similar features. This second track 198 may surround the first rotation axis 132 and be surrounded by the first track 134 described above. In any event, the "inner" track 198 may be engaged with the follower member(s) 194 of the rotation assembly 170. The track 198 may comprise or be coated with the same, similar materials, or different materials as the follower members 170, for example.

In one embodiment, referring again to FIGS. 13-18, the rotation assembly 170 may comprise a shaft or a shaft assembly 200 comprising a first end 202 engaged with or operably coupled to the output member 178 of the torque transmitting assembly 174 and a second end 204 engaged with or operably coupled to a portion of the transfer member 112. The first end 202 of the shaft 200 may be operably coupled to the output member 178 using the key 172 so that when the output member 178 is rotated, the shaft 200 may be rotated at least partially about the second rotation axis 164. Stated another way, the rotation of the output member 178 may drive the rotation of the shaft 200. In one embodiment, a portion of, or all of, the shaft 200 may have a slot or groove (not illustrated) defined therein in a direction extending parallel to, or generally parallel, to its longitudinal axis. A key (not illustrated) may extend from a portion of the transfer member 112 or from the output member 178 at or proximate to the point of coupling to the shaft 200. The key may allow the transfer member 112 to be moved radially inwardly and outwardly relative to the first rotation axis 132 as portions of the transfer member 112 rotate about the first rotation axis 132 about a path in correspondence with the first track 134, as discussed above. The shaft 200 may extend into a portion of the transfer member 112, such as the fluid manifold 256 and the housing 278 (as discussed below), or the torque transmitting assembly 174 so that the distance between a shaft receiving portion of the transfer member 112 and the output member 178 (i.e., the length of the portion of the shaft 200 intermediate the shaft receiving portion of the transfer member 112 and the torque transmitting assembly 174) may be varied. The key may also allow the shaft 200 to be turned about the second rotation axis 164 by the output member 178. In essence, the key/slot feature allows the shaft 200 to be rotated about the second rotation axis 164 and to vary the distance of the portion of the shaft 200 intermediate the shaft receiving portion of the transfer member 112 and the torque transmitting assembly 174.

In one embodiment, the shaft may comprise a shaft assembly 200 comprising a spline 206 and a spline receiving member 208. The spline receiving member 208 may be positioned on or engaged with a portion of the transfer member 112 or the output member 178 at or proximate to the point of engagement with an end portion of the spline 206. If the spline receiving member 208 is positioned on the output member 178, the output member 178 may be hollow such that the spline may extend therethrough. The spline 206 may be slidably engaged with the spline receiving member 208 such that the distance between the most proximal portion of the transfer member 112 and the output member 178 may be varied as the transfer member 112 is moved radially relative to the first rotation axis 132. The end of the spline 206 not engaged with the spline receiving member 208 may be engaged with or operably coupled to the output member 178 or to a portion of the transfer member 112. In such an embodiment, as the transfer member 112 is moved radially outwardly or radially inwardly as it circumnavigates about the path of the first track 134, the length of the portion of the spline 206 intermediate the transfer member 112 and the output shaft 178 may be varied. The spline 206 and the spline receiving member 208 may allow the output member 178 to rotate the spline 206 about the second rotation axis 164 while the transfer member 112 is moved radially relative to the first rotation axis 132. Those of skill in the art will recognize that other shaft assemblies that allow adjustment of the length of the portion of the shaft between the transfer member 112 and the output member 178 are within the scope of the present disclosure.

In one embodiment, although not illustrated, a shaft assembly may comprise a shaft portion and a shaft receiving portion. The shaft may be slidably engaged with the shaft receiving portion in a telescoping fashion (not illustrated) to allow axial expansion and contraction of the shaft assembly relative to the first rotation axis. The shaft may be non-rotatably engaged with the shaft receiving portion such that the output member 178 may rotate the shaft and the shaft receiving portion.

Figure 13:
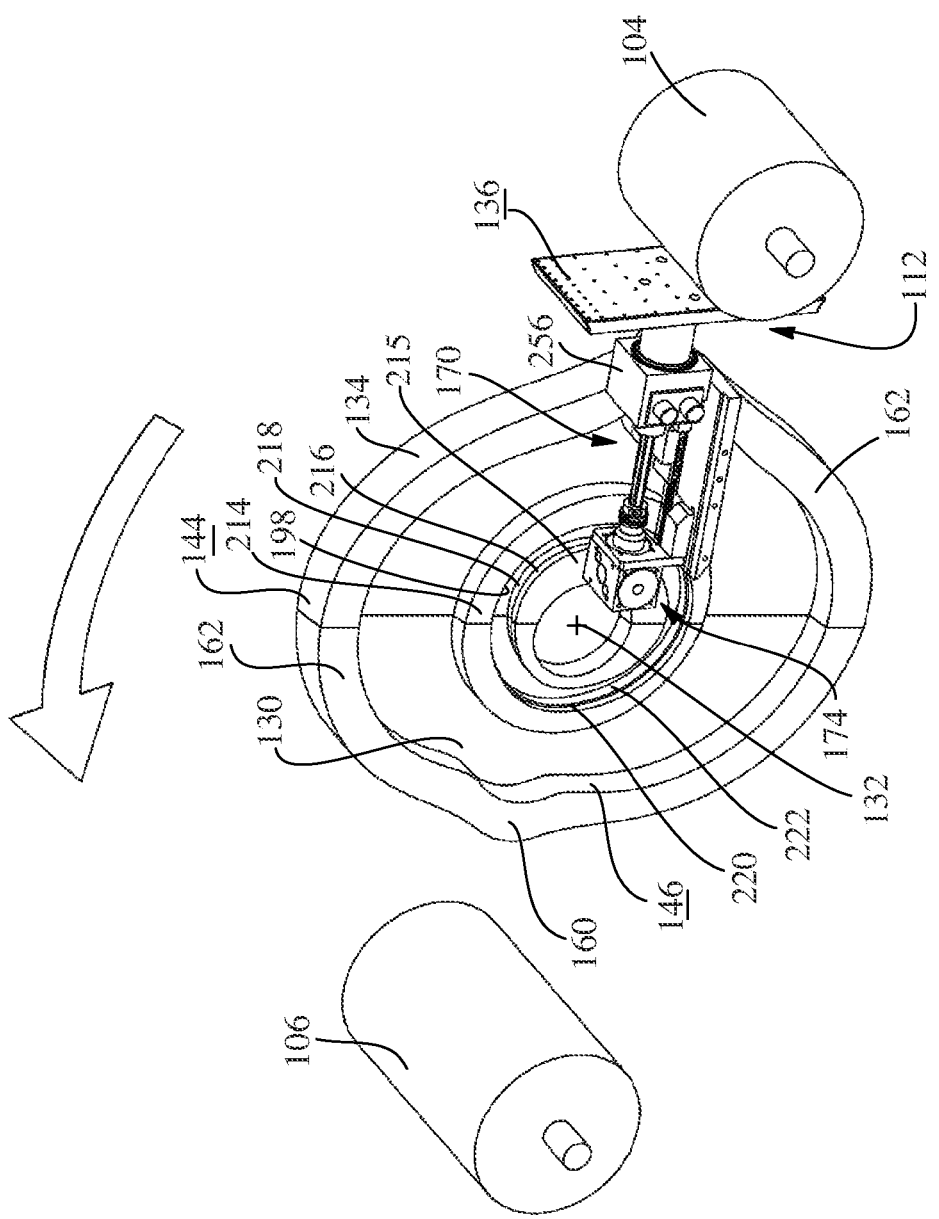
FIG. 13 is a front perspective view of two tracks, a rotation assembly, and a transfer member in a pick up zone, with a transfer surface in a first position, in accordance with one non-limiting embodiment.
Figure 14:
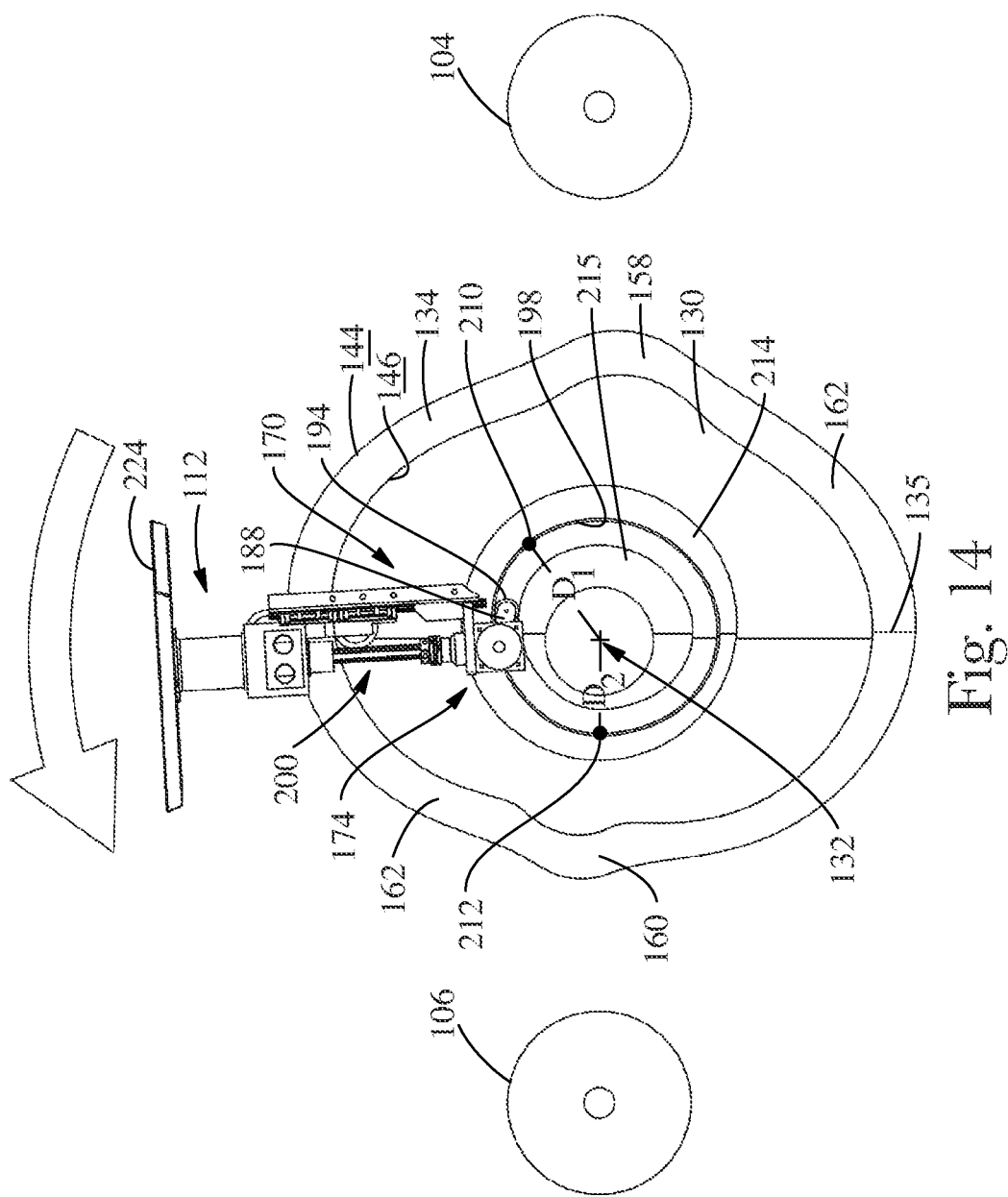
FIG. 14 is a front view of the two tracks, the rotation assembly, a transfer member, wherein portions of the transfer member are moving from a first position into a second position in accordance with one non-limiting embodiment.

In one embodiment, referring to FIGS. 7, 8, 10, and 13-15, the rotation assembly 170 may be engaged with the track or second track 198 positioned on or in the frame 130 and surrounding the first rotation axis 132. The second track 198 may be surrounded by the first track 134 such that the second track 198 may be an inner track and the first track 134 may be an outer track relative to the first rotation axis 132. In the claims, the inner track and the outer track may be referred to as a track, a first track, or a second track depending on which of the tracks is recited first. Referring to FIG. 14, a first point 210 at a first location on the second track 198 may be first distance, D1, away from the first rotation axis 132 and a second point 212 at a second location on the second track 198 may be a second distance, D2, away from the first rotation axis 132. The first distance, D1, may be different than the second distance, D2. Other points on the second track 198 may be other distances away from the first rotation axis 132. This distance variation of various points on the second track 198 relative to the first rotation axis 132 may allow the shaft or shaft assembly 200 to rotate about the second rotation axis 164, thereby moving a portion of the transfer member 112 between the first position 116 and at least the second position 118.

In various embodiments, the second track 198 may be a cam track or a radial cam, for example. In one embodiment, although not the illustrated embodiment, but similar to the first cam track 134, the second track 198 may extend outwardly from a front plane of the frame 130 and form a projection that surrounds the first rotation axis 132. In such an embodiment, the second track 198 may be formed with the frame 130 or may be attached to the frame 130. The projection may comprise a first side surface, a second side surface, and a top surface. The first side surface may be positioned parallel to, or generally parallel to (e.g., 0 to 15 degrees), the second side surface. The top surface of the projection may extend in a direction parallel to, or generally parallel to, the plane of the frame 103 and in a direction perpendicular to, or generally perpendicular to, the first and second side surfaces. The distance between the first side surface and the second side surface may be constant, substantially constant, or variable about the projection. Two follower members may be engaged with, attached to, or formed with the second end 192 of the link 188 and may each be movably engaged with one of the side surfaces of the projection. In one embodiment, two links, each comprising a follower member on their second end, may be provided if two follower members are provided, as will be recognized by those of skill in the art. The follower members may be biased toward the side surfaces of the projection.

Figure 15:
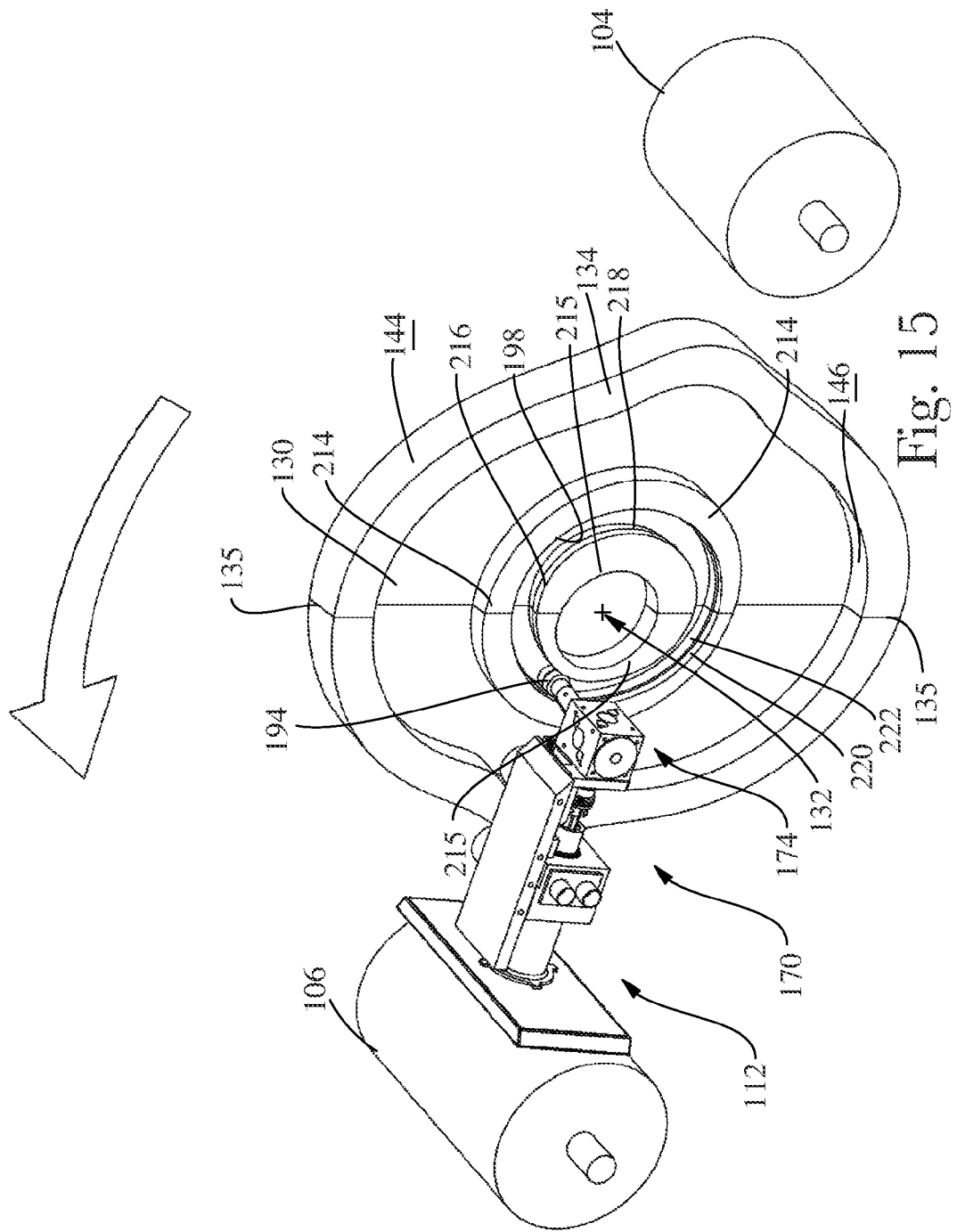
FIG. 15 is a front perspective view of the two tracks, the rotation assembly, and the transfer member, wherein a portion of the transfer member is in a drop off zone in a second position, in accordance with one non-limiting embodiment.

In another embodiment, referring to FIGS. 13-15, the second track 198 may be a cam track or groove defined in a front plane of the frame 130 and surrounding the first rotation axis 132. The cam track or groove may optionally be surrounded by a projection 214 positioned more radially outward from the first rotation axis 132 than the groove. The projection 214 may have a constant width or may have a variable width throughout its circumference. By providing the projection 214, the groove may be partially, or fully, defined in a front plane of the frame 130. The groove may also be formed intermediate the projection 214 and another projection 215 extending from the front plane of the frame 130. If the projection 214 is not provided, the groove may be fully defined in a front plane of the frame 130. In various embodiments, one or more of the follower members 194 may be at least partially positioned with the cam track or groove 198 and may engage side walls of the second cam track or groove 198 as the transfer member 112 rotates about the first rotation axis 132. Any of the follower members 194, regardless of whether the second track 198 is a projection or a groove, may be moveably engaged with the second track 198 and may circumnavigate about the first rotation axis 132 about a path in correspondence with the second track 198.

In one embodiment, referring to FIGS. 13-15, the groove of the second track 198 may have a first surface 216 and a second surface 218 on a portion of the groove most proximal to the rotation axis 132. The projection 214 may also have a first surface 220 and a second surface 222 on a portion of the projection most proximal to the rotation axis 132. The first surface 216 and the second surface 218 may extend different distances from the first rotation axis 132. Likewise, the first and second surfaces 220 and 222 may be positioned at different distances from the first rotation axis 132. A distance between the first surface 216 and the first surface 220 may be the same, or substantially the same, and, likewise, a distance between the second surface 218 and the second surface 222 may be the same, or substantially the same. Stated another way, the first surface 216 may be offset from the second surface 218 and the first surface 220 may be offset from the second surface 222. In such an embodiment, the second end 198 of the link 188 may comprise a first follower member 194 and a second follower member 194. In one embodiment, the follower members 194 may be rotatably engaged with the second end 198 of the link 188 using a pin, bolt, or other attachment mechanism or component. The follower members 194 may be positioned adjacent to each other and may each rotate about the pin or bolt, for example. The first follower member 194 may be engaged with the first surface 216 and the second follower member 194 may be engaged with the second surface 222. Surfaces 218 and 220 may not be engaged by the follower members 194 due to the offset of the surfaces 218 and 220 relative to the surfaces 216 and 222. By providing essentially two cam tracks in the groove and two follower members 194, each follower member may only turn in one direction. In other embodiments, the second track 198 may only have one surface on each side of the groove and only one follower member 194 may ride within the track 198.

In one embodiment, referring to FIGS. 7, 8, 10, and 13-20, when the one or more follower members 194 are moved radially relative to the first rotation axis 132 as they circumnavigate about the path in correspondence with the second track 198, the link 188 may be rotated in a clockwise or counterclockwise direction about its first end 190 thereby imparting a rotational force or torque to the input member 176. The torque transmitting assembly 174 may then impart the rotational force to the output member 178 and, thereby the shaft or the shaft assembly 200 owing to the gearing arrangement within the torque transmitting assembly 174. In one embodiment, the input member 176 may be rotated with the first end 190 of the link 188 a first rotational distance and may impart a second rotational distance to the output member 178 and, thereby the shaft or shaft assembly 200, owing to the gearing arrangement within the torque transmitting assembly 174. The second rotational distance may be greater than the first rotational distance. The rotation of the shaft or the shaft of the shaft assembly 200 may cause the transfer member 112 to move between the first position 116 and the second position 118 about the second rotation axis 164. At least a portion of this rotation between the first position 116 and the second position 118 may occur when the first track 134 has radially expanded the distance between the transfer member 112 and the output member 178 or when the transfer member 112 has been moved radially outwardly by the first track 134 relative to the first rotation axis 132. The second rotation axis 164 may be an axis formed about a longitudinal axis of the shaft or the shaft of the shaft assembly 200. In one revolution of the transfer member 112 about the first rotation axis 132, the shaft or the shaft of the shaft assembly 200 may be rotated from the first position 116 into the second position 118 and back into the first position 116. The transfer surfaces 136 may be rotated between 45 degrees to 180 degrees, 60 to 150 degrees, 75 degrees to 105 degrees, about 90 degrees (e.g., plus or minus 3 degrees), or 90 degrees when the transfer member 112 is moved between the first position 116 and the second position 118. All degrees or degree ranges within the above-specified ranges are specifically recited herein, but are not written out for brevity.

In one embodiment, the second track 198 may vary the angle of the transfer member 112 rotating about the second rotation axis 164 due to the changing radius of the follower member 194. The second track 198 may also have dwell regions therein where the radius of the follower members 194 and the rotation angle of the transfer members 112 remain constant, or substantially constant. These dwell regions may be useful when the transfer member is in the first position 116 and in the second position 118 during the transfer of the discrete articles 102 from the first moving carrier member 104 to the second moving carrier member 106.

Although the rotation assembly 170 is illustrated in use with the transfer assembly 100 as an example, the rotation assembly 170 may be applied to other transfer assemblies known to or developed by those of skill in the art and may function independently of the transfer assembly 100. In one embodiment, other transfer assemblies than the rotation assembly 170 of the present disclosure may be used with may not have transfer members that move radially relative to the first rotation axis 132. In one example, the rotation assembly 170 may be used with transfer members that have a varying angular position about the first rotation axis 132, for example.

In one embodiment, the transfer members 112 may be cammed or moved radially outwardly to provide clearance for rotation of the transfer members 112 about the second rotation axis 164 with adjacent transfer members 112. In other embodiments, the spacing or shape of the transfer members 112 may not require increasing their radial position for rotation about the second rotation axis 164. In another embodiment, the radius of the transfer members 112 may decrease to provide clearance for transfer member rotation about the second rotation axis 164. In another embodiment, the transfer members 112, or portions thereof, may tilt relative to first rotation axis 132 to allow clearance with adjacent transfer members 112 during rotation about the second rotation axis 164.

In one embodiment, a method of transferring one or more discrete articles 102 from a first moving carrier member 104 to a second moving carrier member 106 using a transfer assembly 100 is provided. The transfer assembly may comprise a frame defining a first rotation axis and one or more transfer members each comprising a transfer surface configured to receive one or more of the discrete articles. The method may comprise rotating the one or more transfer members about the first rotation axis and selectively varying the radial distance of the one or more transfer surfaces relative to the first rotation axis as the one or more transfer member rotate about the first rotation axis. The method may also comprise rotating the one or more transfer surfaces, and other portions of the transfer members, about a second rotation axis between a first position and at least a second position using a track that surrounds the first rotation axis, one or more follower members circumnavigating about a path in correspondence with the track while the transfer member rotates about the first rotation axis, a torque transmitting assembly, a link comprising a first end operably coupled to a first portion of the torque transmitting assembly and a second end comprising the one or more follower members, and a shaft assembly operably engaged with a second portion of the torque transmitting assembly on a first end and engaged with a portion of the transfer member on a second end. The first portion or input portion of the torque transmitting assembly may be positioned parallel to, or generally parallel to, the first rotation axis and the second portion or output shaft of the torque transmitting assembly may be positioned parallel to, or generally parallel to, the second rotation axis. The method may comprise expanding and contracting the length of the shaft assembly between each transfer member and each output portion during the selectively varying of the radial distance of the one or more transfer surfaces relative to the first rotation axis. The method may also comprise rotating the one or more transfer surfaces at least partially between the first and second positions when the length of the shaft assemblies between the transfer members and the output portions are expanded and turning the discrete article through the rotation of the transfer surfaces between the first position and the second position. The transfer surfaces, and other portions of the transfer members, may be rotated from the first position into the second position in a first direction of rotation and may be rotated from the second position into the first position in a second direction of rotation. The first direction of rotation may be opposite to the second direction of rotation. In other embodiments, the first direction of rotation may be the same as the second direction of rotation. One or more of the discrete articles may be retained to or pushed from the transfer surfaces using a fluid pressure, such as a negative or a positive fluid pressure, for example.

In one embodiment, the various discrete articles 102 (e.g., a chassis of an absorbent article) or flexible discrete articles 102 may be retained to the various transfer surfaces 136 of the transfer members 112 of the present disclosure in many ways, including but not limited to, fluid pressure, mechanical attachment via pins or grippers, adhesives, such as pressure sensitive or low tack adhesives, static attraction, and/or magnetic attraction, for example. Fluid pressures and/or other forces may also be used to force or move the discrete articles 102 from the transfer surfaces 136 onto a moving carrier member, such as the second moving carrier member 106.

In one embodiment, referring to FIGS. 1, 4-6, 8, 9, 16, and 18, for example, the transfer assembly 100 may comprise a fluid system configured to retain the discrete articles 102 to one or more of the transfer surfaces 136 of the transfer members 112. Each of or one of the transfer members 112 may have one or more fluid ports 230 defined through the transfer surface 136 thereof, or through portions or zones of the transfer surface 136. The fluid ports 230 may have any suitable shape, such as elongate slots, circular or ovate openings, and/or rectangular, square, or triangular openings, for example. The fluid ports 230 may also have mesh, screen, or other porous materials extending thereover. The fluid ports 230 may be linear or non-linear, continuous or non-continuous. In one embodiment, a first transfer member may have a transfer surface having a first pattern of fluid ports and a second transfer member may have a transfer surface having a second pattern of fluid ports. In other embodiments, the patterns on all of the transfer surfaces 136 may be the same. A positive or a negative (vacuum) fluid pressure may be applied to the fluid ports 230 through various fluid conduits and fluid lines. Some fluid ports, at various times, may not have any fluid pressure being applied thereto. The fluid pressures may initiate in one or more fluid movement devices or sources 232, 234, such as one or more fluid pumps, vacuum pumps, pressure blowers, or fans. The fluid may be air or other gas, for example. Some fluid ports 230 may be configured to provide a positive pressure, while at the same time, other fluid ports 230 of the same transfer member 112 may be configured to provide a negative pressure or no fluid pressure. In various embodiments, some of the fluid ports 230 may be configured to provide a first fluid pressure (positive or negative), while at the same time, other fluid ports 230 of the same transfer member 112 may be configured to provide a second fluid pressure (positive or negative). The first fluid pressure may be greater than or less than the second fluid pressure. In other various embodiments, the fluid ports 230 in one transfer member 112 may have a different fluid pressure as the fluid ports 230 in another transfer member 112 on the same transfer assembly 100 owing to factors like the number of the fluid ports 230 or the areas of the fluid ports 230 on a particular transfer surface 136. For example, one fluid pressure may be applied at a pick-up zone and another fluid pressure may be applied at a drop-off zone. In other embodiments, the fluid pressure applied to the fluid ports 230 may vary in different fluid ports 230 or zones of the fluid ports 230 in a transfer member 112 at the pick-up zone and at the drop-off zone.

In various embodiments, referring to FIGS. 1 and 4-9, the fluid system used to provide the fluid pressure to the fluid ports 230 may comprise the first fluid movement device 232 and the second fluid movement device 234. The first and second fluid movement devices 232 and 234 may supply a positive fluid pressure and/or a negative fluid pressure to first and second fluid lines 236 and 238. In one embodiment, the first and second fluid movement devices 232 and 234 may be controlled independently or controlled together for various applications. In one embodiment, only one fluid movement device may be provided. That single fluid movement device may be configured to supply the first and second fluid lines 236 and 238 with positive and/or negative fluid pressures. The fluid pressure and flow rates applied to the first and second fluid lines 236 and 238 may be equal or different. In one embodiment, the single fluid movement device may supply a positive pressure to the first fluid line 236 and a negative pressure to the second fluid line 238, for example.

Figure 21:
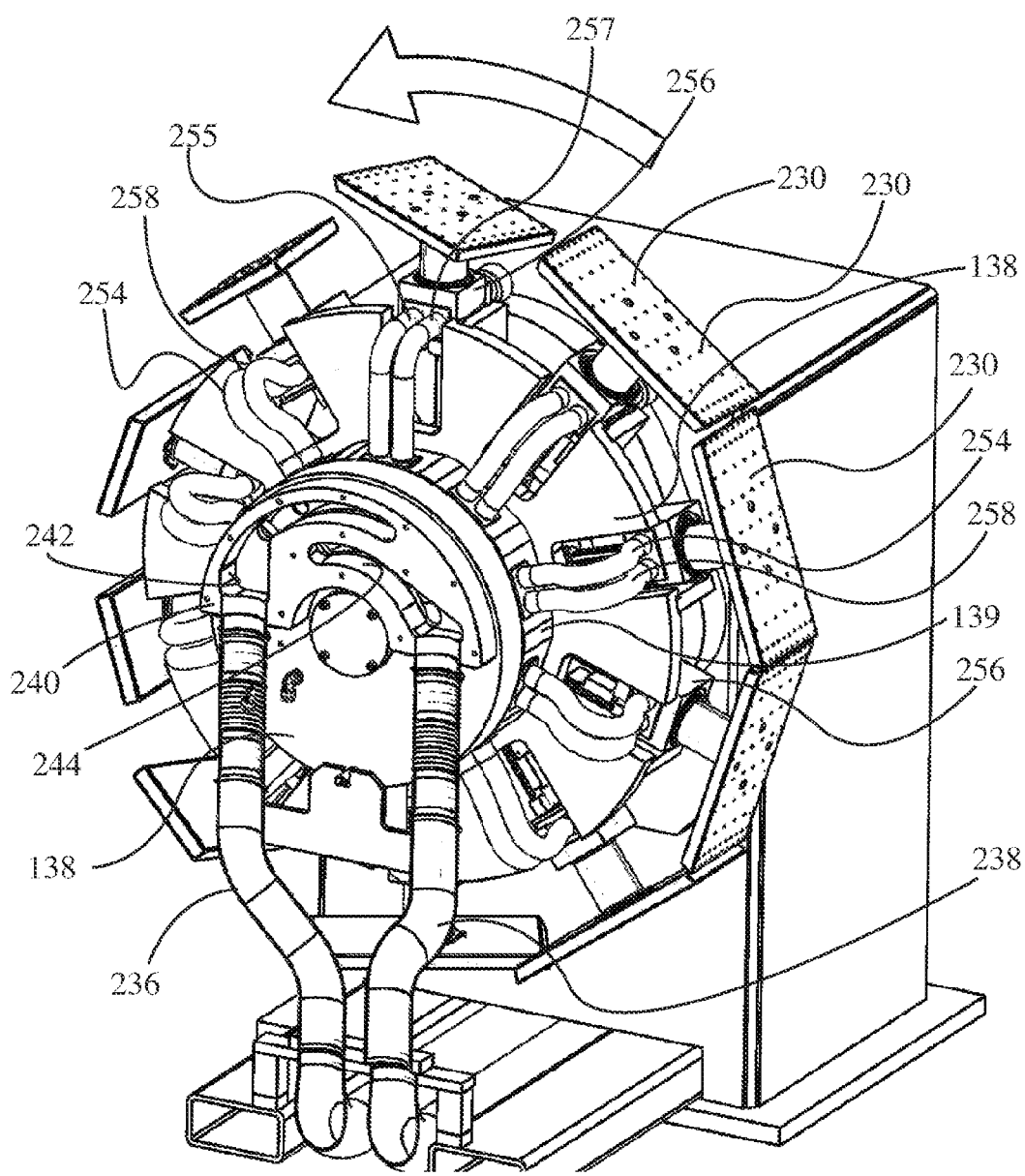
FIG. 21 is a perspective view of a transfer assembly with a portion of a fluid receiving manifold cut away in accordance with one non-limiting embodiment.
Figure 22:
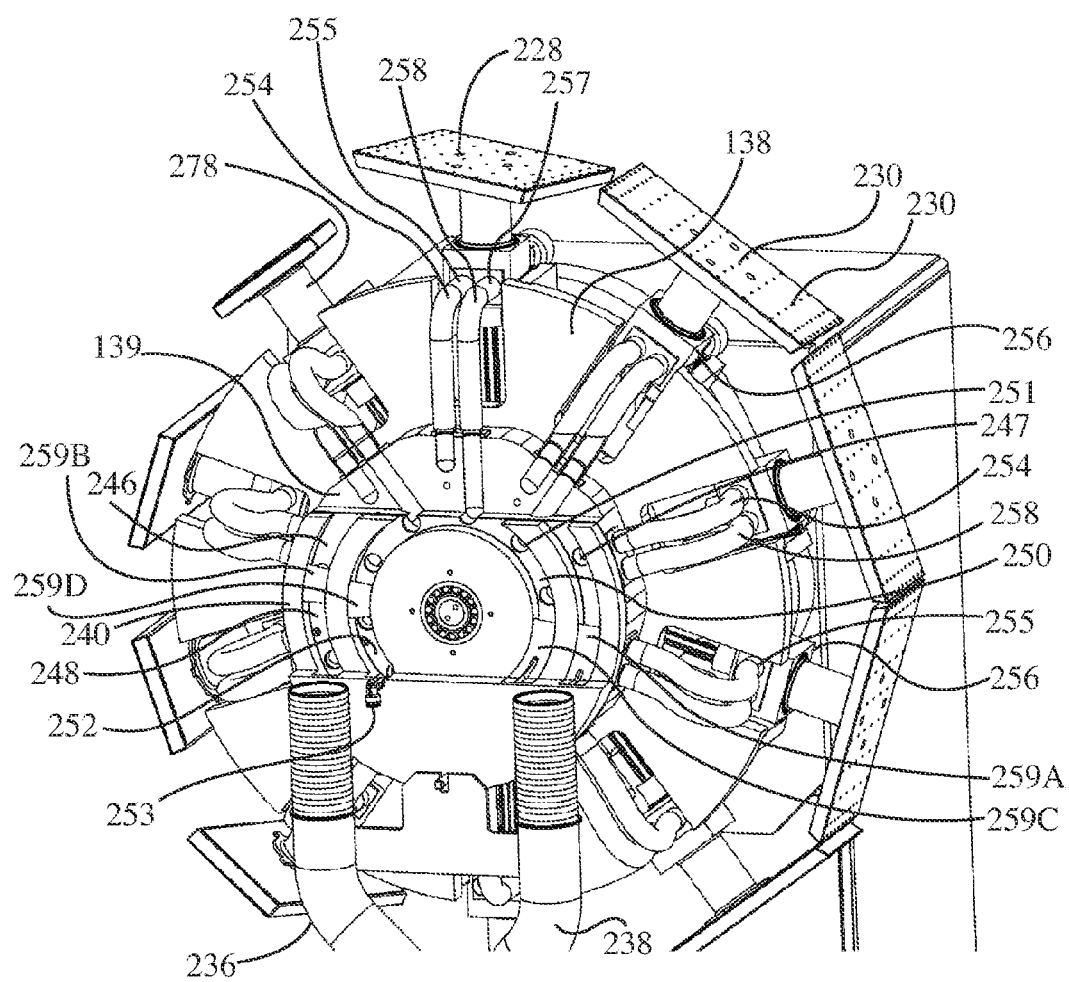
FIG. 22 is a perspective view of a transfer assembly with a portion of the fluid receiving manifold cut away and a portion of the fluid distribution disk cut away in accordance with one non-limiting embodiment.
Figure 23:
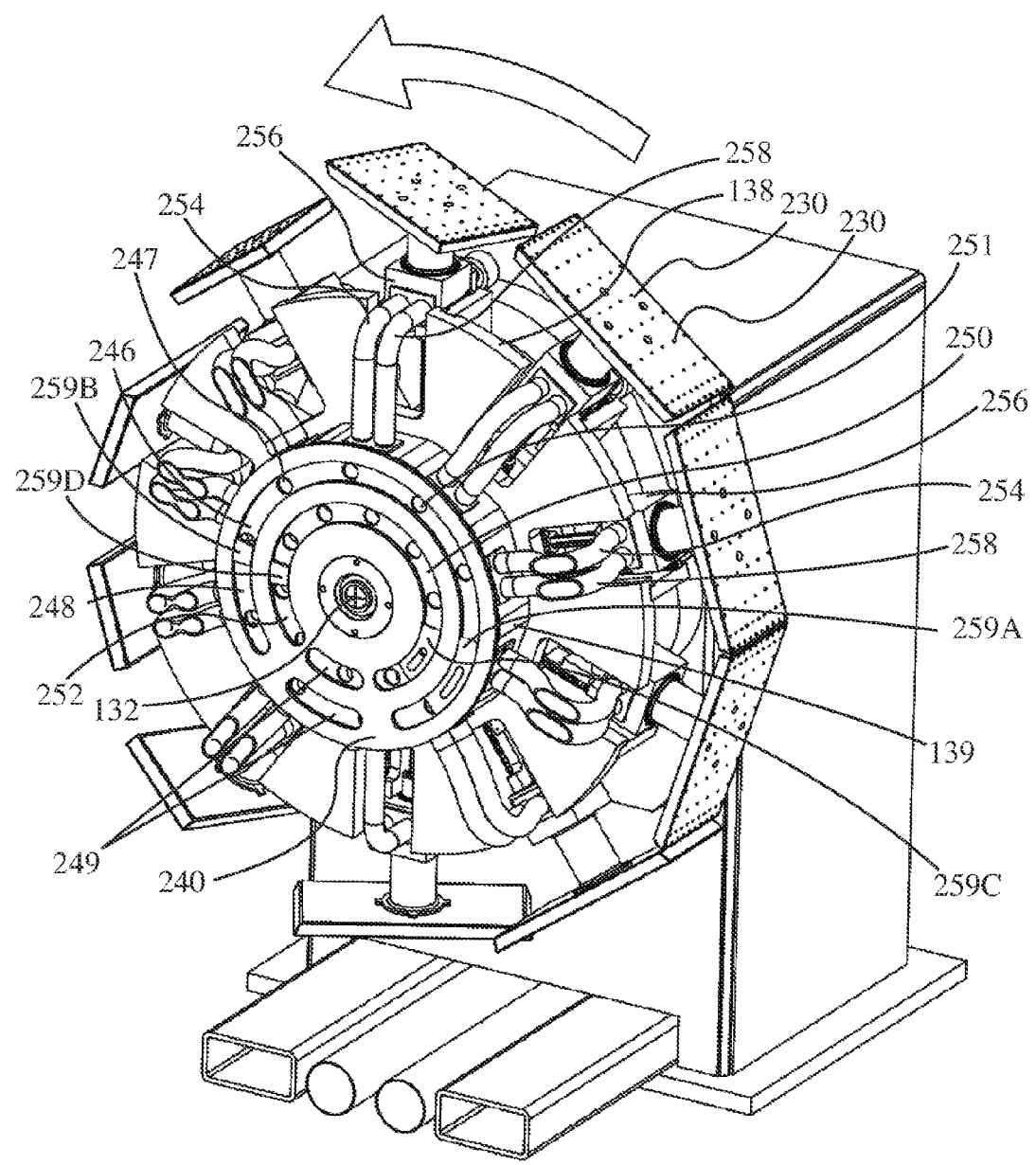
FIG. 23 is a perspective view of a transfer assembly with a portion of the fluid receiving manifold cut away in accordance with one non-limiting embodiment.

In one embodiment, referring to FIGS. 1, 4-6, 9, and 21-23, the first and second fluid lines 236 and 238 may extend from the first and second fluid movement devices 232 and 234 (or one fluid movement device) to a fluid receiving manifold 240 on the transfer assembly 100 and engaged with a portion of the fluid distribution disk 139 in a non-rotating fashion. The fluid distribution disk 139 may be attached to or integral with the wheel 138 and rotates with the wheel 138 about the first rotation axis 132. The fluid receiving manifold 240 has portions thereof cut away in FIG. 21 for illustration, but is illustrated in full in FIGS. 3, 4, and 9. FIG. 22 illustrates portions of the fluid receiving manifold 240 and portions of the fluid lines 236 and 238 cut away for illustration and FIG. 23 illustrates the entire fluid receiving manifold 240 and portion of the fluid lines 236 and 238 cut away to illustrate the details of the fluid distribution disk 139. The fluid receiving manifold 240 is sealably engaged with a portion of the fluid distribution disk 139 such that fluid may be transferred to the appropriate portions of the fluid distribution disk 139. The fluid receiving manifold 240 and/or a portion of the fluid distribution disk 139 may comprise a material configured to seal fluid between the facing portions of the fluid receiving manifold 240 and the portion of the fluid distribution disk 139, while allowing the fluid distribution disk 139 to rotate relative to the stationary fluid receiving manifold 240. Stated another way, the fluid distribution disk 139 may rotate relative to a face of the fluid receiving manifold 240, while fluid pressures are transferred to portions of the fluid distribution disk 139. In one example, such a material may comprise a low friction, low wearing face material such as POLYSLICK UHMW®, TEFLON®, DELRIN®, or GARLOCK®. The first and second fluid lines 236 and 238 may be attached to ports or other connectors on the fluid receiving manifold 240. Referring to FIG. 23, certain regions 249 of the fluid receiving manifold 240 may be provided with a positive pressure to clean the ports in the transfer surfaces 136, for example.

In one embodiment, referring to FIG. 21, the fluid receiving manifold 240 may comprise a first port 242 and a second port 244 defined therein. The first port 242 may be in fluid communication with the first fluid line 236 and, thereby, the first fluid movement device 232. Likewise, the second port 244 may be in fluid communication with the second fluid line 238 and, thereby, the second fluid movement device 234. As such, the first fluid movement device 232 may supply fluid flow to the first port 242 and the second fluid movement device 234 may supply fluid flow to the second port 244. In one embodiment, the first fluid movement device 232 may supply fluid flow to the first port 242 and the second port 244 (e.g., a negative fluid pressure) and, likewise, the second fluid movement device 234 may supply fluid flow to the first port 242 and the second port 244 (e.g., a negative fluid pressure). Referring to FIGS. 22 and 23, the fluid distribution disk 139 may comprise a first channel comprising a first portion 246 and a second portion 248. The first channel may be in fluid communication with the first port 242 and the first fluid line 236. The first portion 246 may be used for applying a negative fluid pressure to at least some of the fluid ports 230 and the second portion 248 may be used for applying a positive fluid pressure to at least some of the fluid ports 230. The application of the positive fluid pressure to at least some of the fluid ports 230 may be known as "blow off" of the discrete articles 102. Blow off may occur when the discrete articles 102 are being transferred to the second moving carrier member 106, for example. Positive pressure may be applied to the second portion 248 by a compressed air source or another fluid movement device (not illustrated). In various embodiments, either of the first and second portions 246 and 248 may be used to apply a positive and/or a negative fluid pressure to at least some of the fluid ports 230.

Referring again to FIGS. 22 and 23, the fluid distribution disk 139 may comprise a second channel comprising a first portion 250 and a second portion 252. The second channel may be in fluid communication with the second port 244 in the fluid distribution disk 139 and the second fluid line 238. The first portion 250 may be used for applying a negative fluid pressure to at least some of the fluid ports 230 and the second portion 252 may be used for applying a positive fluid pressure to at least some of the fluid ports 230. Positive pressure may be applied to the second portion 252 by a compressed air source or another fluid movement device through an air fitting 253. In various embodiments, either of the first and second portions 250 and 252 may be used to apply a positive and/or a negative fluid pressure to at least some of the fluid ports 230. The second channel may be positioned closer to the rotation axis 132 than the first channel. Stated another way, the second channel, or at least portions thereof, may be surrounded by the first channel, or at least portions thereof. In one embodiment, the first channel including the first and second portions 246 and 248 are formed in an arcuate shape centered around the rotation axis 132. The second channel including the first and second portions 250 and 252 are formed in a concentric arcuate shape of a smaller radius. The first channel including first and second portions 246 and 248 on the stationary fluid receiving manifold 240 may be in fluid communication with distribution ports 247 on the rotating fluid distribution disk 139. The second channel including the first and second portions 250 and 252 on the fluid receiving manifold 240 may be in fluid communication with the distribution ports 251 on the fluid distribution disk 139.

In one embodiment, the distribution ports 247 in the fluid distribution disk 139 may be in fluid communication with one or more first fluid conduits 254 extending intermediate the distribution ports 247 and a port 255 on one or more fluid manifolds 256. Each of the fluid manifolds 256 may be in fluid communication with the fluid ports 230 on the transfer members 112. The fluid manifolds 256 may be mounted to or formed with bases 141 which may be movably or slidably mounted to the plates 155 (see e.g., FIGS. 10 and 16-18) such that the fluid manifolds 256 and the bases 141 may move or slide radially relative to the rotation axis 132 on the plates 155. The fluid manifolds 256 and the bases 141 may be portions of the transfer members 112. In one embodiment, the base 141 may comprise one or more grooves, linear bearings, or linear bushings that may be configured to engage one or more linear, or substantially linear, rails, or tracks on the plates 155. In other embodiments, the linear bearings or linear bushings may be defined in the plates 155 and the tracks may be defined in the base 141. As a result, when the follower members 142 are moved radially by the track 134, the fluid manifolds 256 and the bases 141 may also be moved radially and slide or move relative to the plate 155 owing to the movable or slidable engagement between the bases 141 and the plates 155. In one embodiment, the distribution ports 251 in fluid distribution disk 139 may be in fluid communication with one or more second fluid conduits 258 extending intermediate the distribution ports 251 and a port 257 on the one or more fluid manifolds 256. As a result of the fluid receiving manifold 240, including the distribution ports 247 and 251, the first and second fluid conduits 254 and 258, fluid from the first and second fluid lines 236 and 238, may be provided to the fluid manifold 256, while the fluid manifolds 256 are rotating about the first rotation axis 132 and being moved radially relative to the first rotation axis 132 by the track 134.

In one embodiment, referring to FIGS. 21-25, the first and second fluid conduits 254 and 258 may be able to tolerate radial movement of the fluid manifold 256 while still being in fluid communication with the various zones. The first and second fluid conduits 254 and 258 may be flexible and comprise flexible hose or lines. The bent geometry of the fluid conduits 254 and 258 may allow for a full range of radial motion without a change in the length of the fluid conduits 254 and 258. Alternatively, the fluid conduits 254 and 258 may be extensible so the fluid conduits 254 and 258 may stretch and/or compress to adjust for the radial movement. The fluid conduits 254 and 258 may be constructed of many compliant materials. Some examples materials are rubber, vinyl, plastic, and/or corrugated metal. Support structures, such as a wire helix, for example, may be provided within or on sidewalls of the fluid conduits 254 and 258 may be helpful in avoiding, or at least inhibiting, the fluid conduits 254 and 258 from collapsing when a negative pressure is present within the fluid conduits 254 and 258 at points during operation of the fluid system. Other methods of achieving fluid communication with the radially moving fluid manifold 256 are also within the scope of the present disclosure. The fluid conduits 254 and 258 may also comprise hollow tubes that move axially from a sealed manifold or telescoping tubes. In one embodiment, a moving fluid conduit may enable fluid communication by sliding past another fluid manifold with side passages.

In various embodiments, referring to FIGS. 22 and 23, the angular position of first and second channels (shown as arcuate channels) in the fluid receiving manifold 240 may control when fluid pressure is applied to various transfer members 112 and transfer surfaces 136. The timing of when negative pressure may be available to the first fluid conduit 254 so that vacuum may be provided to the leading portion of the transfer surface 136 may be controlled by the location of divider 259A. Adjusting the position of the divider 259A counterclockwise may delay or retard the provision of the vacuum to the transfer surface 136, while adjusting the position of the divider 259A clockwise may hasten the provision of the vacuum to the transfer surface 136. The negative pressure or vacuum may be maintained as the fluid distribution disk 139 rotates from the divider 259A to the divider 259B within the first portion 246. The location of the divider 259B may determine the timing of when the first fluid conduit 254 has the negative pressure turned off and positive pressure from the second portion 248 turned on. The positive pressure may blow or force the leading portion of the discrete article 102 from the transfer surface 136. Likewise, the location of dividers 259C and 259D may adjust the timing of the provision of a positive or negative pressure for the second fluid conduit 258 and, thereby the trailing portions of the transfer surface 136 and the discrete articles 102 positioned thereon. These features may enable independent timing control to different portions (e.g., leading and trailing portions) of the transfer members 112 and transfer surfaces 136.

Figure 24:
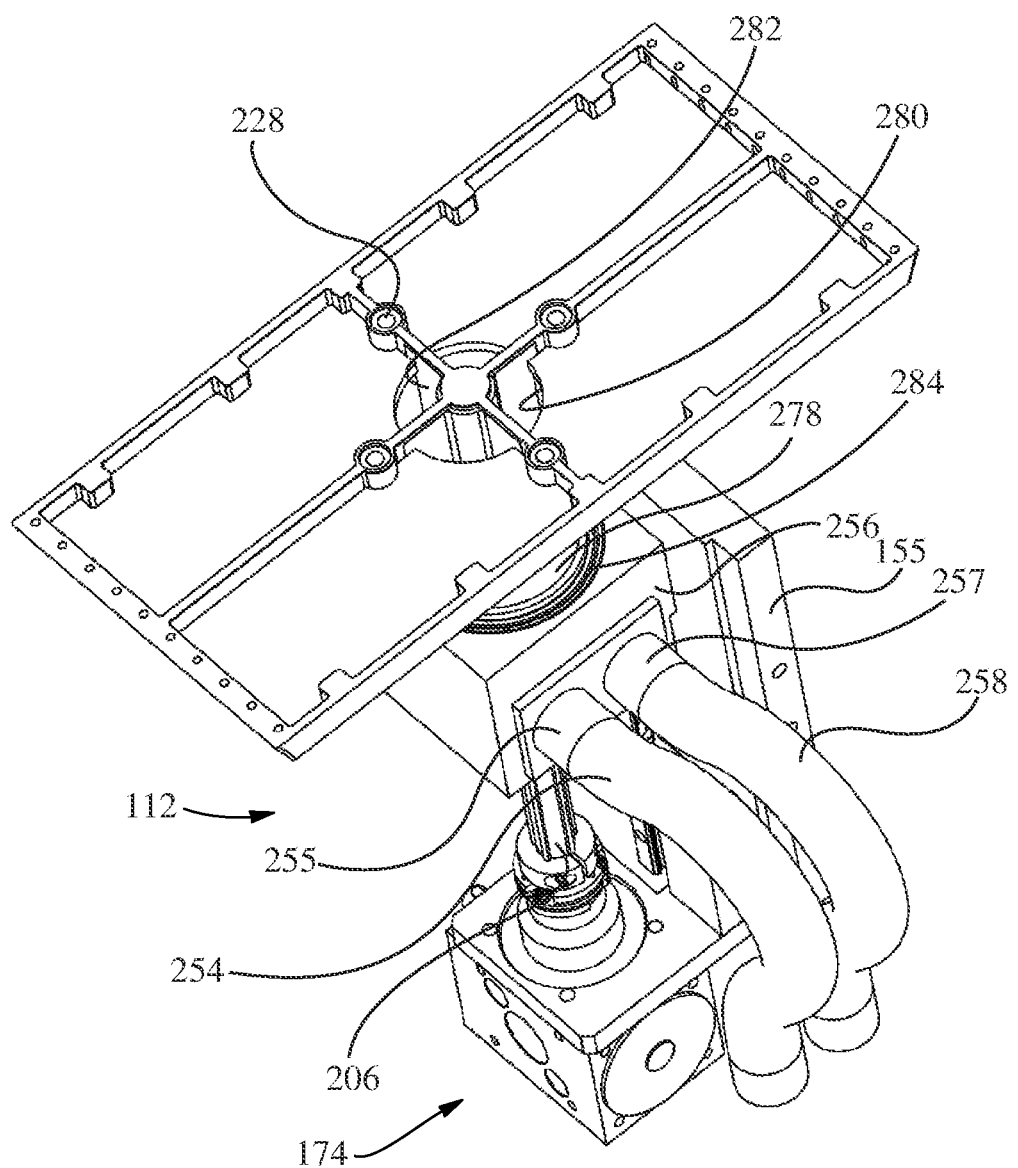
FIGS. 24-26 are perspective views of a portion of the fluid system of a transfer member of the present disclosure in accordance with various non-limiting embodiments.
Figure 25:
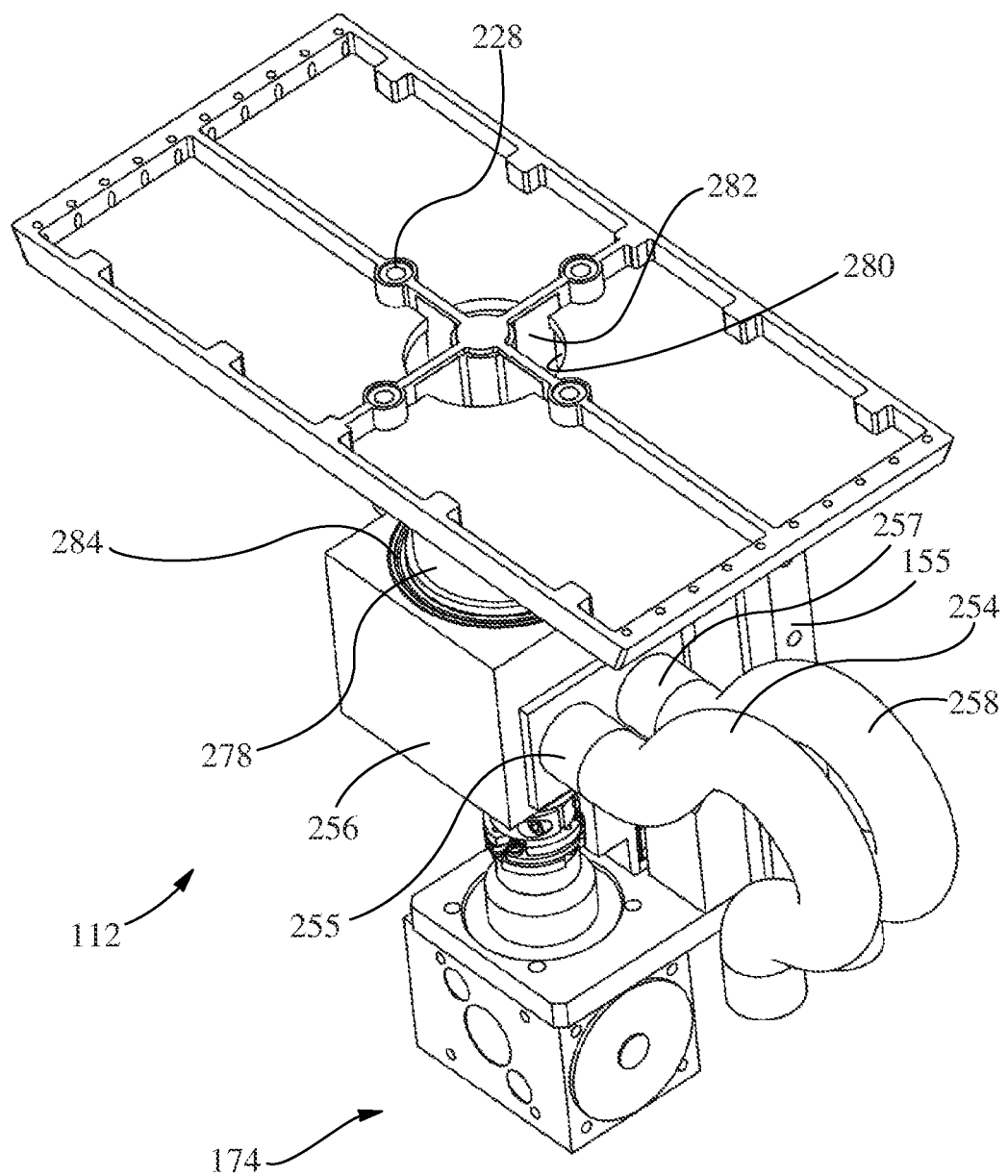
Figure 26:
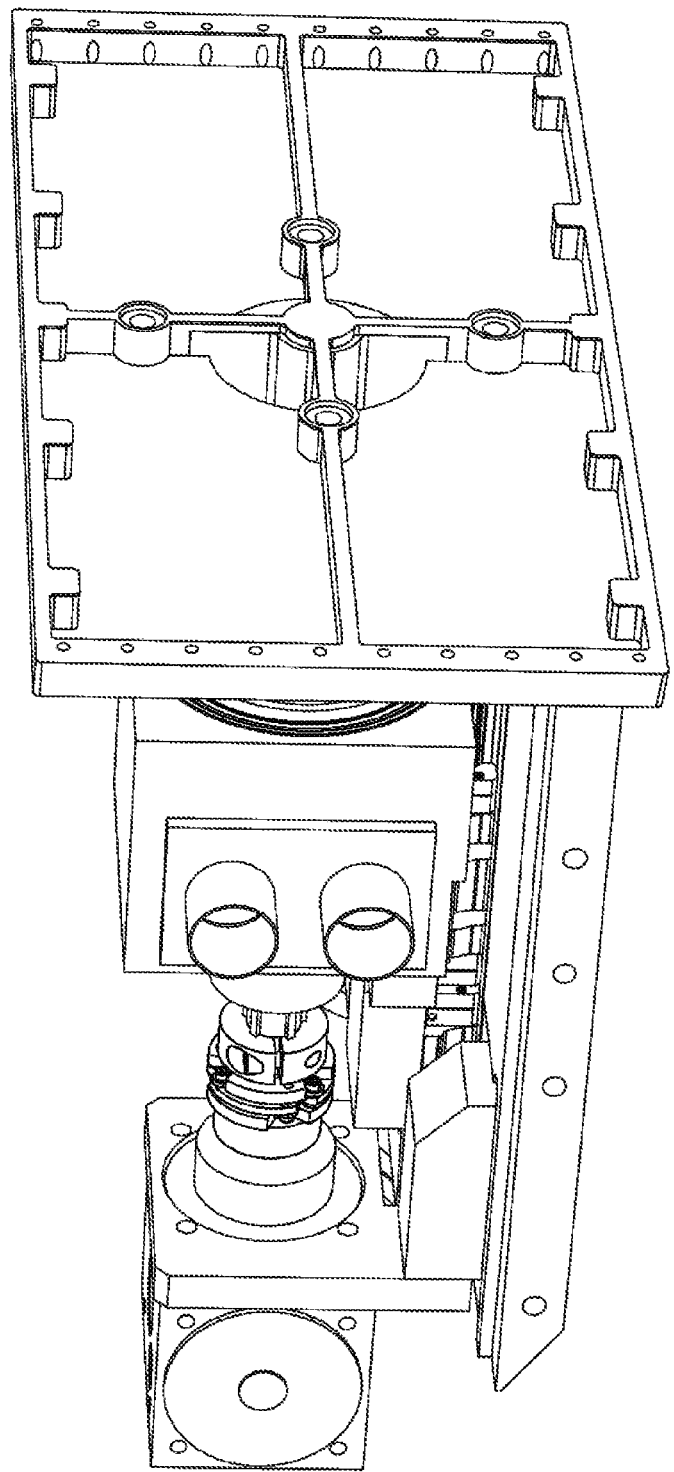

In one embodiment, referring to FIGS. 24-26, portions of the rotation assembly 170 and portions of a transfer member 112, including a fluid system of the transfer member 112, are illustrated. In FIGS. 24-26, the transfer surfaces 136 are removed for illustration of the various zones in portions of the transfer members 112. FIGS. 24 and 25 illustrate the portions of the rotation assembly 170 and portions of the transfer member 112 with the first and second fluid conduits 254 and 258 attached to the ports 255 and 257, while FIG. 26 has the first and second fluid conduits 254 and 258 removed from the ports 255 and 257 for illustration. In FIG. 24, the transfer surface 136, and other portions of the transfer member 112, are in the first position 116, while in FIGS. 25 and 26, the transfer surface 136, and other portions of the transfer member 112, are in the second position 118. FIG. 26 illustrates the track on the plate 155 to which the base 114 is movably or slidably engaged.

Figure 27:
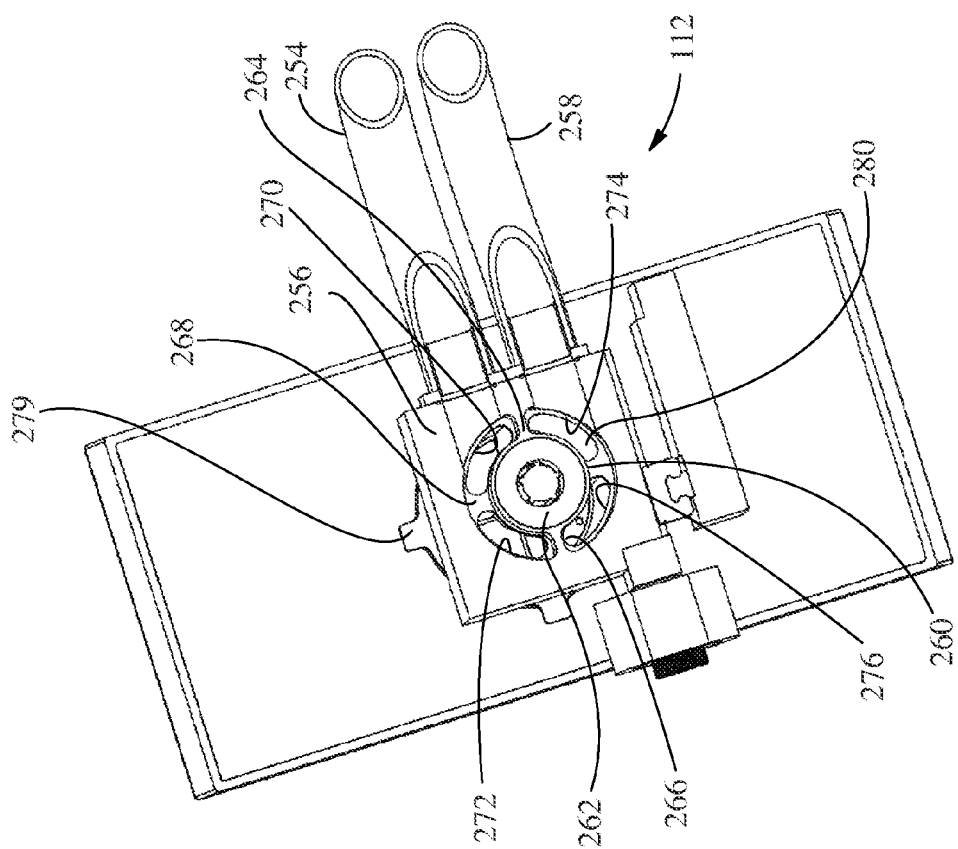
FIGS. 27-29 are bottom perspective cut-away views of a portion of the fluid system of a transfer member of the present disclosure in accordance with various non-limiting embodiments.
Figure 28:
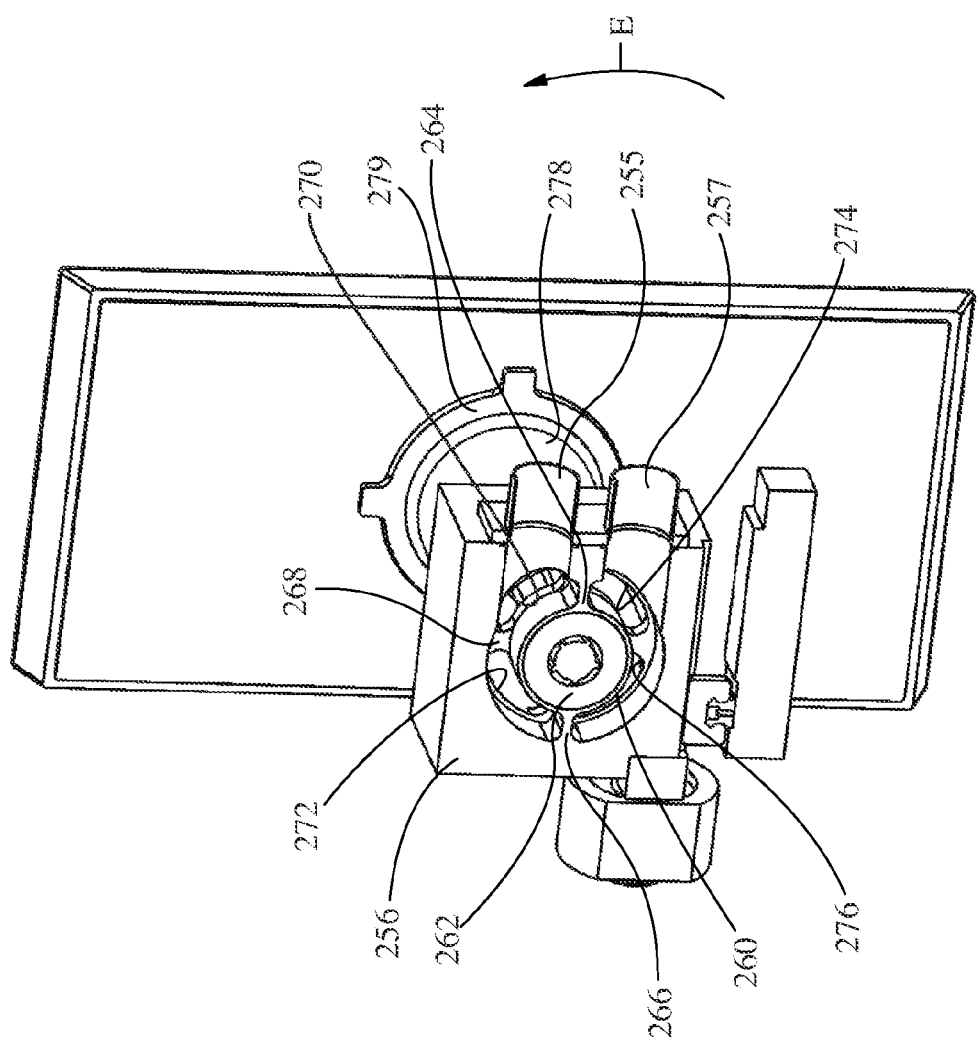
Figure 29:
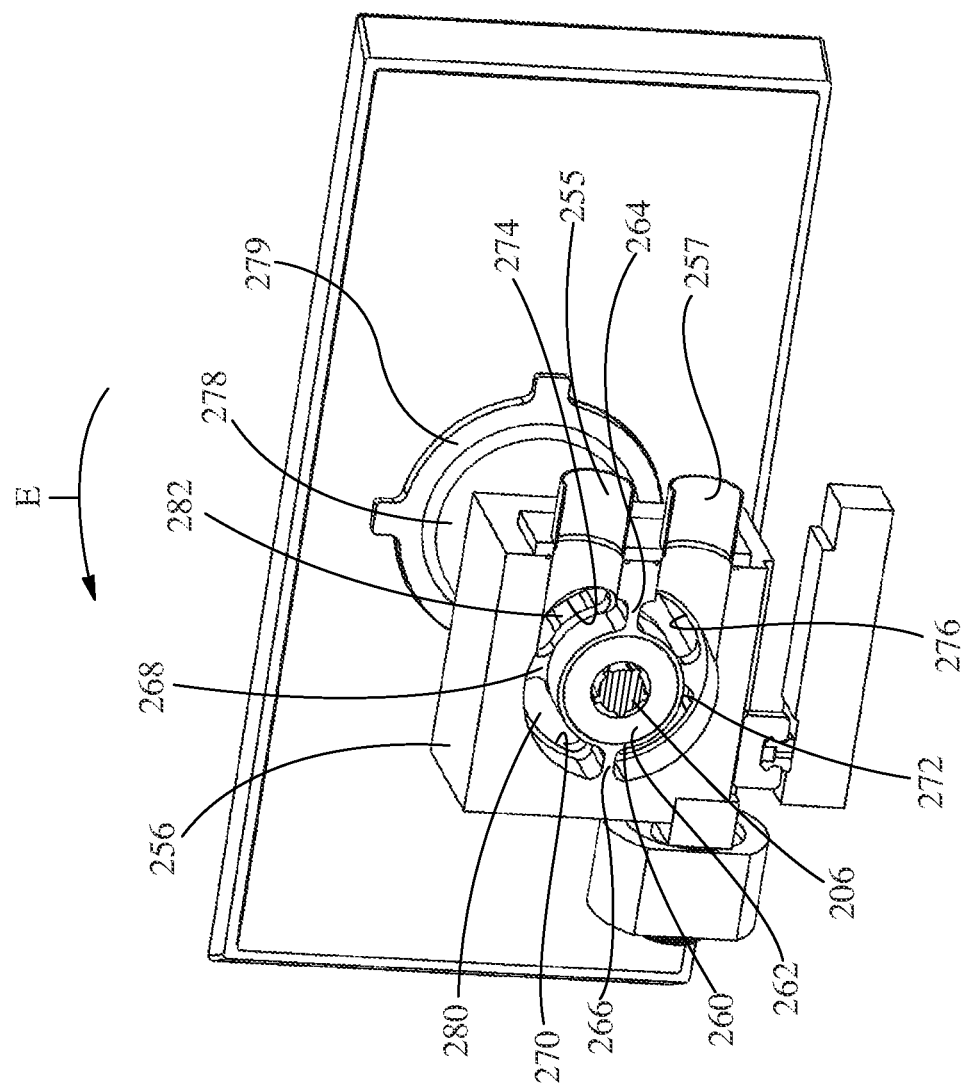
Figure 30:
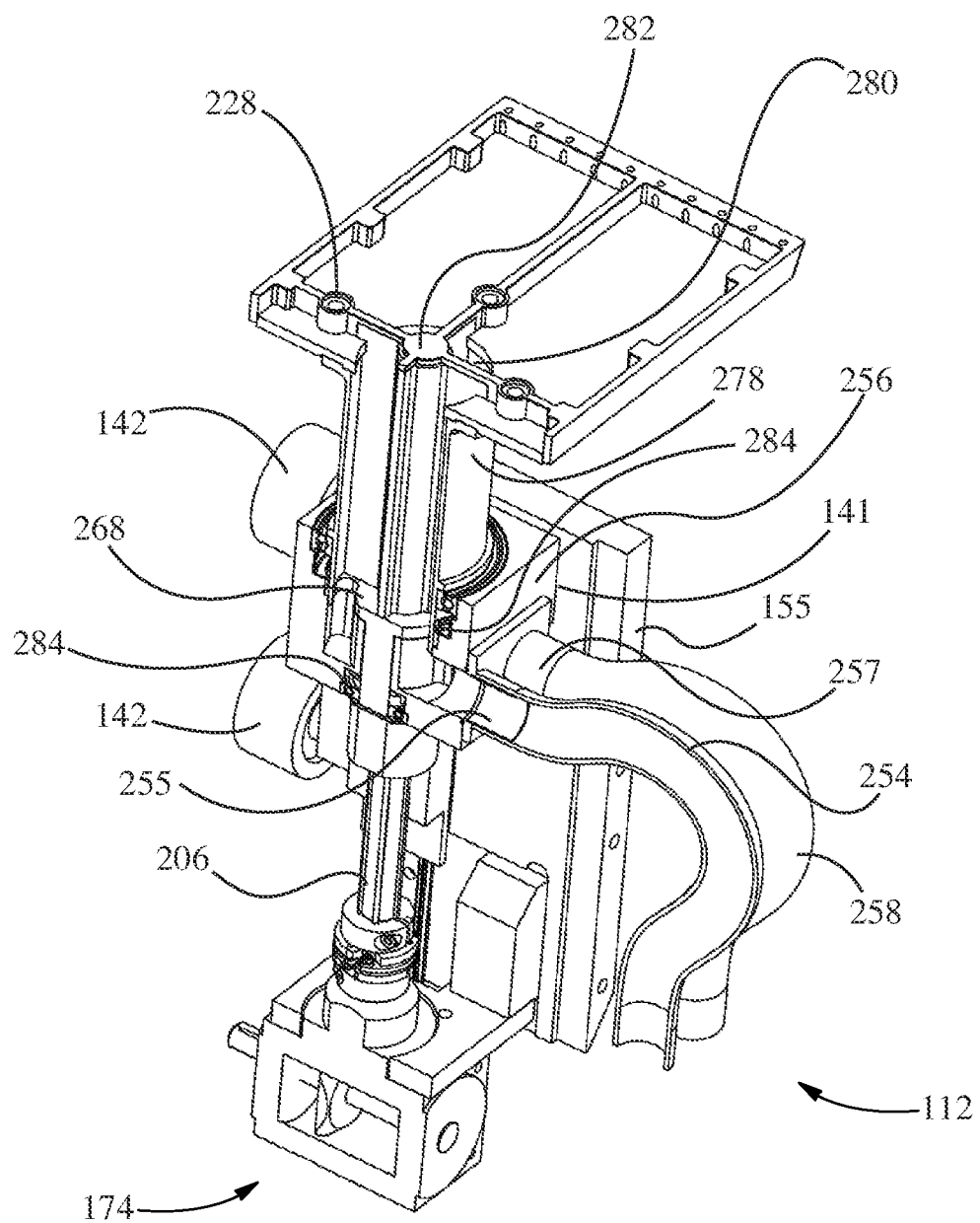
FIG. 30 is a cut away perspective view of a portion of the fluid system of a transfer member of the present disclosure with portions of the transfer member in the first position in accordance with one non-limiting embodiment.
Figure 31:
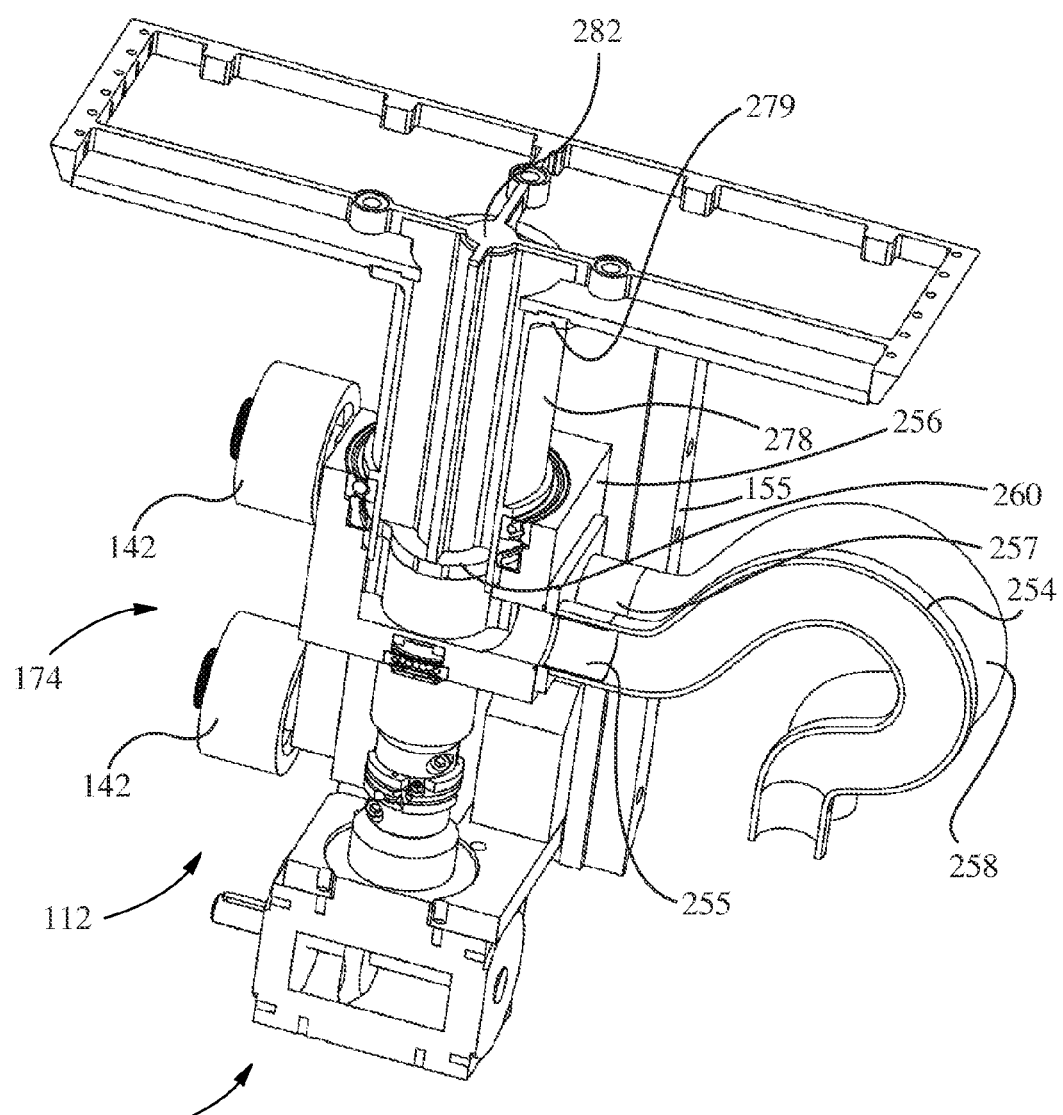
FIG. 31 is a cut away perspective view of a portion of the fluid system of a transfer member of the present disclosure with portions of the transfer member in the second position in accordance with one non-limiting embodiment.
Figure 32:
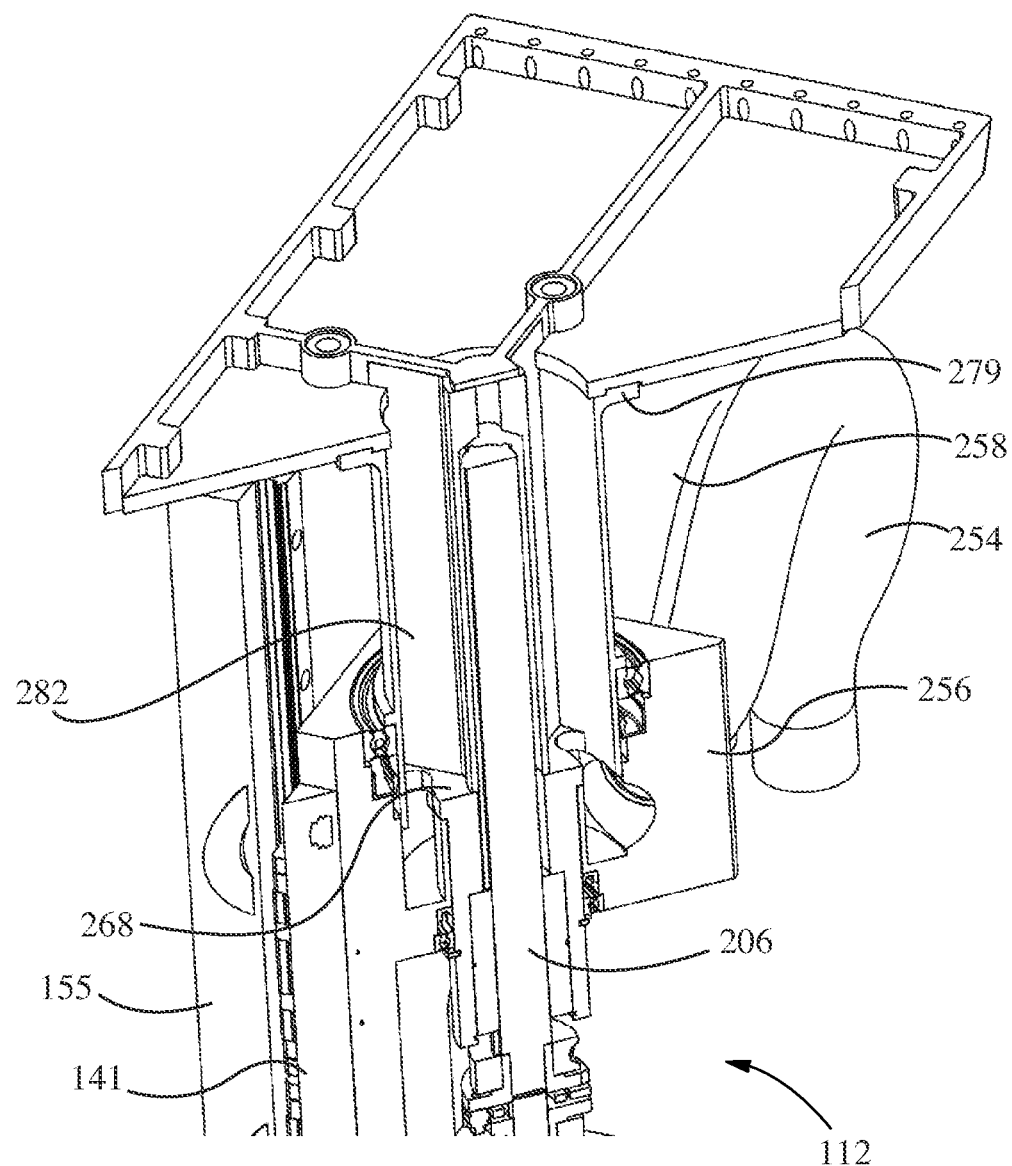
FIG. 32 is another cut away perspective view of a portion of the fluid system of a transfer member of the present disclosure with portions of the transfer members in the second position in accordance with one non-limiting embodiment.

In one embodiment, referring to FIGS. 27-29, bottom perspective cut away views of the fluid manifold 256 are illustrated. In FIGS. 27 and 28, the transfer surface 136, and other portions of the transfer member 112, are the first position 116, while in FIG. 29, the transfer surface 136, and other portions of the transfer member 112 are in the second position 118. The fluid manifold 256 may be configured to receive the shaft 200 or the spline 206 through a central portion 262 thereof. The central portion 262 may rotate in both the clockwise direction and the counterclockwise direction when rotated by the shaft 200 or the spline 206. The central portion 262 may be surrounded by a frame 260 that may have a first wall 264 extending in a first direction and a second wall 266 extending in a second direction. In one embodiment, the first wall 264 may extend in an opposite, or generally opposite, direction as the second wall 266. The walls 264 and 266 and the frame 260 may be configured to separate fluid flow from the first fluid conduit 254 from fluid flow from the second fluid conduit 258. It is to be noted that the fluid manifold 256, the frame 260, and the first and second fluid conduits 254 and 258 may not, or do not, rotate when portions of the transfer member 112 are rotated between the first position 116 and the second position 118, but that the central portion 262, the housing 278, and the plate 268 may rotate with the shaft 200 or the spline 206. The housing 278 may be attached to or formed with a plate 268 having four or more openings defined therein; a first opening 270, a second opening 272, a third opening 274, and a fourth opening 276. The openings may have any suitable shape and/or area and the various openings may have different shapes and/or areas as other openings. In one embodiment, all of the openings may have the same shape and/or area. When the transfer member 112 is in the first position 116, the first fluid conduit 254 may be in fluid communication with the first opening 270 and the second opening 272 of the plate 268 and the second fluid conduit 258 may be in fluid communication with the third opening 274 and the fourth opening 276. When the transfer member 112 is in the second position 118, the first fluid conduit 254 may be in fluid communication with the first opening 270 and the third opening 274 of the plate 268 and the second fluid conduit 258 may be in fluid communication with the second opening 272 and the fourth opening 276.

In one embodiment, referring to FIGS. 24-32, the transfer member 112 may comprise a housing 278. In one embodiment, the housing 278 may comprise a flange 279 on a portion of the housing 278 most proximal to the bottom surface of the transfer member 112. This flange 279 may be bolted to the distal portion of transfer member 112 by engaging bolts with the bolt holes 228 to engage the distal portion of the transfer member 112 and the housing 278. Other fastening elements may also be used. In one embodiment, the housing 278 may be sealably engaged with the distal portion of the transfer member 112, such as by positioning a seal intermediate a portion of the distal portion of the transfer member 112 and the flange 279. The housing 278 may also be formed with the distal portion of the transfer member 112. The housing 278 may be configured to maintain one or more fluid pressures therein and may define a chamber 280 having a divider 282 positioned therein. The divider 282 may be positioned within the chamber 280 or may be formed with the housing 278. The housing 278 may be sealably engaged with the fluid manifold 256 using seals 284, other members, or compounds so that fluid may transfer from the fluid manifold 256 to the housing 278. Fluid may be transferred from the fluid manifold 256 to the housing 278 at the interface of the plate 268 and the frame 260. A small clearance or contact between the plate 268 and the frame 260 may minimize leakage. The divider 282 may divide the chamber 280 into four or more areas. Each of the four or more areas of the chamber 280 may be in fluid communication with at least one zone of the distal portion of the transfer member 112, and zones thereof, and with fluid ports 230 in the transfer surface 136. The zones on the distal portion of the transfer members 112 will be discussed in further detail below. The housing 278, the divider 282, and the distal portion of the transfer member 112 may rotate in unison when portions of the transfer member 112 are rotated between the first position 116 and the second position 118. The shaft 200 or the spline 206 may be engaged with the divider 282, which may be attached to or formed with the housing 278 and the distal portion of the transfer member 112 so that the assembly may rotate between the first position 116 and the second position 118. The housing 278, the divider 282, the plate 268, and the distal portion of the transfer member 112 may all rotate relative to the fluid manifold 256 and the frame 260. The plate 268 may be positioned proximate to the divider 282 or the divider 282 may be abutted with the plate 268. In one embodiment, the divider 282 may be sealably engaged with the plate 268, using a seal or other member.

Related art fluid systems typically have a fluid pressure in both of the leading and trailing portions of a transfer member either on or off. If the fluid pressure is on in the leading or trailing portions when not needed, energy may be wasted. Furthermore, the fluid pressure in related art transfer members in both of the leading and trailing portions is usually positive or negative, not one negative and one positive. This may create issues during discrete article transfer, especially during transferring the discrete article onto a second moving carrier member. Typically, the discrete article is "blown off" of the transfer member onto the second moving carrier member. To effectuate suitable transfers, this blow off usually has to occur when the leading portion of the discrete article engages the second moving carrier member to begin the transfer. Doing so may cause the transfer member to also blow off the trailing portion of the discrete article and lose control of it prior to the time when the trailing portion is transferred to the second moving carrier member. This can result in fold over of portions of the discrete articles during the transfers or unsuitable transfers (e.g., improper positioning of the discrete articles on the second moving carrier member). This is particularly an issue if the discrete articles have stretched elastic elements that can contract if negative pressure is not maintained prior to the point of transfer. The fluid systems of the present disclosure overcome the disadvantages of the related art fluid systems for transfer assemblies.

By providing the fluid systems in the configuration discussed above, fluid pressure from the first fluid conduit 254 may be maintained on the leading portion of the distal portion of the transfer member 112 regardless of whether the distal portion of the transfer member 112 is in the first position 116 or in the second position 118. Likewise, fluid pressure from the second fluid conduit 258 may be maintained on the trailing portion of the distal portion of the transfer member 112 regardless of whether the distal portion of the transfer member 112 is in the first position 116 or in the second position 118. This provides a significant advantage over the related art, as now the leading and trailing portions of the discrete articles 102 may be independently controlled, regardless of whether the distal portions of the transfer members 112 are in the first position 116 or in the second position 118, leading to more accurate and higher speed transfers. In one embodiment, the first fluid conduit 254 may be in fluid communication with the leading portion of the distal portion of transfer member 112 and the second fluid conduit 258 may be in fluid communication with the trailing portion of the distal portion of the transfer member 112. The distal portion of the transfer member, as referred to herein, is the "head" portion that comprises the transfer surface 136 and the zones. It is located on the distal portion of the transfer member 112 relative to the rotation axis 132.

Also, by providing the fluid systems in the configuration discussed above, less vacuum or other fluid pressure may be used to retain the discrete articles to the transfer surfaces 136 since vacuum may be turned off on the leading or trailing portions when not required. For example, when the leading portion of a transfer surface 136 first engages a discrete article from a first moving carrier member, vacuum in the trailing portion may be off until required. Likewise, after the leading portion of the discrete article is transferred to a second moving carrier member, vacuum in the leading portion of the transfer surface 136 may be turned off. This feature can save energy.

Referring to FIGS. 33-36, one or more of the distal portions of the transfer members 112 may comprise a first zone "1", a second zone "2", a third zone "3", a fourth zone "4", or more than four zones. Although the transfer surface 136 is not illustrated in FIGS. 33-36, each of the zones may comprise fluid ports 230 defined through the transfer surface 136 thereof (see e.g., FIG. 8). The zones may be in fluid communication with the fluid ports 230 within that particular zone. In one embodiment, the transfer surfaces 136 may be sealed to portions of the distal portion of the transfer member 112 defining the zones so that fluid from the zones may pass to and through the fluid ports 230 within that zone. In one embodiment, as described above, the transfer surfaces 136 may be flat, or substantially flat, or may comprise flat or arcuate portions. FIGS. 33-36 illustrate the distal portions of the transfer members 112 in the first position 116. Arrows E and F indicate the two possible directions of rotation of the distal portions of the transfer members 112 into the second position 118 about the shaft 200, the spline 206, and/or the second rotation axis 164. An illustration of how the zones are to be numbered is illustrated in FIGS. 33-36. In all instances, zone 1 will be diagonally across from zone 4 and zone 2 will be diagonally across from zone 3. The leading portions and trailing portions in the direction of rotation about the first rotation axis 132 are labeled "L" and "T," respectively. Note for the embodiments illustrated in FIGS. 3-32, the preferred numbering scheme on a transfer surface 136 is disclosed in FIG. 33 and E is the preferred direction of rotation from the first position 116 into the second position 118.

Again referring to FIGS. 33-36, as a result, the first fluid conduit 254 may be in fluid communication with the leading portion L and the second fluid conduit 258 may be in fluid communication with the trailing portion T of the distal portions of the transfer members 112 regardless of whether the distal portions of the transfer members 112 are rotated in the direction of arrow E or the direction of arrow F. Thus, fluid pressure from the first fluid conduit 254 may be applied to the leading portion L and fluid pressure from the second fluid conduit 258 may be applied to the trailing portion T when the transfer members 112 are in the first position 116 or in the second position 118. This occurs since the housing 278, the divider 282, and the plate 268 rotate in unison with the distal portion of the transfer member 112 between the first position 116 and the second position 118 and the frame 260 remains rotational fixed relative to the rotation of the distal portion of transfer member 112. By providing such a system, a discrete article 102 may receive independent leading portion and trailing portion fluid pressures even after turning of the distal portion of the transfer member 112 about the second rotation axis 164. In such an embodiment, the second rotation axis 164 may be coaxial with the spline 206, for example. In one embodiment, FIG. 37 illustrates the distal portion of the transfer member 112 of FIG. 36 when the distal portion of the transfer member 112 is moved into the second position 118 in the direction of arrow E.

In one embodiment, independent leading portion and trailing portion vacuum control are provided when the transfer members 112 are in the first position 116 or in the second position 118. Thus, independent leading and trailing portion control may be providing during discrete article transfers when such a feature is advantageous. As the transfer member rotates between the first position 116 and the second position 118, there may be some mixing of the leading and trailing portion negative pressure, however, this is not an issue as negative pressure may be applied to both the leading and trailing portions to maintain control of the discrete article 102.

Figure 36:
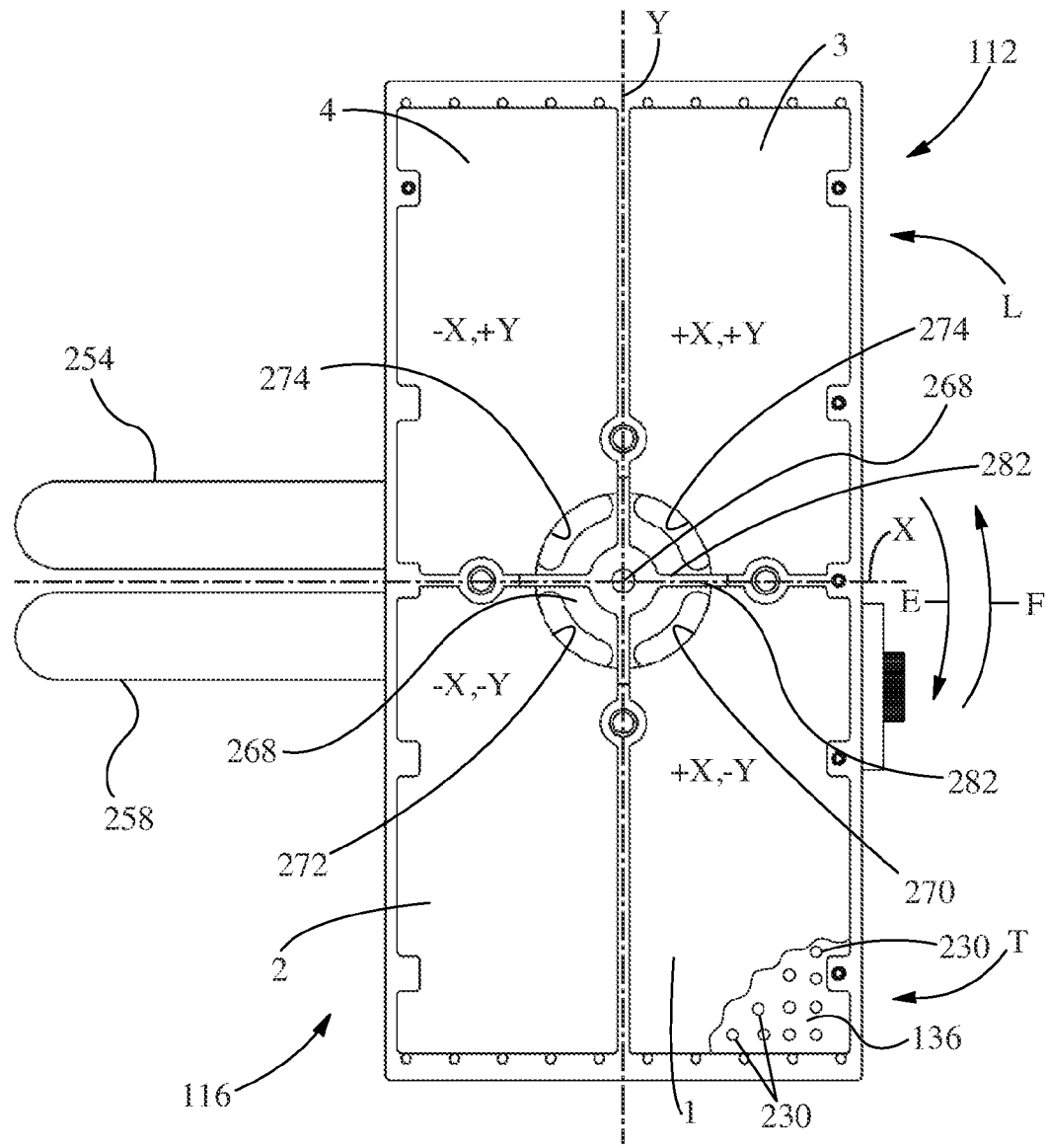

In one embodiment, referring to FIG. 36, for example, although the following may apply to all numbering of the zones, each of or one of the distal portions of the transfer members 112 may have an X-axis and a Y-axis extending thereabout. Both the X-axis and the Y-axis, in one embodiment, may extend through a midpoint 286 of the transfer surface 136. The X-axis may be positioned perpendicular to the Y-axis. The four zones, 1-4, may be four quadrants where the X-axis and the Y-axis define the four quadrants. A point in the first quadrant (zone 1) may have a first Cartesian sign of X and a first Cartesian sign of Y and a point in the fourth quadrant (zone 4) may have a second Cartesian sign of X and a second Cartesian sign of Y. The first Cartesian sign of X may be opposite to the second Cartesian sign of X and the first Cartesian sign of Y may be opposite to the second Cartesian sign of Y. In one embodiment, a point in the second quadrant (zone 2) may have a first Cartesian sign of X and a first Cartesian sign of Y and a point in the third quadrant (zone 3) may have a second Cartesian sign of X and a second Cartesian sign of Y. The first Cartesian sign of X may be opposite to the second Cartesian sign of X and the first Cartesian sign of Y may be opposite to the second Cartesian sign of Y. The Cartesian sign of X in the third quadrant (third zone) may be opposite to the Cartesian sign of X in the fourth quadrant (fourth zone), while the Cartesian sign of Y in the third quadrant may be the same as the Cartesian sign of Y in the fourth quadrant. The Cartesian sign of X in the first quadrant (first zone) may be opposite to the Cartesian sign of X in the second quadrant (second zone), while the Cartesian sign of Y in the first quadrant may be the same as the Cartesian sign of Y in the second quadrant.

Figure 33:
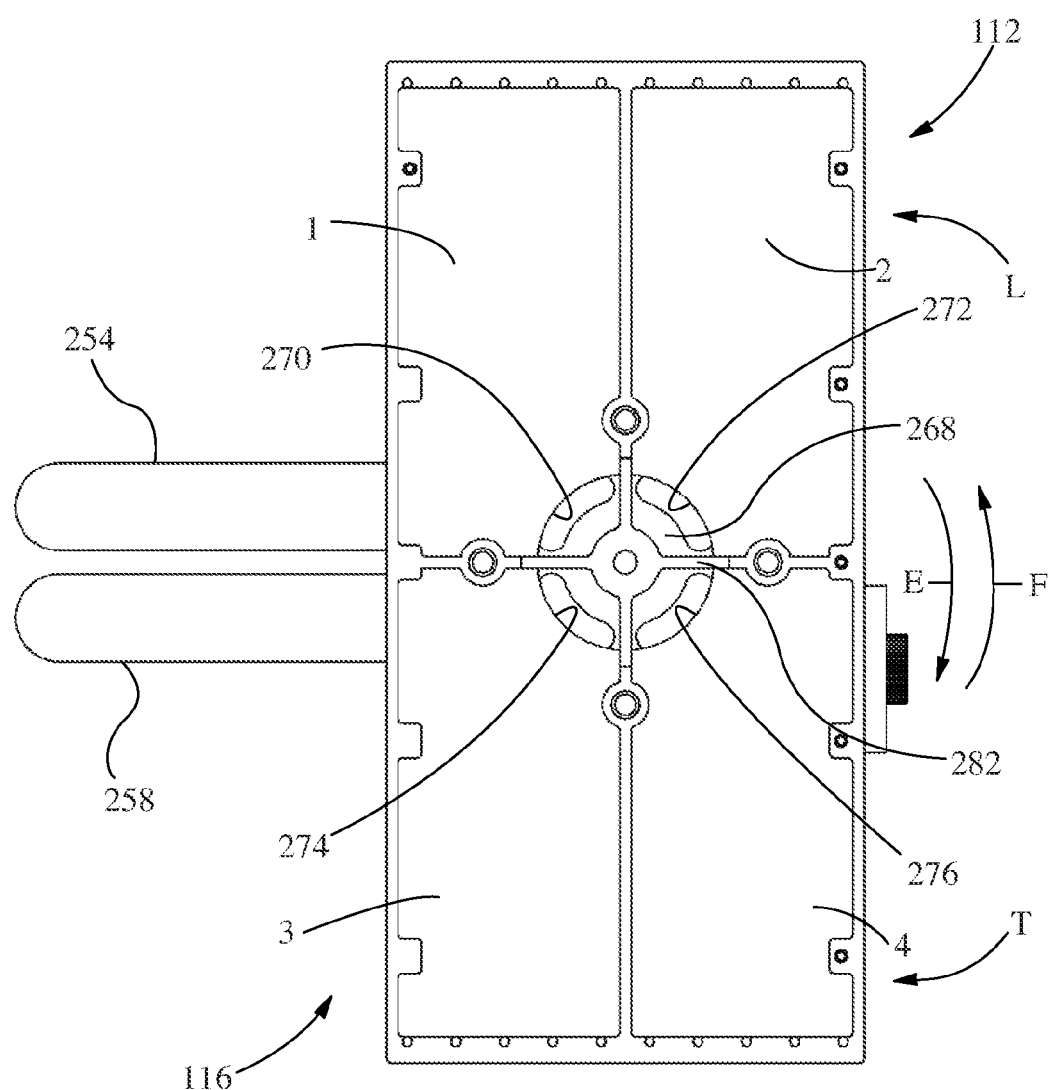
FIGS. 33-36 are top views of zones of a portion of the transfer member with the portion of the transfer member in the first position in accordance with one non-limiting embodiment.
Figure 34:
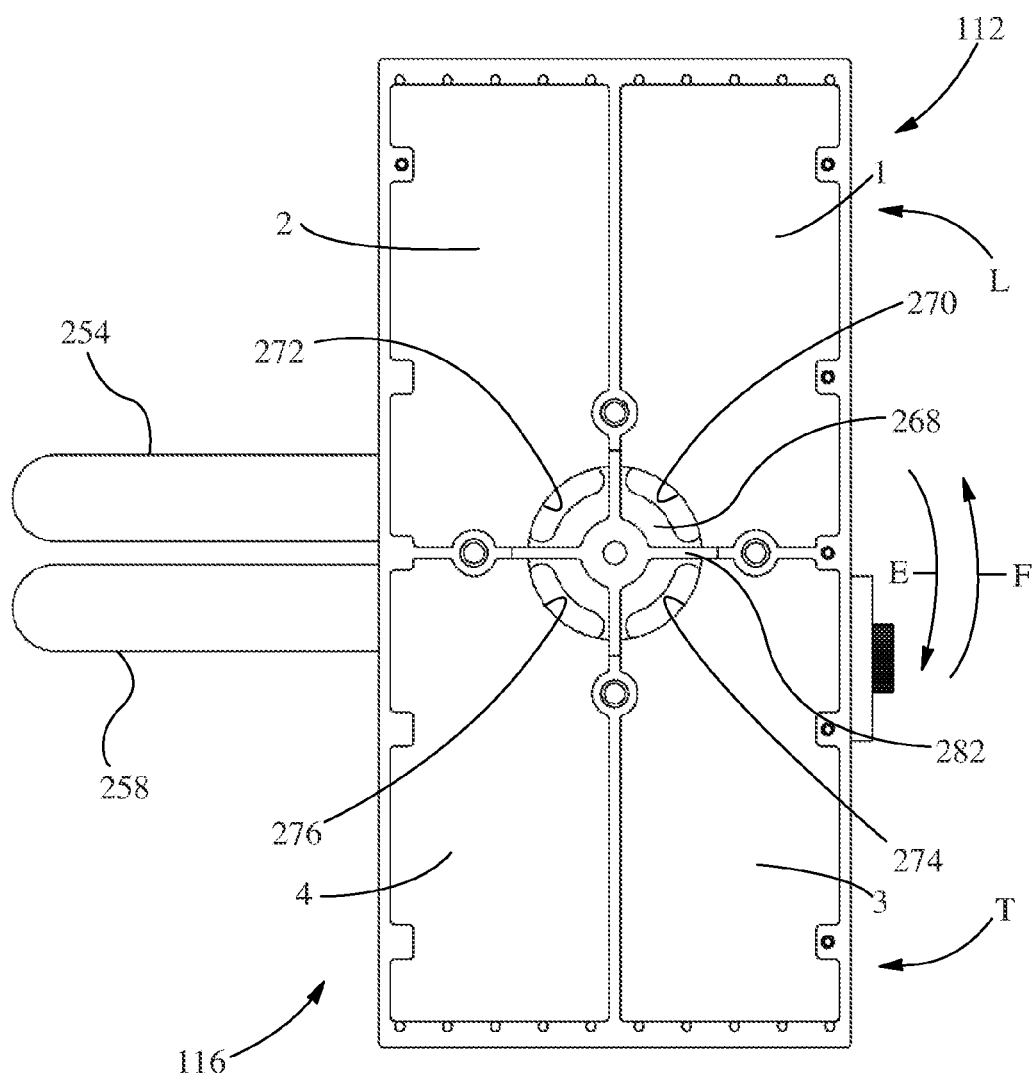
Figure 35:
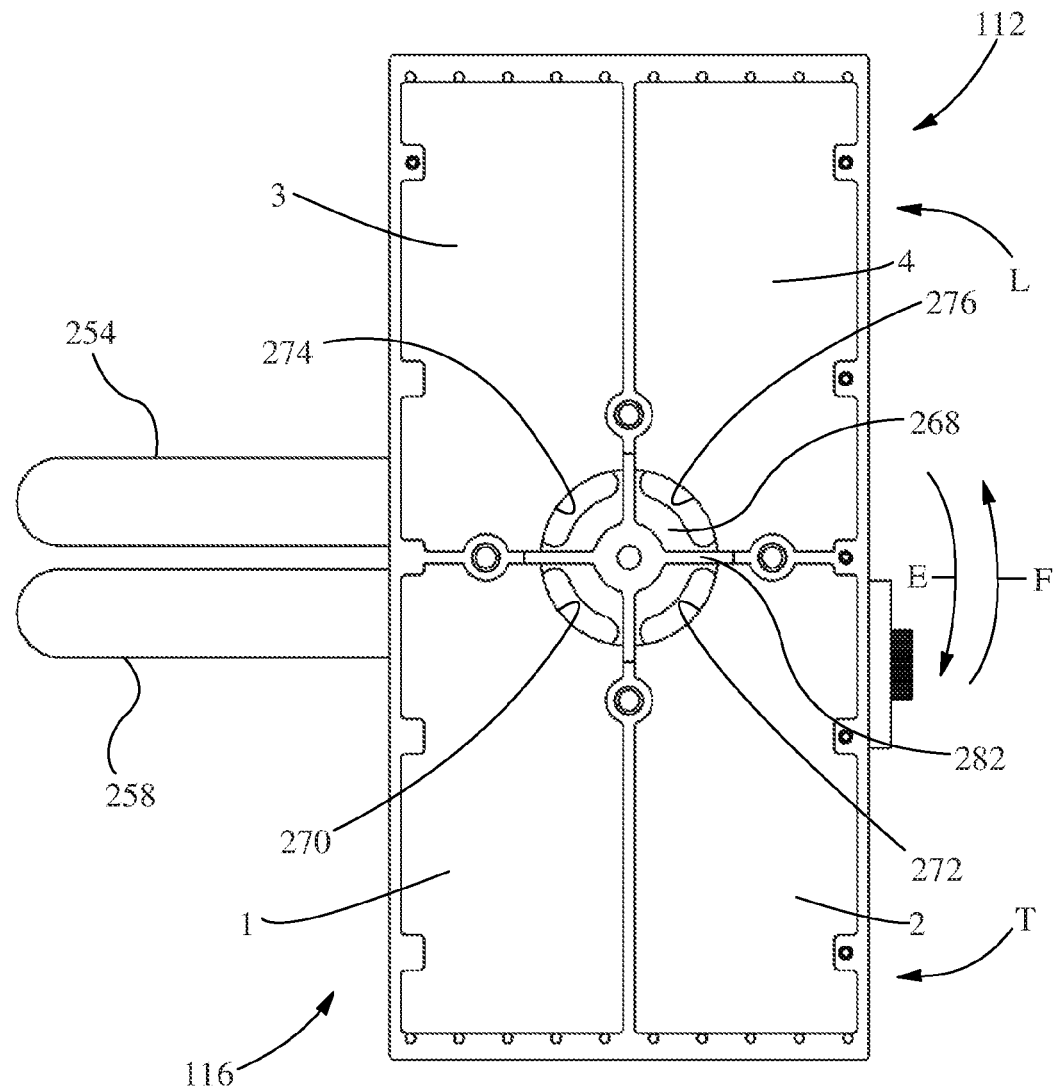

In one embodiment referring to FIGS. 33 and 34, a distal portion of a transfer member 112 may comprise a first zone 1, a second zone 2, a third zone 3, and a fourth zone 4. Each of the four zones may comprise fluid ports 230 defined through a transfer surface 136 thereof. The first fluid conduit 254 may be in fluid communication with the first zone 1 and the second zone 2 when the distal portion of the transfer member is in the first position 116 and may be in fluid communication with the first zone 1 and the third zone 3 when the distal portion of the transfer member 112 is rotated into the second position 118 in the direction of arrow E in FIG. 33 and in the direction of arrow F in FIG. 34. The second fluid conduit 258 may be in fluid communication with the third zone 3 and the fourth zone 4 when the distal portion of the transfer member 112 is in the first position 116 and may be in fluid communication with the fourth zone 4 and the second zone 2 when the distal portion of the transfer member 112 is rotated in the second position 118 in the direction of arrow E in FIG. 33 and in the direction of arrow F in FIG. 34.

For purposes of the claims and this paragraph, the first fluid conduit 254 may be referred to as a second fluid conduit and the second fluid conduit 258 may be referred to as a first fluid conduit. The fluid conduits are merely called out as "first" and "second" in the specification, for purposes of illustration and numbering, but this numbering is not intended to be limiting in the claims. The fluid conduits may be in fluid communication with either of the first or second fluid movement devices. In such an embodiment, referring to FIGS. 35 and 36, a distal portion of a transfer member 112 may comprise a first zone 1, a second zone 2, a third zone 3, and a fourth zone 4. The first fluid conduit 258 may be in fluid communication with the first zone 1 and the second zone 2 when the distal portion of the transfer member 112 is in the first position 116 and may be in fluid communication with the first zone 1 and the third zone 3 when the distal portion of the transfer member 112 is rotated into the second position 118 in the direction of arrow F in FIG. 35 and in the direction of arrow E in FIG. 36. The second fluid conduit 254 may be in fluid communication with the third zone 3 and the fourth zone 4 when the distal portion of the transfer member 112 is in the first position 116 and may be in fluid communication with the fourth zone 4 and the second zone 2 when the distal portion of the transfer member 112 is rotated into the second position 118 in the direction of arrow F in FIG. 35 and in the direction of arrow E in FIG. 36. The transfer surface 136 may be rotated between about 70 degrees and about 110 degrees, between about 80 degrees and about 100 degrees, about 90 degrees (e.g., +/−3 degrees), or 90 degrees, specifically reciting each degree within the above-cited ranges, when the distal portion of the transfer member 112 is rotated between the first position 116 and the second position 118 about the second rotation axis 164.

In one embodiment, referring again to FIGS. 33-36, each of or one of the distal portions of the transfer members 112 may comprise a first zone 1, a second zone 2, a third zone 3, a fourth zone 4, and optionally more than four zones, such as five, six, seven, eight, nine, or sixteen zones, for example. An example of a five zone system may comprise a zone of additional fluid ports along the leading edge of the transfer surface 136 so that when the transfer surface 136 is moved into the second position 118, the leading edge may be blown off at a slightly different timing (e.g., before) as the leading portion (i.e., ½ of the discrete article controlled by two additional zones) is blown off. Each of the zones may comprise fluid ports 230 defined in a transfer surface 136 thereof. The zones may be in fluid communication with the fluid ports 230. The first zone 1 and the second zone 2 may at least partially form, or form all of, the trailing portion T or the leading portion L of each of or one of the distal portions of the transfer members 112 when each of or one of the distal portions of the transfer members 112 is in the first position 116. The first zone 1 or the second zone 2 and the third zone 3 or the fourth zone 4 (e.g., the first zone 1 and the third zone 3) may at least partially form, or fully form, the same of the trailing portion T or the leading portion L of each of or one of the distal portions of the transfer members 112 when each of or one of the distal portions of the transfer members 112 is rotated into the second position 118 in the directions of arrows E or F. A fluid conduit 254 or 258 may be in fluid communication with the first zone 1 and the second zone 2 when each of or one of the distal portions of the transfer members 112 is in the first position 116 and with the first zone 1 or the second zone 2 and the third zone 3 or the fourth zone 4 when each of or one of the distal portions of the transfer members 112 is rotated into the second position 118 in the directions of arrows E and F. A second fluid conduit 254 or 258 may be in fluid communication with the third zone 3 and the fourth zone 4 when each of or one of the distal portions of the transfer members 112 is in the first position 116 and with the other of the first zone 1 or the second zone 2 and the other of the third zone 3 or the fourth zone 4 (e.g., the second zone 2 and the fourth zone 4) when each of or one of the distal portions of the transfer members 112 is rotated into the second position in the directions of arrows E and F.

Although the fluid system is illustrated, as an example, in use with the transfer assembly 100 and the rotation assembly 170, the fluid system may also be applied to other transfer assemblies and rotation assemblies known to or developed by those of skill in the art and may function independent of the transfer assembly 100 and the rotation assembly 170. Those of skill in the art will understand how to adapt the fluid system to work with other transfer assemblies or rotation assemblies. In one embodiment, the other transfer assemblies and rotation assemblies that the fluid system may be used with may not have transfer members that move radially relative to their rotation axis, for example.

In one embodiment, a method of applying a fluid pressure to a portion of a transfer member of a transfer assembly is provided. The fluid pressure is then applied to discrete articles being transferred by the transfer members of the transfer assembly. The transfer assembly may comprise a frame defining a first rotation axis and one or more transfer members. Portions of each of the transfer members may comprise a leading portion and a trailing portion when rotating about the first rotation axis. The portions of each of or one of the transfer members may also be rotatable about a second rotation axis between a first position and a second position during rotation about the first rotation axis. The method may comprise providing a fluid conduit in fluid communication with the leading portion or the trailing portion of portions of each of or one of the transfer members when the portions of the transfer members are in the first position, rotating the portions of the transfer member between the first position and at least the second position about the second rotation axis, and maintaining the fluid conduit in fluid communication with the same of the leading portion or the trailing portion of the portions of each of or one of the transfer members after the portions of each of or one of the transfer members is moved into the second position. The method may also comprise providing a second fluid conduit in fluid communication with the other of the leading portion or the trailing portion (i.e., if the fluid conduit is in fluid communication with the leading portion, the second fluid conduit is in fluid communication with the trailing portion) of the portions of each of or one of the transfer members when the portions of each of or one of the transfer members is in the first position, and maintaining the second fluid conduit in fluid communication with the same of the leading portion or the trailing portion of the portions of each of or one of the transfer members after the portions each of or one of the transfer members is moved into the second position. The method may also comprise independently or selectively controlling the flow of a fluid through the fluid conduit and the second fluid conduit. Different fluid pressures may be applied in the fluid conduit and the second fluid conduit, for example, by generating a positive fluid pressure in the fluid conduit and generating a negative fluid pressure in the second fluid conduit. The positive and negative fluid pressures may be applied to portions of each of or one of the transfer members simultaneously. In other embodiments, the different fluid pressures may be a first negative fluid pressure in the fluid conduit and a second, different negative fluid pressure in the second fluid conduit. One of the two different fluid pressures may be zero. In one embodiment, the fluid pressures in each of the fluid conduits may be independently adjusted. One or more fluid movement devices may be positioned in fluid communication with the fluid conduit and the second fluid conduit. The method may also comprise repitching a discrete article situated on a transfer surface of portions of each of or one of the transfer members between a pickup point or zone (e.g., first moving carrier member) and a discharge point or zone (e.g., second moving carrier member).

In various embodiments, the methods of transferring discrete articles to or from a moving carrier member or from a first moving carrier member to a second carrier member will be discussed in greater detail. As an example of performing the method, the reader is directed to the transfer assembly, rotation assembly, and fluid system discussion herein, however, the present method disclosure is merely referring to the transfer assembly, rotation assembly, and fluid system discussion as an example. As such, other transfer assemblies, rotation assemblies, and fluid systems are within the scope of the method disclosure. Further, to perform the method, some specific features or components of the transfer assembly, rotation assembly, and fluid systems described above may not be necessary and/or may be interchanged with other features or components.

In one embodiment, a method of transferring discrete articles from or to a moving carrier member is disclosed. The method may use a transfer assembly comprising a frame defining a rotation axis and one or more transfer members each comprising a flat, or a substantially flat, transfer surface. In other embodiments, the transfer surface may comprise flat portions and other arcuate or otherwise profiled portions. Each of the transfer surfaces may be configured to receive one or more of the discrete articles. The method may comprise rotating the one or more transfer members about the rotation axis and maintaining the transfer surfaces at a constant or substantially constant distance or minimum distance away from the moving carrier member at or proximate to the point of discrete article transfer. The method may further comprise moving the transfer surface radially inwardly and radially outwardly relative to the rotation axis at or proximate to the point of discrete article transfer and maintaining the transfer surface at the same or at substantially the same tangential velocity as the velocity or tangential velocity of the moving carrier member at or proximate to the point of discrete article transfer. The transfer surface, and other portions of the transfer member, may be rotated about a second rotation axis during rotation of the transfer member about the rotation axis between a first position and at least a second position. The second rotation axis may be positioned transverse, perpendicular, or generally perpendicular to the rotation axis. In other embodiments, the rotation axis may extend in a first direction and the second rotation axis may extend in a second, different direction. In one instance, the transfer surface has a longitudinal or other axis running through its midpoint and that axis may be rotated between 45 to 180 degrees, 80 to 100 degrees, or 90 degrees, specifically reciting all 0.5 degree increments within the specified ranges, between the first position and the second position about the second rotation axis. In one embodiment, the transfer surface may be rotated in a first rotational direction from the first position into the second direction and in a second rotational direction from the second position into the first position. The first and second rotational directions may be the same or different. The method may further comprise using a radial displacement mechanism, such as the track and one or more follower members described herein, operably engaged with the transfer member to maintain the transfer surface at the constant or the substantially constant minimum distance away from the moving carrier member at the point of discrete article transfer.

In another embodiment, the method may use a transfer assembly comprising a frame defining a rotation axis and one or more transfer members each comprising a transfer surface configured to receive one or more discrete articles. The transfer surface may be flat, substantially flat, or may comprise flat portions. The method may comprise rotating the one or more transfer members about the rotation axis such that each transfer surface has a tangential velocity the same as, or substantially the same as, the velocity or tangential velocity of the moving carrier member at the point of discrete article transfer and maintaining each transfer surface at a constant or a substantially constant minimum distance away from the moving carrier member at the point of discrete article transfer. The constant or substantially constant minimum distance may be maintained by moving each transfer surface radially inwardly and radially outwardly relative to the rotation axis at the point of discrete article transfer. Maintaining the tangential velocity of the transfer surface the same as or substantially the same as the velocity or tangential velocity of the moving carrier member may comprise moving the transfer surface radially inwardly and radially outwardly relative to the rotation axis at the point of discrete article transfer. The method may also comprise rotating the transfer surface about a second rotation axis between a first position and at least a second position, including the radial movement during the rotation, as described above.

In one embodiment, a method of transferring discrete articles between a first moving carrier member and a second moving carrier member may use a transfer assembly comprising a frame defining a rotation axis and one or more transfer members each comprising a flat, a substantially flat, and/or an arcuate transfer surface. In other embodiments, the transfer surface may comprise flat portions. The transfer surface may be configured to receive one or more of the discrete articles. The method may comprise rotating the transfer member about the rotation axis and maintaining the flat or substantially flat transfer surface at a constant or a substantially constant minimum distance away from the first moving carrier member and the second moving carrier member at the points of discrete article transfer. The first moving carrier member may have a first velocity at the point of discrete article transfer and the second moving carrier member may have a second, different velocity at the point of discrete article transfer. The first velocity and the second velocity may be tangential velocities. The method may also comprise rotating the transfer surface about a second rotation axis between a first position and a second position, including the radial movement during the rotation, as described above.

In all of the methods described herein, the methods may comprise retaining one or more of the discrete article to the transfer surface by using fluid pressures, static, magnetic, and/or adhesive attraction, for example.

In one embodiment, the transfer members, wheels, fluid distribution disks 139, rotation assemblies, and/or any other part or component that rotates about the rotation axis 132 may comprise aluminum, steel, plastic, titanium, carbon fiber composite, and/or other high strength/light weight material. By using high strength/light weight materials, the amount of mass rotating about the rotation axis 132 may be decreased or reduced compared to related art transfer assemblies. This reduction in mass may allow the transfer assemblies of the present disclosure to operate at a higher throughput of discrete articles per minute.

In one embodiment, the transfer assemblies of the present disclosure may process or transfer over 800 discrete articles per minute, alternatively, over 900 discrete articles per minute, alternatively, over 1,000 discrete articles per minute, alternatively, over 1,100 discrete articles per minute, alternatively, over 1,200 discrete articles per minute, and alternatively, over 1,300 discrete articles per minute. In other embodiments, the transfer assemblies of the present disclosure may process or transfer between 600 and 1500 discrete articles per minute, specifically including each whole number within the specified range.

Any of the methods and apparatuses described herein may be used in conjunction with the inventive concepts disclosed in European Patent Application No. EP12162251.8, entitled METHOD AND APPARATUS FOR MAKING PERSONAL HYGIENE ABSORBENT ARTICLES, and filed on Mar. 29, 2012.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of transferring discrete articles from or to a rotating carrier member using a transfer assembly comprising a frame defining a rotation axis and a transfer member comprising a substantially flat transfer surface configured to receive one of the discrete articles, the method comprising:
  rotating the transfer member about the rotation axis; and
  maintaining the substantially flat transfer surface at a substantially constant minimum distance away from the rotating carrier member throughout a zone of discrete article transfer.

2. The method of claim 1, comprising moving the substantially flat transfer surface radially inwardly and radially outwardly relative to the rotation axis in the zone of discrete article transfer to maintain the substantially constant minimum distance.

3. The method of claim 1, comprising maintaining the substantially flat transfer surface at substantially the same tangential velocity as the velocity of the rotating carrier member in the zone of discrete article transfer.

4. The method of claim 1, comprising rotating the substantially flat transfer surface about a second rotation axis between a first position and a second position, wherein the rotation axis extends in a first direction, and wherein the second rotation axis extends in a second, different direction.

5. The method of claim 4, wherein the substantially flat transfer surface is rotated between about 80 degrees and about 100 degrees between the first position and the second position.

6. The method of claim 1, comprising using a radial displacement mechanism operably engaged with a portion of the transfer member to maintain the substantially flat transfer surface at the substantially constant minimum distance away from the rotating carrier member in the zone of discrete article transfer.

7. The method of claim 1, comprising maintaining a substantially constant pressure between the substantially flat transfer surface and the rotating carrier member.

8. The method of claim 7, wherein the substantially constant pressure enables substantially uniform bonding pressure between a discrete article and another component.

9. The method of claim 1, wherein the rotating carrier member comprises a roll.

10. A method of transferring discrete articles from or to a rotating carrier member using a transfer assembly comprising a frame defining a rotation axis and a transfer member comprising a transfer surface configured to receive one of the discrete articles, the method comprising:
  rotating the transfer member about the rotation axis such that the transfer surface has a tangential velocity substantially the same as the velocity of the rotating carrier member in a zone of discrete article transfer; and
  maintaining the transfer surface at a substantially constant minimum distance away from the rotating carrier member in the zone of discrete article transfer.

11. The method of claim 10, comprising moving the transfer surface radially inwardly and radially outwardly relative to the rotation axis in the zone of discrete article transfer to maintain the substantially constant minimum distance.

12. The method of claim 10, comprising moving the transfer surface radially inwardly and radially outwardly relative to the rotation axis in the zone of discrete article transfer to maintain the tangential velocity of the transfer surface substantially the same as the velocity of the rotating carrier member.

13. The method of claim 10, wherein the transfer surface is substantially flat.

14. The method of claim 10, comprising rotating the transfer surface about a second rotation axis between a first position and a second position about 70 to about 110 degrees, wherein the rotation axis extends in a first direction, and wherein the second rotation axis extends in a second, different direction.

15. The method of claim 14, comprising moving the transfer surface radially outwardly during at least a portion of the rotation between the first position and the second position.

16. The method of claim 10, wherein the rotating carrier member comprises a roll.

17. A method of transferring discrete articles from a first rotating carrier member to a second rotating carrier member using a transfer assembly comprising a frame defining a rotation axis and a transfer member comprising a substantially flat transfer surface configured to receive one of the discrete articles, the method comprising:
  rotating the transfer member about the rotation axis; and
  maintaining the substantially flat transfer surface at a substantially constant minimum distance away from the first rotating carrier member and the second rotating carrier member in zones of discrete article transfer.

18. The method of claim 17, wherein the first rotating carrier member has a first velocity in the zone of discrete article transfer, and wherein the second rotating carrier member has a second, different velocity in the zone of discrete article transfer.

19. The method of claim 18, wherein the first velocity is a first tangential velocity, and wherein the second velocity is a second tangential velocity.

20. The method of claim 17, comprising rotating a portion of the transfer member about a second rotation axis between the first rotating carrier member and the second rotating carrier member, wherein the rotation axis extends in a first direction, and wherein the second rotation axis extends in a second, different direction.

21. The method of claim 17, wherein the first and second rotating carrier members comprise rolls.

22. A method of transferring discrete articles from or to a rotating carrier member using a transfer assembly comprising a frame defining a rotation axis and a transfer member comprising a substantially flat transfer surface configured to receive one of the discrete articles, the method comprising:
  rotating the transfer member about the rotation axis;
  maintaining the substantially flat transfer surface at a substantially constant minimum distance away from the rotating carrier member at the point of discrete article transfer; and
  moving the substantially flat transfer surface radially relative to the rotation axis at the point of discrete article transfer to maintain the substantially constant minimum distance.

23. The method of claim 22, comprising maintaining the substantially flat transfer surface at substantially the same tangential velocity as the velocity of the rotating carrier member at the point of discrete article transfer.

24. The method of claim 22, comprising rotating the substantially flat transfer surface about a second rotation axis between a first position and a second position, wherein the rotation axis extends in a first direction, and wherein the second rotation axis extends in a second, different direction.

25. A method of transferring discrete articles from or to a rotating carrier member using a transfer assembly comprising a frame defining a rotation axis and a transfer member comprising a substantially flat transfer surface configured to receive one of the discrete articles, the method comprising:
  rotating the transfer member about the rotation axis;
  maintaining the substantially flat transfer surface at a substantially constant minimum distance away from the rotating carrier member at the point of discrete article transfer by radial displacement of a portion of the transfer surface relative to the rotational axis.

26. The method of claim 25, comprising maintaining the substantially flat transfer surface at substantially the same tangential velocity as the velocity of the rotating carrier member at the point of discrete article transfer.

27. The method of claim 25, comprising rotating the substantially flat transfer surface about a second rotation axis between a first position and a second position, wherein the rotation axis extends in a first direction, and wherein the second rotation axis extends in a second, different direction.

* * * * *